(12) United States Patent
Wang et al.

(10) Patent No.: US 11,072,659 B2
(45) Date of Patent: Jul. 27, 2021

(54) ANTI-PD-1 ANTIBODIES

(71) Applicant: Agency for Science, Technology and Research, Connexis (SG)

(72) Inventors: Cheng-I Wang, Singapore (SG); Hsueh Ling Janice Oh, Singapore (SG); Siok Ping Yeo, Singapore (SG); Jianrong Lionel Low, Singapore (SG); Hwee Ching Tan, Singapore (SG)

(73) Assignee: Agency for Science, Technology and Research, Connexis (SG)

( * ) Notice: Subject to any disclaimer, the term of this patent is extended or adjusted under 35 U.S.C. 154(b) by 167 days.

(21) Appl. No.: 16/360,445

(22) Filed: Mar. 21, 2019

(65) Prior Publication Data

US 2019/0292261 A1 Sep. 26, 2019

Related U.S. Application Data

(63) Continuation of application No. 15/521,434, filed as application No. PCT/SG2015/050413 on Oct. 27, 2015, now Pat. No. 10,280,224.

(30) Foreign Application Priority Data

Oct. 27, 2014 (GB) ..................................... 1419084

(51) Int. Cl.
*C07K 16/28* (2006.01)
*C07K 16/00* (2006.01)
*A61K 39/00* (2006.01)

(52) U.S. Cl.
CPC ........ *C07K 16/2818* (2013.01); *C07K 16/005* (2013.01); *A61K 2039/505* (2013.01); *C07K 2317/31* (2013.01); *C07K 2317/33* (2013.01); *C07K 2317/51* (2013.01); *C07K 2317/515* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 8,067,544 | B2 | 11/2011 | Landes et al. |
| 8,128,929 | B2 | 3/2012 | Loizos et al. |
| 9,771,425 | B2 | 9/2017 | Wang et al. |
| 2008/0085241 | A1 | 4/2008 | Stassar et al. |
| 2013/0052200 | A1 | 2/2013 | Dodel et al. |
| 2015/0290316 | A1 | 10/2015 | Graziano et al. |
| 2017/0313776 | A1* | 11/2017 | Zhou ........................ A61P 25/28 |

FOREIGN PATENT DOCUMENTS

| | | |
|---|---|---|
| CN | 102898528 W | 1/2013 |
| WO | WO-2004-056875 | 7/2004 |
| WO | WO-2004-084823 | 10/2004 |
| WO | WO-2006-121168 | 11/2006 |
| WO | WO-2006-138729 | 12/2006 |
| WO | WO-2008-017828 | 2/2008 |
| WO | WO-2008-156712 | 12/2008 |
| WO | WO-2009-018411 | 2/2009 |
| WO | WO-2010-077634 | 7/2010 |
| WO | WO-2011-107544 | 9/2011 |
| WO | WO-2011-110621 | 9/2011 |
| WO | WO-2011-159877 | 12/2011 |
| WO | WO-2012-004773 | 1/2012 |
| WO | WO-2012-096924 | 7/2012 |
| WO | WO-2012-135408 | 10/2012 |
| WO | WO-2012-145493 | 10/2012 |
| WO | WO-2014-059251 | 4/2014 |
| WO | WO-2014-066834 | 5/2014 |
| WO | WO-2014-159562 | 10/2014 |
| WO | WO-2014-209804 | 12/2014 |
| WO | WO-2015-016718 | 2/2015 |

OTHER PUBLICATIONS

Dyck et al., Immune checkpoints and their inhibition in cancer and infectious diseases. Eur J Immunol. May 2017;47(5):765-779. doi: 10.1002/eji.201646875. Epub Apr. 24, 2017.
Barber et al. (2006) Nature 439:682-687 "Restoring function in exhausted CD8 T cells during chronic viral infection".
Berger et al. (2008) Clin Cancer Res 14(10):3044-3051 "Phase I Safety and Pharmacokinetic Study of CT-011, a Humanized Antibody Interacting with PD-1, in Patients with Advanced Hematologic Malignancies".
Butler et al. (2012) Nature Immunology 13(2):188-195 "Therapeutic blockade of PDL-L1 and LAG-3 rapidly clears established blood-stage Plasmodium infection".
Chen et al. (2010) Hybridoma 29(2):153-160 "Generation and haracterization of Four Novel Monoclonal Antibodies Against Human Programmed Death-1 Molecule".
Chu and Neelapu (2014) OncoImmunology 3(3):e28101.1-e28101.3 "Anti-PD-1 antibodies for the treatment of B-cell lymphoma".
Extended European Search Report issued in EP 15855595.3 dated Apr. 26, 2018.
Hamid et al., "Safety and Tumor Responses with Lambrolizumab (Anti-PD-1) in Melanoma", New England Journal of Medicine, vol. 369, No. 2, Jul. 11, 2013, pp. 134-144, DOI: 10.1056/NEJMoa1305133.
International Preliminary Report on Patentability dated Oct. 3, 2016 in PCT/SG2015/050413.
International Search Report dated Dec. 11, 2015 in PCT/SG2015/050413.
Kontermann (2012) mAbs 4(2):182-197 "Dual targeting strategies with bispecific antibodies".

(Continued)

*Primary Examiner* — Peter J Reddig
(74) *Attorney, Agent, or Firm* — Wolf, Greenfield & Sacks, P.C.

(57) ABSTRACT

Anti-PD-1 antibodies are disclosed. Also disclosed are pharmaceutical compositions comprising such antibodies, and uses and methods using the same.

20 Claims, 54 Drawing Sheets

Specification includes a Sequence Listing.

(56) References Cited

OTHER PUBLICATIONS

McMahan et al. (2010) The Journal of Clinical Investigation 120(12):4546-4557 "Tim-3 expression of PD-1+ HCV-specific human CTLs is associated with viral persistence, and its blockade restores hepatocyte-directed in vitro cytotoxicity".
Said et al. (2010) Nature Medicine16(4):452-460 "Programmed death-1-induced interleukin-10 production by monocytes impairs $CD4^+$ T cell activation during HIV infection".
Topalian et al. (2012) NEJM 366(26):2443-2454, "Safety, Activity, and Immune Correlates of Anti-PD-1 Antibody in Cancer".
Wang et al., "In Vitro Characterization of the Anti-PD-1 Antibody Nivolumab, BMS-936558, and In Vivo Toxicology in Non-Human Primates", Cancer Immunology Research vol. 2, No. .9, May 2014, pp. 846-856, DOI: 10.1158/2326-6066.CIR-14-0040.
Wherry (2011) Nature Immunology 12(6):492-499 "T cell exhaustion".

\* cited by examiner

Figure 1A

A3 clone

LPVLTQPPSASGTPGQRVTISCSGSSSNIKFNSVNWYQQLPGTAPKLLIYSNNQRPSGVPDRFSGSKSGTSASLAISGLQSEDEADYFCASWDDVLYGSVFGGGTKLTVL (SEQ ID NO:1)

LC-CDR1: SGSSSNIKFNSVN (SEQ ID NO:25)
LC-CDR2: SNNQRPS (SEQ ID NO:26)
LC-CDR3: ASWDDVLYGSV (SEQ ID NO:27)

Figure 1B

A10 clone

LPVLTQPPSASGTPGQRVTISCSGSSSNIKFNSVNWYQQLPGTAPKLLIYSNNQRPSGVPDRFSGSKSGTSASLAISGLQSEDEADYFCASWDDYYYGTIFGGGTKLTVL (SEQ ID NO:2)

LC-CDR1: SGSSSNIKFNSVN (SEQ ID NO:25)
LC-CDR2: SNNQRPS (SEQ ID NO:26)
LC-CDR3: ASWDDYYYGTI (SEQ ID NO:28)

Figure 1C

B6 clone

QSVLTQPPSASGTPGQRVTISCSGSSSNIKFNSVNWYQQLPGTAPKLLIYSNNQRPSGVPDRFSGSKSGTSASLAISGLQSEDEADY YCASWDDYLRGTVFGGGTKLTVL (SEQ ID NO:3)

LC-CDR1: SGSSSNIKFNSVN (SEQ ID NO:25)
LC-CDR2: SNNQRPS (SEQ ID NO:26)
LC-CDR3: ASWDDYLRGTV (SEQ ID NO:29)

C4 clone

QSVLTQPPSASGTPGQRVTISCSGSSSNIKFNSVNWYQQLPGTAPKLLIYSNNQRPSGVPDRFSGSKSGTSASLAISGLQSEDEADY YCSAWDDYLHGTVFGGGTKLTVL (SEQ ID NO:4)

LC-CDR1: SGSSSNIKFNSVN (SEQ ID NO:25)
LC-CDR2: SNNQRPS (SEQ ID NO:26)
LC-CDR3: SAWDDYLHGTV (SEQ ID NO:30)

D4 clone

QSVLTQPPSASGTPGQRVTISCSGSSSNIKFNSVNWYQQLPGTAPKLLIYSNNQRPSGVPDRFSGSKSGTSASLAISGLQSEDEADY YCASWDDYVRGTMFGGGTKLTVL (SEQ ID NO:5)

LC-CDR1: SGSSSNIKFNSVN (SEQ ID NO:25)
LC-CDR2: SNNQRPS (SEQ ID NO:26)
LC-CDR3: ASWDDYVRGTM (SEQ ID NO:31)

Figure 1F

E1 clone

QSVLTQPPSASGTPGQRVTISCSGSSSNIKFNSVNWYQQLPGTAPKLLIYSNNQRPSGVPDRFSGSKSGTSASLAISGLQSEDEADY YCSSWDDFLRGTVFGGGTKLTVL (SEQ ID NO:6)

LC-CDR1: SGSSSNIKFNSVN (SEQ ID NO:25)
LC-CDR2: SNNQRPS (SEQ ID NO:26)
LC-CDR3: SSWDDFLRGTV (SEQ ID NO:32)

Figure 1G

F2 clone

QSVLTQPPSASGTPGQRVTISCSGSSSNIKFNSVNWYQQLPGTAPKLLIYSNNQRPSGVPDRFSGSKSGTSASLAISGLQSEDEADY
YCSSWDDDARGTIFGGGTKLTVL  (SEQ ID NO:7)

| | | |
|---|---|---|
| LC-CDR1: | SGSSSNIKFNSVN | (SEQ ID NO:25) |
| LC-CDR2: | SNNQRPS | (SEQ ID NO:26) |
| LC-CDR3: | SSWDDDARGTI | (SEQ ID NO:33) |

G1 clone

QSVLTQPPSASGTPGQRVTISCSGSSSNIKFNSVNWYQQLPGTAPKLLIYSNNQRPSGVPDRFSGSKSGTSASLAISGLQSEDEADY
YCAAWDDVYYGTIFGGGTKLTVL  (SEQ ID NO:8)

| | | |
|---|---|---|
| LC-CDR1: | SGSSSNIKFNSVN | (SEQ ID NO:25) |
| LC-CDR2: | SNNQRPS | (SEQ ID NO:26) |
| LC-CDR3: | AAWDDVYYGTI | (SEQ ID NO:34) |

G2 clone

QSVLTQPPSASGTPGQRVTISCSGSSSNIKFNSVNWYQQLPGTAPKLLIYSNNQRPSGVPDRFSGSKSGTSASLAISGLQSEDEADY
YCASWDDSLYGTVFGGGTKLTVL    (SEQ ID NO:9)

LC-CDR1:    SGSSSNIKFNSVN  (SEQ ID NO:25)

LC-CDR2:    SNNQRPS  (SEQ ID NO:26)

LC-CDR3:    ASWDDSLYGTV  (SEQ ID NO:35)

G10 clone

QSVLTQPPSASGTPGQRVTISCSGSSSNIKFNSVNWYQQLPGTAPKLLIYSNNQRPSGVPDRFSGSKSGTSASLAISGLQSEDEADY
YCAAWDDAYYGTIFGGGTKLTVL    (SEQ ID NO:10)

LC-CDR1:    SGSSSNIKFNSVN  (SEQ ID NO:25)

LC-CDR2:    SNNQRPS  (SEQ ID NO:26)

LC-CDR3:    AAWDDAYYGTI  (SEQ ID NO:36)

H4 clone

QSVLTQPPSASGTPGQRVTISCSGSGSSSNIKFNSVNWYQQLPGTAPKLLIYSNNQRPSGVPDRFSGSKSGTSASLAISGLQSEDEADY YCASWDDVYRGTVFGGGTKLTVL (SEQ ID NO:11)

LC-CDR1: SGSSSNIKFNSVN (SEQ ID NO:25)
LC-CDR2: SNNQRPS (SEQ ID NO:26)
LC-CDR3: ASWDDVYRGTV (SEQ ID NO:37)

H9 clone

QSVLTQPPSASGTPGQRVTISCSGSGSSSNIKFNSVNWYQQLPGTAPKLLIYSNNQRPSGVPDRFSGSKSGTSASLAISGLQSEDEADY YCSSWDDSLYGTIFGGGTKLTVL (SEQ ID NO:12)

LC-CDR1: SGSSSNIKFNSVN (SEQ ID NO:25)
LC-CDR2: SNNQRPS (SEQ ID NO:26)
LC-CDR3: SSWDDSLYGTI (SEQ ID NO:38)

A3 clone

QVQLVQSGGGVVQPGRSLRLSCAASGFTFSSYGMHWVRQAPGKGLEWVAVISYDGSNKYYADSVKGRFTISRDNSKNTLYLQMN
SLRAEDTAVYYCASDLGAGPYYYGKDHWGQGTTVTVSS (SEQ ID NO:13)

| | | |
|---|---|---|
| HC-CDR1: | GFTFSSYGMH | (SEQ ID NO:39) or |
| | SYGMH | (SEQ ID NO:89) |
| HC-CDR2: | VISYDGSNKYYADSVKG | (SEQ ID NO:40) |
| HC-CDR3: | DLGAGPYYYGKDH | (SEQ ID NO:41) |

A10 clone

QVQLVQSGGGVVQPGRSLRLSCAASGFTFSSYGMHWVRQAPGKGLEWVAVISYDGSNKYYADSVKGRFTISRDNSKNTLYLQMN
SLRAEDTAVYYCASDLGAGPYYYGKDVWGQGTTVTVSS (SEQ ID NO:14)

| | | |
|---|---|---|
| HC-CDR1: | GFTFSSYGMH | (SEQ ID NO:39) or |
| | SYGMH | (SEQ ID NO:89) |
| HC-CDR2: | VISYDGSNKYYADSVKG | (SEQ ID NO:40) |
| HC-CDR3: | DLGAGPYYYGKDV | (SEQ ID NO:42) |

B6 clone

QVQLVESGGGVVQPGRSLRLSCAASGFTFSSYGMHWVRQAPGKGLEWVAVISYDGSNKYYADSVKGRFTISRDNSKNTLYLQMN
SLRAEDTAVYYCASDYGAGPYYYGMDVWGQGTTVTVSS  (SEQ ID NO:15)

| | | |
|---|---|---|
| HC-CDR1: | GFTFSSYGMH | (SEQ ID NO:39) or |
| | SYGMH | (SEQ ID NO:89) |
| HC-CDR2: | VISYDGSNKYYADSVKG | (SEQ ID NO:40) |
| HC-CDR3: | DYGAGPYYYGMDV | (SEQ ID NO:43) |

C4 clone

QVQLVESGGGVVQPGRSLRLSCAASGFTFSSYGMHWVRQAPGKGLEWVAVISYDGSNKYYADSVKGRFTISRDNSKNTLYLQMN
SLRAEDTAVYYCASDLGAGPYYYGLDVWGQGTTVTVSS  (SEQ ID NO:16)

| | | |
|---|---|---|
| HC-CDR1: | GFTFSSYGMH | (SEQ ID NO:39) or |
| | SYGMH | (SEQ ID NO:89) |
| HC-CDR2: | VISYDGSNKYYADSVKG | (SEQ ID NO:40) |
| HC-CDR3: | DLGAGPYYYGLDV | (SEQ ID NO:44) |

D4 clone

QVQLVESGGGVVQPGRSLRLSCAASGFTFSSYGMHWVRQAPGKGLEWVAVISYDGSNKYYADSVKGRFTISRDNSKNTLYLQMN
SLRAEDTAVYYCASDLGAGPYYYGMDVWGQGTTVTVSS  (SEQ ID NO:17)

| | | |
|---|---|---|
| HC-CDR1: | GFTFSSYGMH | (SEQ ID NO:39) or |
| | SYGMH | (SEQ ID NO:89) |
| HC-CDR2: | VISYDGSNKYYADSVKG | (SEQ ID NO:40) |
| HC-CDR3: | DLGAGPYYYGMDV | (SEQ ID NO:45) |

E1 clone

QVQLVESGGGVVQPGRSLRLSCAASGFTFSSYGMHWVRQAPGKGLEWVAVISYDGSNKYYADSVKGRFTISRDNSKNTLYLQMN
SLRAEDTAVYYCASDLGAGPYYYGMDVWGQGTTVTVSS  (SEQ ID NO:18)

| | | |
|---|---|---|
| HC-CDR1: | GFTFSSYGMH | (SEQ ID NO:39) or |
| | SYGMH | (SEQ ID NO:89) |
| HC-CDR2: | VISYDGSNKYYADSVKG | (SEQ ID NO:40) |
| HC-CDR3: | DLGAGPYYYGMDV | (SEQ ID NO:46) |

F2 clone

QVQLVESGGGVVQPGRSLRLSCAASGFTFSSYGMHWVRQAPGKGLEWVAVISYDGSNKYYADSVKGRFTISRDNSKNTLYLQMN
SLRAEDTAVYYCASDLGAGPYYYGMDVWGQGTTVTVSS  (SEQ ID NO:19)

HC-CDR1:    GFTFSSYGMH          (SEQ ID NO:39) or
            SYGMH               (SEQ ID NO:89)
HC-CDR2:    VISYDGSNKYYADSVKG   (SEQ ID NO:40)
HC-CDR3:    DLGAGPYYYGMDV       (SEQ ID NO:47)

G1 clone

QVQLVESGGGVVQPGRSLRLSCAASGFTFSSYGMHWVRQAPGKGLEWVAVISYDGSNKYYADSVKGRFTISRDNSKNTLYLQMN
SLRAEDTAVYYCASDLGAGPYYYGMDVWGQGTTVTVSS  (SEQ ID NO:20)

HC-CDR1:    GFTFSSYGMH          (SEQ ID NO:39) or
            SYGMH               (SEQ ID NO:89)
HC-CDR2:    VISYDGSNKYYADSVKG   (SEQ ID NO:40)
HC-CDR3:    DLGAGPYYYGMDV       (SEQ ID NO:48)

G2 clone

QVQLVESGGGVVQPGRSLRLSCAASGFTFSSYGMHWVRQAPGKGLEWVAVISYDGSNKYYADSVKGRFTISRDNSKNTLYLQMN
SLRAEDTAVYYCASDLGAGPYYYGMDVWGQGTTVTVSS  (SEQ ID NO:21) or

HC-CDR1:    GFTFSSYGMH              (SEQ ID NO:39) or

SYGMH                    (SEQ ID NO:89)

HC-CDR2:    VISYDGSNKYYADSVKG        (SEQ ID NO:40)

HC-CDR3:    DLGAGPYYYGMDV            (SEQ ID NO:49)

G10 clone

QVQLVESGGGVVQPGRSLRLSCAASGFTFSSYGMHWVRQAPGKGLEWVAVISYDGSNKYYADSVKGRFTISRDNSKNTLYLQMN
SLRAEDTAVYYCASDYGAGPYYYGMDVWGQGTTVTVSS  (SEQ ID NO:22) or

HC-CDR1:    GFTFSSYGMH              (SEQ ID NO:39) or

SYGMH                    (SEQ ID NO:89)

HC-CDR2:    VISYDGSNKYYADSVKG        (SEQ ID NO:40)

HC-CDR3:    DYGAGPYYYGMDV            (SEQ ID NO:50)

H4 clone

QVQLVESGGGVVQPGRSLRLSCAASGFTFSSYGMHWVRQAPGKGLEWVAVISYDGSNKYYADSVKGRFTISRDNSKNTLYLQMN
SLRAEDTAVYYCASDLGSGYYLYGMDVWGQGTTVTVSS (SEQ ID NO:23)

| | | |
|---|---|---|
| HC-CDR1: | GFTFSSYGMH | (SEQ ID NO:39) or |
| | SYGMH | (SEQ ID NO:89) |
| HC-CDR2: | VISYDGSNKYYADSVKG | (SEQ ID NO:40) |
| HC-CDR3: | DLGSGYYLYGMDV | (SEQ ID NO:51) |

H9 clone

QVQLVESGGGVVQPGRSLRLSCAASGFTFSSYGMHWVRQAPGKGLEWVAVISYDGSNKYYADSVKGRFTISRDNSKNTLYLQMN
SLRAEDTAVYYCASDLGAGPYYYGMDVWGQGTTVTVSS (SEQ ID NO:24)

| | | |
|---|---|---|
| HC-CDR1: | GFTFSSYGMH | (SEQ ID NO:39) or |
| | SYGMH | (SEQ ID NO:89) |
| HC-CDR2: | VISYDGSNKYYADSVKG | (SEQ ID NO:40) |
| HC-CDR3: | DLGAGPYYYGMDV | (SEQ ID NO:52) |

Figure 2L

| Clone | CDR L1 | CDR L2 | CDR L3 |
|---|---|---|---|
| Light Chain | | | |
| A3 | SGSSSNIKFNSVN (SEQ ID NO:25) | SNNQRPS (SEQ ID NO:26) | ASWDDVLYGSV (SEQ ID NO:27) |
| A10 | SGSSSNIKFNSVN (SEQ ID NO:25) | SNNQRPS (SEQ ID NO:26) | ASWDDYYYGTI (SEQ ID NO:28) |
| B6 | SGSSSNIKFNSVN (SEQ ID NO:25) | SNNQRPS (SEQ ID NO:26) | ASWDDYLRGTV (SEQ ID NO:29) |
| C4 | SGSSSNIKFNSVN (SEQ ID NO:25) | SNNQRPS (SEQ ID NO:26) | SAWDDYLHGTV (SEQ ID NO:30) |
| D4 | SGSSSNIKFNSVN (SEQ ID NO:25) | SNNQRPS (SEQ ID NO:26) | ASWDDYVRGTM (SEQ ID NO:31) |
| E1 | SGSSSNIKFNSVN (SEQ ID NO:25) | SNNQRPS (SEQ ID NO:26) | SSWDDFLRGTV (SEQ ID NO:32) |
| F2 | SGSSSNIKFNSVN (SEQ ID NO:25) | SNNQRPS (SEQ ID NO:26) | SSWDDDARGTI (SEQ ID NO:33) |
| G1 | SGSSSNIKFNSVN (SEQ ID NO:25) | SNNQRPS (SEQ ID NO:26) | AAWDDVYYGTI (SEQ ID NO:34) |
| G2 | SGSSSNIKFNSVN (SEQ ID NO:25) | SNNQRPS (SEQ ID NO:26) | ASWDDSLYGTV (SEQ ID NO:35) |
| G10 | SGSSSNIKFNSVN (SEQ ID NO:25) | SNNQRPS (SEQ ID NO:26) | AAWDDAYYGTI (SEQ ID NO:36) |
| H4 | SGSSSNIKFNSVN (SEQ ID NO:25) | SNNQRPS (SEQ ID NO:26) | ASWDDVYRGTV (SEQ ID NO:37) |
| H9 | SGSSSNIKFNSVN (SEQ ID NO:25) | SNNQRPS (SEQ ID NO:26) | SSWDDSLYGTI (SEQ ID NO:38) |
| Consensus | SGSSSNIKFNSVN (SEQ ID NO:25) | SNNQRPS (SEQ ID NO:26) | $X_1X_2$WDD$X_3X_4X_5$G$X_6X_7$<br><br>$X_1$= A or S<br>$X_2$= S or A<br>$X_3$= V, Y, F, D, S or A<br>$X_4$= L, Y, V or A<br>$X_5$= Y, R or H<br>$X_6$= S, or T<br>$X_7$= V, I, or M<br><br>(SEQ ID NO:53) |

Figure 3A

| Clone | CDR L1 | CDR L2 | CDR L3 |
|---|---|---|---|
| Heavy Chain | | | |
| A3 | GFTFSSYGMH (SEQ ID NO:39) or SYGMH (SEQ ID NO:89) | VISYDGSNKYYADSVKG (SEQ ID NO:40) | DLGAGPYYYGKDH (SEQ ID NO:41) |
| A10 | GFTFSSYGMH (SEQ ID NO:39) or SYGMH (SEQ ID NO:89) | VISYDGSNKYYADSVKG (SEQ ID NO:40) | DLGAGPYYYGKDV (SEQ ID NO:42) |
| B6 | GFTFSSYGMH (SEQ ID NO:39) or SYGMH (SEQ ID NO:89) | VISYDGSNKYYADSVKG (SEQ ID NO:40) | DYGAGPYYYGMDV (SEQ ID NO:43) |
| C4 | GFTFSSYGMH (SEQ ID NO:39) or SYGMH (SEQ ID NO:89) | VISYDGSNKYYADSVKG (SEQ ID NO:40) | DLGAGPYYYGLDV (SEQ ID NO:44) |
| D4 | GFTFSSYGMH (SEQ ID NO:39) or SYGMH (SEQ ID NO:89) | VISYDGSNKYYADSVKG (SEQ ID NO:40) | DLGAGPYYYGMDV (SEQ ID NO:45) |
| E1 | GFTFSSYGMH (SEQ ID NO:39) or SYGMH (SEQ ID NO:89) | VISYDGSNKYYADSVKG (SEQ ID NO:40) | DLGAGPYYYGMDV (SEQ ID NO:46) |
| F2 | GFTFSSYGMH (SEQ ID NO:39) or SYGMH (SEQ ID NO:89) | VISYDGSNKYYADSVKG (SEQ ID NO:40) | DLGAGPYYYGMDV (SEQ ID NO:47) |
| G1 | GFTFSSYGMH (SEQ ID NO:39) or SYGMH (SEQ ID NO:89) | VISYDGSNKYYADSVKG (SEQ ID NO:40) | DLGAGPYYYGMDV (SEQ ID NO:48) |

Figure 3B

| | | | |
|---|---|---|---|
| G2 | GFTFSSYGMH (SEQ ID NO:39) or SYGMH (SEQ ID NO:89) | VISYDGSNKYYADSVKG (SEQ ID NO:40) | DLGAGPYYYGMDV (SEQ ID NO:49) |
| G10 | GFTFSSYGMH (SEQ ID NO:39) or SYGMH (SEQ ID NO:89) | VISYDGSNKYYADSVKG (SEQ ID NO:40) | DYGAGPYYYGMDV (SEQ ID NO:50) |
| H4 | GFTFSSYGMH (SEQ ID NO:39) or SYGMH (SEQ ID NO:89) | VISYDGSNKYYADSVKG (SEQ ID NO:40) | DLGSGYYLYGMDV (SEQ ID NO:51) |
| H9 | GFTFSSYGMH (SEQ ID NO:39) or SYGMH (SEQ ID NO:89) | VISYDGSNKYYADSVKG (SEQ ID NO:40) | DLGAGPYYYGMDV (SEQ ID NO:52) |
| Consensus | GFTFSSYGMH (SEQ ID NO:39) or SYGMH (SEQ ID NO:89) | VISYDGSNKYYADSVKG (SEQ ID NO:40) | $DZ_1GZ_2GZ_3YZ_4YGZ_5DZ_6$<br><br>$Z_1$= L or Y<br>$Z_2$= A or S<br>$Z_3$= P or Y<br>$Z_4$= Y or L<br>$Z_5$= K, M or L<br>$Z_6$= H or V<br>(SEQ ID NO:54) |

Figure 3C

Light chain variable domains

A3 clone

>A3_aa_L

LPVLTQPPSASGTPGQRVTISCSGSSSNIKFNSVNWYQQLPGTAPKLLIYSNNQRPSGVPD
RFSGSKSGTSASLAISGLQSEDEADYFCASWDDVLYGSVFGGGTKLTVL [SEQ ID NO. 1]

>A3_ntd_L

CTGCCTGTGCTGACTCAGCCCCCTCAGCGTCCGGGACCCCCGGGCAGAGGGTCACCATCT
CTTGTTCTGGAAGCAGCTCCAACATCAAATTTAACAGTGTTAACTGGTATCAGCAACTCCC
AGGAACGGCCCCCAAACTCCTCATCTATAGTAATAATCAGCGACCCTCAGGGGTCCCTGAC
CGATTCTCTGGCTCCAAGTCTGGCACTTCAGCCTCCCTGGCCATCAGTGGGCTCCAGTCTG
AGGATGAGGCTGATTATTTCTGTGCTTCTTGGGATGATGTTCTTTATGGATCTGTGTTCGG
CGGAGGGACCAAGCTGACCGTCCTG [SEQ ID NO. 55]

A10 clone

>A10_aa_L

LPVLTQPPSASGTPGQRVTISCSGSSSNIKFNSVNWYQQLPGTAPKLLIYSNNQRPSGVPD
RFSGSKSGTSASLAISGLQSEDEADYFCASWDDYYYGTIFGGGTKLTVL [SEQ ID NO. 2]

>A10_ntd_L

CTGCCTGTGCTGACTCAGCCCCCTCAGCGTCCGGGACCCCCGGGCAGAGGGTCACCATCT
CTTGTTCTGGAAGCAGCTCCAACATCAAATTTAACAGTGTTAACTGGTATCAGCAACTCCC
AGGAACGGCCCCCAAACTCCTCATCTATAGTAATAATCAGCGACCCTCAGGGGTCCCTGAC
CGATTCTCTGGCTCCAAGTCTGGCACTTCAGCCTCCCTGGCCATCAGTGGGCTCCAGTCTG
AGGATGAGGCTGATTATTTCTGTGCTTCTTGGGATGATTATTATTGGAACTATTTTCGG
CGGAGGGACCAAGCTGACCGTCCTG [SEQ ID NO. 56]

Figure 4A

A10 codon-optimised clone (induced modifications in the amino-acid sequence)

>A10_optimised_aa_L

QSVLTQPPSASGTPGQRVTISCSGSSSNIKFNSVNWYQQLPGTAPKLLIYSNNQRPSGVPD
RFSGSKSGTSASLAISGLQSEDEADYYCASWDDYYYGTIFGGGTKLTVL [SEQ ID NO. 57]

>A10_optimised_ntd_L

CAGAGCGTCCTGACACAGCCTCCTAGTGCAAGCGGAACCCCTGGGCAGAGAGTGACCATTT
CTTGTAGCGGCAGCAGCAGTAACATCAAGTTCAACTCCGTGAATTGGTATCAGCAGCTGCC
CGGAACTGCTCCTAAACTGCTGATCTACTCTAACAATCAGCGACCAAGTGGCGTCCCCGAC
CGGTTCAGCGGCTCCAAGTCTGGGACCAGTGCCTCACTGGCTATCAGCGGGCTCCAGTCCG
AGGACGAAGCAGATTACTATTGCGCCAGCTGGGACGATTACTATTACGGCACCATTTTCGG
CGGGGGAACAAAACTGACCGTCCTG [SEQ ID NO. 58]

B6 clone

>B6_aa_L

QSVLTQPPSASGTPGQRVTISCSGSSSNIKFNSVNWYQQLPGTAPKLLIYSNNQRPSGVPD
RFSGSKSGTSASLAISGLQSEDEADYYCASWDDYLRGTVFGGGTKLTVL [SEQ ID NO. 3]

>B6_ntd_L

CAGTCTGTGCTGACTCAGCCCCCCTCAGCGTCCGGGACCCCCGGGCAGAGGGTCACCATCT
CTTGTTCTGGAAGCAGCTCCAACATCAAATTTAACAGTGTTAACTGGTATCAGCAACTCCC
AGGAACGGCCCCCAAACTCCTCATCTATAGTAATAATCAGCGACCCTCAGGGGTCCCTGAC
CGATTCTCTGGCTCCAAGTCTGGCACTTCAGCCTCCCTGGCCATCAGTGGGCTCCAGTCTG
AGGATGAGGCTGATTATTACTGTGCTTCTTGGGATGATTATCTTCGTGGAACTGTTTTCGG
CGGAGGGACCAAGCTGACCGTCCTG [SEQ ID NO. 59]

B6 codon-optimised clone (no modifications of the amino-acid sequence)

>B6_optimised_ntd_L

CAGAGCGTGCTGACCCAGCCCCCCAGCGCCAGTGGAACACCCGGACAGAGAGTGACCATCA
GTTGCTCAGGCAGCTCCTCTAACATTAAGTTCAACTCTGTGAATTGGTATCAGCAGCTGCC
CGGAACTGCTCCTAAACTGCTGATCTATTCTAACAATCAGCGACCAAGTGGCGTCCCCGAC
CGGTTCAGCGGCTCCAAGTCTGGGACCAGTGCCTCACTGGCTATTAGCGGGCTCCAGTCCG
AGGACGAAGCAGATTACTATTGTGCCAGCTGGGACGATTACCTGAGGGGCACCGTGTTCGG
AGGAGGAACAAAACTGACCGTCCTG [SEQ ID NO. 60]

Figure 4B

C4 clone

>C4_aa_L

QSVLTQPPSASGTPGQRVTISCSGSSSNIKFNSVNWYQQLPGTAPKLLIYSNNQRPSGVPD
RFSGSKSGTSASLAISGLQSEDEADYYCSAWDDYLHGTVFGGGTKLTVL [SEQ ID NO. 4]

>C4_ntd_L

CAGTCTGTGCTGACTCAGCCCCCTCAGCGTCCGGGACCCCGGGCAGAGGGTCACCATCT
CTTGTTCTGGAAGCAGCTCCAACATCAAATTAACAGTGTTAACTGGTATCAGCAACTCCC
AGGAACGGCCCCCAAACTCCTCATCTATAGTAATAATCAGCGACCCTCAGGGGTCCCTGAC
CGATTCTCTGGCTCCAAGTCTGGCACTTCAGCCTCCTGGCCATCAGTGGGCTCCAGTCTG
AGGATGAGGCTGATTATTACTGTTCTGCTTGGGATGATTATCTTCATGGAACTGTGTTCGG
CGGAGGGACCAAGCTGACCGTCCTG [SEQ ID NO. 61]

C4 codon-optimised clone (no modifications of the amino-acid sequence)

>C4_optimised_ntd_L

CAGAGCGTCCTGACACAGCCCCCTTCCGCAAGTGGAACCCCTGGGCAGCGAGTGACTATTT
CATGCAGTGGATCTTCATCTAACATCAAGTTCAACTCCGTGAATTGGTATCAGCAGCTGCC
CGGAACTGCTCCTAAACTGCTGATCTATTCTAACAATCAGCGACCAAGTGGCGTCCCCGAC
CGGTTCAGCGGCTCCAAGTCTGGGACCAGTGCCTCACTGGCTATTAGCGGGCTCCAGTCCG
AGGACGAAGCAGATTACTATTGCAGCGCCTGGGACGATTACCTGCACGGCACCGTGTTCGG
AGGAGGAACAAAACTGACCGTCCTG [SEQ ID NO. 62]

D4 clone

>D4_aa_L

QSVLTQPPSASGTPGQRVTISCSGSSSNIKFNSVNWYQQLPGTAPKLLIYSNNQRPSGVPD
RFSGSKSGTSASLAISGLQSEDEADYYCASWDDYVRGTMFGGGTKLTVL [SEQ ID NO. 5]

>D4_ntd_L

CAGTCTGTGCTGACTCAGCCCCCTCAGCGTCCGGGACCCCGGGCAGAGGGTCACCATCT
CTTGTTCTGGAAGCAGCTCCAACATCAAATTAACAGTGTTAACTGGTATCAGCAACTCCC
AGGAACGGCCCCCAAACTCCTCATCTATAGTAATAATCAGCGACCCTCAGGGGTCCCTGAC
CGATTCTCTGGCTCCAAGTCTGGCACTTCAGCCTCCTGGCCATCAGTGGGCTCCAGTCTG
AGGATGAGGCTGATTATTACTGTGCTTCTTGGGATGATTATGTTCGTGGAACTATGTTCGG
CGGAGGGACCAAGCTGACCGTCCTG [SEQ ID NO. 63]

Figure 4C

E1 clone

>E1_aa_L

QSVLTQPPSASGTPGQRVTISCSGSSSNIKFNSVNWYQQLPGTAPKLLIYSNNQRPSGVPD
RFSGSKSGTSASLAISGLQSEDEADYYCSSWDDFLRGTVFGGGTKLTVL [SEQ ID NO. 6]

>E1_ntd_L

CAGTCTGTGCTGACTCAGCCCCCCTCAGCGTCCGGGACCCCCGGGCAGAGGGTCACCATCT
CTTGTTCTGGAAGCAGCTCCAACATCAAATTTAACAGTGTTAACTGGTATCAGCAACTCCC
AGGAACGGCCCCCAAACTCCTCATCTATAGTAATAATCAGCGACCCTCAGGGGTCCCTGAC
CGATTCTCTGGCTCCAAGTCTGGCACTTCAGCCTCCCTGGCCATCAGTGGGCTCCAGTCTG
AGGATGAGGCTGATTATTACTGTTCTTCTTGGGATGATTTTCTTCGTGGAACTGTTTTCGG
CGGAGGGACCAAGCTGACCGTCCTG [SEQ ID NO. 64]

F2 clone

>F2_aa_L

QSVLTQPPSASGTPGQRVTISCSGSSSNIKFNSVNWYQQLPGTAPKLLIYSNNQRPSGVPD
RFSGSKSGTSASLAISGLQSEDEADYYCSSWDDDARGTIFGGGTKLTVL [SEQ ID NO. 7]

>F2_ntd_L

CAGTCTGTGCTGACTCAGCCCCCCTCAGCGTCCGGGACCCCCGGGCAGAGGGTCACCATCT
CTTGTTCTGGAAGCAGCTCCAACATCAAATTTAACAGTGTTAACTGGTATCAGCAACTCCC
AGGAACGGCCCCCAAACTCCTCATCTATAGTAATAATCAGCGACCCTCAGGGGTCCCTGAC
CGATTCTCTGGCTCCAAGTCTGGCACTTCAGCCTCCCTGGCCATCAGTGGGCTCCAGTCTG
AGGATGAGGCTGATTATTACTGTTCTTCTTGGGATGATGATGCTCGTGGAACTATTTCGG
CGGAGGGACCAAGCTGACCGTCCTG [SEQ ID NO. 65]

Figure 4D

G1 clone

>G1_aa_L

QSVLTQPPSASGTPGQRVTISCSGSSSNIKFNSVNWYQQLPGTAPKLLIYSNNQRPSGVPD
RFSGSKSGTSASLAISGLQSEDEADYYCAAWDDVYYGTIFGGGTKLTVL [SEQ ID NO. 8]

>G1_ntd_L

CAGTCTGTGCTGACTCAGCCCCCCTCAGCGTCCGGGACCCCCGGGCAGAGGGTCACCATCT
CTTGTTCTGGAAGCAGCTCCAACATCAAATTTAACAGTGTTAACTGGTATCAGCAACTCCC
AGGAACGGCCCCCAAACTCCTCATCTATAGTAATAATCAGCGACCCTCAGGGGTCCCTGAC
CGATTCTCTGGCTCCAAGTCTGGCACTTCAGCCTCCTGGCCATCAGTGGGCTCCAGTCTG
AGGATGAGGCTGATTATTACTGTGCTGCTTGGGATGATGTTTATTATGGAACTATTTTCGG
CGGAGGGACCAAGCTGACCGTCCTG [SEQ ID NO. 66]

G2 clone

>G2_aa_L

QSVLTQPPSASGTPGQRVTISCSGSSSNIKFNSVNWYQQLPGTAPKLLIYSNNQRPSGVPD
RFSGSKSGTSASLAISGLQSEDEADYYCASWDDSLYGTVFGGGTKLTVL [SEQ ID NO. 9]

>G2_ntd_L

CAGTCTGTGCTGACTCAGCCCCCCTCAGCGTCCGGGACCCCCGGGCAGAGGGTCACCATCT
CTTGTTCTGGAAGCAGCTCCAACATCAAATTTAACAGTGTTAACTGGTATCAGCAACTCCC
AGGAACGGCCCCCAAACTCCTCATCTATAGTAATAATCAGCGACCCTCAGGGGTCCCTGAC
CGATTCTCTGGCTCCAAGTCTGGCACTTCAGCCTCCTGGCCATCAGTGGGCTCCAGTCTG
AGGATGAGGCTGATTATTACTGTGCTTCTTGGGATGATTCTCTTTATGGAACTGTTTTCGG
CGGAGGGACCAAGCTGACCGTCCTG [SEQ ID NO. 67]

Figure 4E

G10 clone

>G10_aa_L

QSVLTQPPSASGTPGQRVTISCSGSSSNIKFNSVNWYQQLPGTAPKLLIYSNNQRPSGVPD
RFSGSKSGTSASLAISGLQSEDEADYYCAAWDDAYYGTIFGGGTKLTVL [SEQ ID NO. 10]

>G10_ntd_L

CAGTCTGTGCTGACTCAGCCCCCCTCAGCGTCCGGGACCCCCGGGCAGAGGGTCACCATCT
CTTGTTCTGGAAGCAGCTCCAACATCAAATTTAACAGTGTTAACTGGTATCAGCAACTCCC
AGGAACGGCCCCCAAACTCCTCATCTATAGTAATAATCAGCGACCCTCAGGGGTCCCTGAC
CGATTCTCTGGCTCCAAGTCTGGCACTTCAGCCTCCCTGGCCATCAGTGGGCTCCAGTCTG
AGGATGAGGCTGATTATTACTGTGCTGCTTGGGATGATGCTTATTATGGAACTATTTTCGG
CGGAGGGACCAAGCTGACCGTCCTG [SEQ ID NO. 68]

H4 clone

>H4_aa_L

QSVLTQPPSASGTPGQRVTISCSGSSSNIKFNSVNWYQQLPGTAPKLLIYSNNQRPSGVPD
RFSGSKSGTSASLAISGLQSEDEADYYCASWDDVYRGTVFGGGTKLTVL [SEQ ID NO. 11]

>H4_ntd_L

CAGTCTGTGCTGACTCAGCCCCCCTCAGCGTCCGGGACCCCCGGGCAGAGGGTCACCATCT
CTTGTTCTGGAAGCAGCTCCAACATCAAATTTAACAGTGTTAACTGGTATCAGCAACTCCC
AGGAACGGCCCCCAAACTCCTCATCTATAGTAATAATCAGCGACCCTCAGGGGTCCCTGAC
CGATTCTCTGGCTCCAAGTCTGGCACTTCAGCCTCCCTGGCCATCAGTGGGCTCCAGTCTG
AGGATGAGGCTGATTATTACTGTGCTTCTTGGGATGATGTTTATCGTGGAACTGTTTTCGG
CGGAGGGACCAAGCTGACCGTCCTG [SEQ ID NO. 69]

Figure 4F

H4 codon-optimised clone (no modifications of the amino-acid sequence)

>H4_optimised_ntd_L

CAGAGCGTCCTGACACAGCCCCAAGCGCAAGCGGAACCCCCGGCCAGCGAGTGACCATTA
GTTGTAGTGGAAGTAGTAGTAACATCAAGTTCAACTCCGTGAATTGGTATCAGCAGCTGCC
CGGAACTGCTCCTAAACTGCTGATCTATTCTAACAATCAGCGACCAAGTGGCGTCCCCGAC
CGGTTCAGCGGCTCCAAGTCTGGGACCAGTGCCTCACTGGCTATTAGCGGGCTCCAGTCCG
AGGACGAAGCAGATTACTATTGCGCCAGCTGGGACGATGTGTACAGGGGCACCGTCTTCGG
CGGGGGAACAAAACTGACCGTCCTG [SEQ ID NO. 70]

H9 clone

>H9_aa_L

QSVLTQPPSASGTPGQRVTISCSGSSSNIKFNSVNWYQQLPGTAPKLLIYSNNQRPSGVPD
RFSGSKSGTSASLAISGLQSEDEADYYCSSWDDSLYGTIFGGGTKLTVL [SEQ ID NO. 12]

>H9_ntd_L

CAGTCTGTGCTGACTCAGCCCCCCTCAGCGTCCGGGACCCCCGGGCAGAGGGTCACCATCT
CTTGTTCTGGAAGCAGCTCCAACATCAAATTTAACAGTGTTAACTGGTATCAGCAACTCCC
AGGAACGGCCCCCAAACTCCTCATCTATAGTAATAATCAGCGACCCTCAGGGGTCCCTGAC
CGATTCTCTGGCTCCAAGTCTGGCACTTCAGCCTCCCTGGCCATCAGTGGGCTCCAGTCTG
AGGATGAGGCTGATTATTACTGTTCTTCTTGGGATGATTCTCTTTATGGAACTATTTTCGG
CGGAGGGACCAAGCTGACCGTCCTG [SEQ ID NO. 71]

Figure 4G

Heavy chain variable domains

A3 clone

\>A3_aa_H

QVQLVQSGGGVVQPGRSLRLSCAASGFTFSSYGMHWVRQAPGKGLEWVAVISYDGSNKYYA
DSVKGRFTISRDNSKNTLYLQMNSLRAEDTAVYYCASDLGAGPYYYGKDHWGQGTTVTVSS
[SEQ ID NO. 13]

\>A3_ntd_H

CAGGTCCAGCTGGTGCAGTCCGGGGGAGGCGTGGTCCAGCCTGGGCGGTCCCTGAGACTCT
CCTGTGCAGCCTCTGGATTCACCTTCAGTAGCTATGGCATGCACTGGGTCCGCCAGGCTCC
AGGCAAGGGGCTGGAGTGGGTGGCAGTTATATCATATGATGGAAGTAATAAATACTACGCA
GACTCCGTGAAGGGCCGATTCACCATCTCCAGAGACAATTCCAAGAACACGCTGTATCTGC
AAATGAACAGCCTGAGAGCCGAGGACACGGCTGTGTATTACTGTGCGAGTGATCTTGGTGC
TGGTCCTTATTATTATGGTAAGGATCATTGGGGCCAAGGGACCACGGTCACCGTCTCAAGC
[SEQ ID NO. 72]

A10 clone

\>A10_aa_H

QVQLVQSGGGVVQPGRSLRLSCAASGFTFSSYGMHWVRQAPGKGLEWVAVISYDGSNKYYA
DSVKGRFTISRDNSKNTLYLQMNSLRAEDTAVYYCASDLGAGPYYYGKDVWGQGTTVTVSS
[SEQ ID NO. 14]

\>A10_ntd_H

CAGGTCCAGCTGGTGCAGTCTGGGGGAGGCGTGGTCCAGCCTGGGCGGTCCCTGAGACTCT
CCTGTGCAGCCTCTGGATTCACCTTCAGTAGCTATGGCATGCACTGGGTCCGCCAGGCTCC
AGGCAAGGGGCTGGAGTGGGTGGCAGTTATATCATATGATGGAAGTAATAAATACTACGCA
GACTCCGTGAAGGGCCGATTCACCATCTCCAGAGACAATTCCAAGAACACGCTGTATCTGC
AAATGAACAGCCTGAGAGCCGAGGACACGGCTGTGTATTACTGTGCGAGTGATCTTGGTGC
TGGTCCTTATTATTATGGTAAGGATGTTTGGGGCCAAGGGACCACGGTCACCGTCTCAAGC
[SEQ ID NO. 73]

Figure 4H

A10 codon-optimised clone (induced modifications in the amino-acid sequence)

>A10_optimised_aa_H

QVQLVESGGGVVQPGRSLRLSCAASGFTFSSYGMHWVRQAPGKGLEWVAVISYDGSNKYYA
DSVKGRFTISRDNSKNTLYLQMNSLRAEDTAVYYCASDLGAGPYYYGKDVWGQGTTVTVSS
[SEQ ID NO. 74]

>A10_optimised_ntd_H

CAGGTGCAGCTGGTCGAATCCGGGGGGGGGTGGTGCAGCCTGGACGGTCACTGAGACTGA
GTTGTGCCGCCTCTGGGTTTACTTTCAGCTCCTATGGCATGCACTGGGTGAGGCAGGCTCC
CGGCAAGGGGCTGGAGTGGGTGGCAGTCATCTCTTACGACGGCAGTAACAAGTACTATGCC
GATAGCGTCAAAGGGCGGTTCACTATTTCAAGAGACAACAGCAAAAATACCCTGTACCTCC
AGATGAACAGCCTGCGGGCCGAAGACACAGCTGTGTACTATTGCGCATCTGATCTGGGAGC
CGGCCCTTACTATTACGGCAAGGATGTCTGGGGGCAGGGAACCACAGTCACCGTCTCAAGC
[SEQ ID NO. 75]

B6 clone

>B6_aa_H

QVQLVESGGGVVQPGRSLRLSCAASGFTFSSYGMHWVRQAPGKGLEWVAVISYDGSNKYYA
DSVKGRFTISRDNSKNTLYLQMNSLRAEDTAVYYCASDYGAGPYYYGMDVWGQGTTVTVSS
[SEQ ID NO. 15]

>B6_ntd_H

CAGGTCCAGCTGGTAGAGTCCGGGGGAGGCGTGGTCCAGCCTGGGCGGTCCCTGAGACTCT
CCTGTGCAGCCTCTGGATTCACCTTCAGTAGCTATGGCATGCACTGGGTCCGCCAGGCTCC
AGGCAAGGGGCTGGAGTGGGTGGCAGTTATATCATATGATGGAAGTAATAAATACTACGCA
GACTCCGTGAAGGGCCGATTCACCATCTCCAGAGACAATTCCAAGAACACGCTGTATCTGC
AAATGAACAGCCTGAGAGCCGAGGACACGGCTGTGTATTACTGTGCGAGTGATTATGGTGC
TGGTCCTTATTATTATGGTATGGATGTTTGGGGCCAAGGGACCACGGTCACCGTCTCAAGC
[SEQ ID NO. 76]

Figure 4I

B6 codon-optimised clone (no modifications in the amino-acid sequence)

\>B6_optimised_ntd_H

CAGGTGCAGCTGGTGGAAAGCGGGGGGGGCGTGGTGCAGCCTGGAAGGTCACTGAGACTGT
CTTGTGCCGCATCTGGGTTTACATTTAGCTCCTATGGCATGCACTGGGTGAGGCAGGCTCC
CGGCAAGGGGCTGGAGTGGGTGGCAGTCATCTCTTACGACGGCAGTAACAAGTACTATGCC
GATAGCGTCAAAGGCGGTTCACTATTTCAAGAGACAACAGCAAAAATACCCTGTACCTCC
AGATGAACAGCCTGCGGGCCGAAGACACAGCTGTGTACTATTGCGCATCTGATTACGGAGC
CGGCCCTTACTATTACGGCATGGATGTCTGGGGGCAGGGAACCACAGTCACCGTCTCAAGC
[SEQ ID NO. 77]

C4 clone

\>C4_aa_H

QVQLVESGGGVVQPGRSLRLSCAASGFTFSSYGMHWVRQAPGKGLEWVAVISYDGSNKYYA
DSVKGRFTISRDNSKNTLYLQMNSLRAEDTAVYYCASDLGAGPYYYGLDVWGQGTTVTVSS
[SEQ ID NO. 16]

\>C4_ntd_H

CAGGTCCAGCTGGTAGAGTCCGGGGGAGGCGTGGTCCAGCCTGGGCGGTCCCTGAGACTCT
CCTGTGCAGCCTCTGGATTCACCTTCAGTAGCTATGGCATGCACTGGGTCCGCCAGGCTCC
AGGCAAGGGGCTGGAGTGGGTGGCAGTTATATCATATGATGGAAGTAATAAATACTACGCA
GACTCCGTGAAGGGCCGATTCACCATCTCCAGAGACAATTCCAAGAACACGCTGTATCTGC
AAATGAACAGCCTGAGAGCCGAGGACACGGCTGTGTATTACTGTGCGAGTGATCTTGGTGC
TGGTCCTTATTATTATGGTTTGGATGTTTGGGGCCAAGGGACCACGGTCACCGTCTCAAGC
[SEQ ID NO. 78]

C4 codon-optimised clone (no modifications in the amino-acid sequence)

\>C4_optimised_ntd_H

CAGGTGCAGCTGGTGGAATCTGGGGGGGGGGTCGTGCAGCCCGGACGGTCACTGAGACTGT
CATGTGCCGCTTCAGGGTTTACTTTTAGCTCCTATGGCATGCACTGGGTGAGGCAGGCTCC
CGGCAAGGGGCTGGAGTGGGTGGCAGTCATCTCTTACGACGGCAGTAACAAGTACTATGCC
GATAGCGTCAAAGGCGGTTCACTATTTCAAGAGACAACAGCAAAAATACCCTGTACCTCC
AGATGAACAGCCTGCGGGCCGAAGACACAGCTGTGTACTATTGCGCATCTGATCTGGGAGC
CGGCCCTTACTATTACGGCCTGGATGTCTGGGGGCAGGGAACCACAGTCACCGTCTCAAGC
[SEQ ID NO. 79]

Figure 4J

D4 clone

>D4_aa_H

QVQLVESGGGVVQPGRSLRLSCAASGFTFSSYGMHWVRQAPGKGLEWVAVISYDGSNKYYA
DSVKGRFTISRDNSKNTLYLQMNSLRAEDTAVYYCASDLGAGPYYYGMDVWGQGTTVTVSS
[SEQ ID NO. 17]

>D4_ntd_H

CAGGTCCAGCTGGTAGAGTCCGGGGGAGGCGTGGTCCAGCCTGGGCGGTCCCTGAGACTCT
CCTGTGCAGCCTCTGGATTCACCTTCAGTAGCTATGGCATGCACTGGGTCCGCCAGGCTCC
AGGCAAGGGGCTGGAGTGGGTGGCAGTTATATCATATGATGGAAGTAATAAATACTACGCA
GACTCCGTGAAGGGCCGATTCACCATCTCCAGAGACAATTCCAAGAACACGCTGTATCTGC
AAATGAACAGCCTGAGAGCCGAGGACACGGCTGTGTATTACTGTGCGAGTGATCTTGGTGC
TGGTCCTTATTATTATGGTATGGATGTTTGGGGCCAAGGGACCACGGTCACCGTCTCAAGC
[SEQ ID NO. 80]

E1 clone

>E1_aa_H

QVQLVESGGGVVQPGRSLRLSCAASGFTFSSYGMHWVRQAPGKGLEWVAVISYDGSNKYYA
DSVKGRFTISRDNSKNTLYLQMNSLRAEDTAVYYCASDLGAGPYYYGMDVWGQGTTVTVSS
[SEQ ID NO. 18]

>E1_ntd_H

CAGGTCCAGCTGGTAGAGTCCGGGGGAGGCGTGGTCCAGCCTGGGCGGTCCCTGAGACTCT
CCTGTGCAGCCTCTGGATTCACCTTCAGTAGCTATGGCATGCACTGGGTCCGCCAGGCTCC
AGGCAAGGGGCTGGAGTGGGTGGCAGTTATATCATATGATGGAAGTAATAAATACTACGCA
GACTCCGTGAAGGGCCGATTCACCATCTCCAGAGACAATTCCAAGAACACGCTGTATCTGC
AAATGAACAGCCTGAGAGCCGAGGACACGGCTGTGTATTACTGTGCGAGTGATCTTGGTGC
TGGTCCTTATTATTATGGTATGGATGTTTGGGGCCAAGGGACCACGGTCACCGTCTCAAGC
[SEQ ID NO. 81]

Figure 4K

F2 clone

>F2_aa_H

QVQLVESGGGVVQPGRSLRLSCAASGFTFSSYGMHWVRQAPGKGLEWVAVISYDGSNKYYA
DSVKGRFTISRDNSKNTLYLQMNSLRAEDTAVYYCASDLGAGPYYYGMDVWGQGTTVTVSS
[SEQ ID NO. 19]

>F2_ntd_H

CAGGTCCAGCTGGTAGAGTCCGGGGGAGGCGTGGTCCAGCCTGGGCGGTCCCTGAGACTCT
CCTGTGCAGCCTCTGGATTCACCTTCAGTAGCTATGGCATGCACTGGGTCCGCCAGGCTCC
AGGCAAGGGGCTGGAGTGGGTGGCAGTTATATCATATGATGGAAGTAATAAATACTACGCA
GACTCCGTGAAGGGCCGATTCACCATCTCCAGAGACAATTCCAAGAACACGCTGTATCTGC
AAATGAACAGCCTGAGAGCCGAGGACACGGCTGTGTATTACTGTGCGAGTGATCTTGGTGC
TGGTCCTTATTATTATGGTATGGATGTTTGGGGCCAAGGGACCACGGTCACCGTCTCAAGC
[SEQ ID NO. 82]

G1 clone

>G1_aa_H

QVQLVESGGGVVQPGRSLRLSCAASGFTFSSYGMHWVRQAPGKGLEWVAVISYDGSNKYYA
DSVKGRFTISRDNSKNTLYLQMNSLRAEDTAVYYCASDLGAGPYYYGMDVWGQGTTVTVSS
[SEQ ID NO. 20]

>G1_ntd_H

CAGGTCCAGCTGGTAGAGTCCGGGGGAGGCGTGGTCCAGCCTGGGCGGTCCCTGAGACTCT
CCTGTGCAGCCTCTGGATTCACCTTCAGTAGCTATGGCATGCACTGGGTCCGCCAGGCTCC
AGGCAAGGGGCTGGAGTGGGTGGCAGTTATATCATATGATGGAAGTAATAAATACTACGCA
GACTCCGTGAAGGGCCGATTCACCATCTCCAGAGACAATTCCAAGAACACGCTGTATCTGC
AAATGAACAGCCTGAGAGCCGAGGACACGGCTGTGTATTACTGTGCGAGTGATCTTGGTGC
TGGTCCTTATTATTATGGTATGGATGTTTGGGGCCAAGGGACCACGGTCACCGTCTCAAGC
[SEQ ID NO. 83]

Figure 4L

G2 clone

>G2_aa_H

QVQLVESGGGVVQPGRSLRLSCAASGFTFSSYGMHWVRQAPGKGLEWVAVISYDGSNKYYA
DSVKGRFTISRDNSKNTLYLQMNSLRAEDTAVYYCASDLGAGPYYYGMDVWGQGTTVTVSS
[SEQ ID NO. 21]

>G2_ntd_H

CAGGTCCAGCTGGTAGAGTCCGGGGGAGGCGTGGTCCAGCCTGGGCGGTCCCTGAGACTCT
CCTGTGCAGCCTCTGGATTCACCTTCAGTAGCTATGGCATGCACTGGGTCCGCCAGGCTCC
AGGCAAGGGGCTGGAGTGGGTGGCAGTTATATCATATGATGGAAGTAATAAATACTACGCA
GACTCCGTGAAGGGCCGATTCACCATCTCCAGAGACAATTCCAAGAACACGCTGTATCTGC
AAATGAACAGCCTGAGAGCCGAGGACACGGCTGTGTATTACTGTGCGAGTGATCTTGGTGC
TGGTCCTTATTATTATGGTATGGATGTTTGGGGCCAAGGGACCACGGTCACCGTCTCAAGC
[SEQ ID NO. 84]

G10 clone

>G10_aa_H

QVQLVESGGGVVQPGRSLRLSCAASGFTFSSYGMHWVRQAPGKGLEWVAVISYDGSNKYYA
DSVKGRFTISRDNSKNTLYLQMNSLRAEDTAVYYCASDYGAGPYYYGMDVWGQGTTVTVSS
[SEQ ID NO. 22]

>G10_ntd_H

CAGGTCCAGCTGGTAGAGTCCGGGGGAGGCGTGGTCCAGCCTGGGCGGTCCCTGAGACTCT
CCTGTGCAGCCTCTGGATTCACCTTCAGTAGCTATGGCATGCACTGGGTCCGCCAGGCTCC
AGGCAAGGGGCTGGAGTGGGTGGCAGTTATATCATATGATGGAAGTAATAAATACTACGCA
GACTCCGTGAAGGGCCGATTCACCATCTCCAGAGACAATTCCAAGAACACGCTGTATCTGC
AAATGAACAGCCTGAGAGCCGAGGACACGGCTGTGTATTACTGTGCGAGTGATTATGGTGC
TGGTCCTTATTATTATGGTATGGATGTTTGGGGCCAAGGGACCACGGTCACCGTCTCAAGC
[SEQ ID NO. 85]

Figure 4M

H4 clone

>H4_aa_H

QVQLVESGGGVVQPGRSLRLSCAASGFTFSSYGMHWVRQAPGKGLEWVAVISYDGSNKYYA
DSVKGRFTISRDNSKNTLYLQMNSLRAEDTAVYYCASDLGSGYYLYGMDVWGQGTTVTVSS
[SEQ ID NO. 23]

>H4_ntd_H

CAGGTCCAGCTGGTAGAGTCCGGGGGAGGCGTGGTCCAGCCTGGGCGGTCCCTGAGACTCT
CCTGTGCAGCCTCTGGATTCACCTTCAGTAGCTATGGCATGCACTGGGTCCGCCAGGCTCC
AGGCAAGGGGCTGGAGTGGGTGGCAGTTATATCATATGATGGAAGTAATAAATACTACGCA
GACTCCGTGAAGGGCCGATTCACCATCTCCAGAGACAATTCCAAGAACACGCTGTATCTGC
AAATGAACAGCCTGAGAGCCGAGGACACGGCTGTGTATTACTGTGCGAGTGATCTTGGTTC
TGGTTATTATCTTTATGGTATGGACGTCTGGGGCCAAGGGACCACGGTCACCGTCTCAAGC
[SEQ ID NO. 86]

H4 codon-optimised clone (no modifications in the amino-acid sequence)

>H4_optimised_ntd_H

CAGGTGCAGCTGGTGGAGAGCGGGGGGGGGTGGTGCAGCCTGGACGGTCACTGAGACTGA
GTTGCGCCGCATCTGGATTCACATTTAGCTCCTACGGCATGCACTGGGTGAGGCAGGCACC
CGGCAAGGGGCTGGAGTGGGTGGCCGTCATCTCTTATGACGGCAGTAACAAGTACTATGCT
GATAGCGTCAAAGGGCGGTTCACTATTTCAAGAGACAACAGCAAAAATACCCTGTACCTCC
AGATGAATAGCCTGCGGGCCGAAGACACAGCTGTGTACTATTGCGCCTCCGATCTGGGATC
TGGCTACTATCTGTATGGCATGGATGTCTGGGGGCAGGGAACCACAGTCACCGTCTCAAGC
[SEQ ID NO. 87]

H9 clone

>H9_aa_H

QVQLVESGGGVVQPGRSLRLSCAASGFTFSSYGMHWVRQAPGKGLEWVAVISYDGSNKYYA
DSVKGRFTISRDNSKNTLYLQMNSLRAEDTAVYYCASDLGAGPYYYGMDVWGQGTTVTVSS
[SEQ ID NO. 24]

>H9_ntd_H

CAGGTCCAGCTGGTAGAGTCCGGGGGAGGCGTGGTCCAGCCTGGGCGGTCCCTGAGACTCT
CCTGTGCAGCCTCTGGATTCACCTTCAGTAGCTATGGCATGCACTGGGTCCGCCAGGCTCC
AGGCAAGGGGCTGGAGTGGGTGGCAGTTATATCATATGATGGAAGTAATAAATACTACGCA
GACTCCGTGAAGGGCCGATTCACCATCTCCAGAGACAATTCCAAGAACACGCTGTATCTGC
AAATGAACAGCCTGAGAGCCGAGGACACGGCTGTGTATTACTGTGCGAGTGATCTTGGTGC
TGGTCCTTATTATTATGGTATGGATGTTTGGGGCCAAGGGACCACGGTCACCGTCTCAAGC
[SEQ ID NO. 88]

Affinity

| | K_D (nM) |
|---|---|
| A3 | 0.20 |
| A10 | 0.08 |
| B6 | 0.26 |
| C4 | 0.40 |
| D4 | 0.22 |
| E1 | 0.21 |
| F2 | 0.11 |
| G1 | 0.10 |
| G2 | 0.10 |
| G10 | 0.27 |
| H4 | 0.27 |
| H9 | ND |
| nivolumab | 1.9 |
| lambrolizumab | 0.5 |

Figure 5

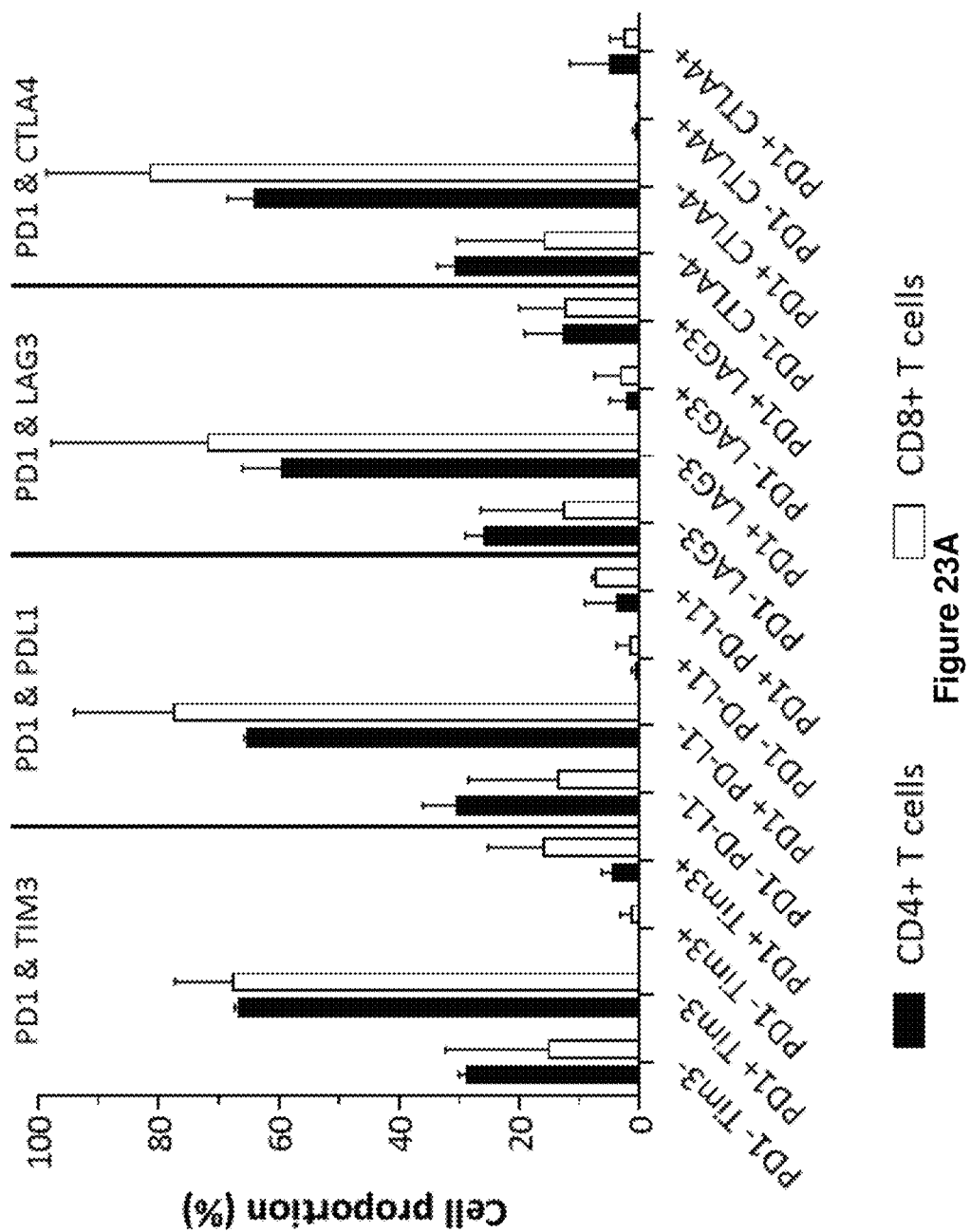

ANTI-PD-1 ANTIBODIES

RELATED APPLICATIONS

This application is a continuation of currently pending U.S. application Ser. No. 15/521,434, entitled "ANTI-PD-1 ANTIBODIES", filed Apr. 24, 2017, issued as U.S. Pat. No. 10,280,244, which application claims priority to and is a 35 U.S.C. § 371 national phase application of PCT/SG2015/050413, (WO 2016/068801), filed Oct. 27, 2015, entitled "Anti-PD-1 Antibodies". International application serial no. PCT/SG2015/050413 claims priority to GB application serial no. 1419084.7, filed Oct. 27, 2014. Each of the above-referenced applications are incorporated herein by reference in their entirety.

SEQUENCE STATEMENT

Incorporated by reference herein in its entirety is the Sequence Listing entitled "Sequence_listing", created Apr. 25, 2017, size of 60.3 kilobytes.

FIELD OF THE INVENTION

The present invention relates to antibodies that bind to programmed cell death 1 (PD-1).

BACKGROUND TO THE INVENTION

T-cell exhaustion is a state of T-cell dysfunction that arises during many chronic infections and cancer. It is defined by poor T-cell effector function, sustained expression of inhibitory receptors and a transcriptional state distinct from that of functional effector or memory T-cells. Exhaustion prevents optimal control of infection and tumors. (E John Wherry, *Nature Immunology* 12, 492-499 (2011)).

T-cell exhaustion is characterized by the stepwise and progressive loss of T-cell functions. Exhaustion is well-defined during chronic lymphocytic choriomeningitis virus infection and commonly develops under conditions of antigen-persistence, which occur following many chronic infections including hepatitis B virus, hepatitis C virus and human immunodeficiency virus infections, as well as during tumor metastasis. Exhaustion is not a uniformly disabled setting as a gradation of phenotypic and functional defects can manifest, and these cells are distinct from prototypic effector, memory and also anergic T cells. Exhausted T cells most commonly emerge during high-grade chronic infections, and the levels and duration of antigenic stimulation are critical determinants of the process. (Yi et al., *Immunology* April 2010; 129(4):474-481).

Circulating human tumor-specific $CD8^+$ T cells may be cytotoxic and produce cytokines in vivo, indicating that self- and tumor-specific human $CD8^+$ T cells can reach functional competence after potent immunotherapy such as vaccination with peptide, incomplete Freund's adjuvant (IFA), and CpG or after adoptive transfer. In contrast to peripheral blood, T-cells from metastasis are functionally deficient, with abnormally low cytokine production and upregulation of the inhibitory receptors PD-1, CTLA-4, and TIM-3. Functional deficiency is reversible, since T-cells isolated from melanoma tissue can restore IFN-γ production after short-term in vitro culture. However, it remains to be determined whether this functional impairment involves further molecular pathways, possibly resembling T-cell exhaustion or anergy as defined in animal models. (Baitsch et al., *J Clin Invest.* 2011; 121(6):2350-2360).

Programmed cell death 1 (PD-1), also called CD279, is a type I membrane protein encoded in humans by the PDCD1 gene. It has two ligands, PD-L1 and PD-L2.

The PD-1 pathway is a key immune-inhibitory mediator of T-cell exhaustion. Blockade of this pathway can lead to T-cell activation, expansion, and enhanced effector functions. As such, PD-1 negatively regulates T cell responses. PD-1 has been identified as a marker of exhausted T cells in chronic disease states, and blockade of PD-1:PD-1L interactions has been shown to partially restore T cell function. (Sakuishi et al., *JEM* Vol. 207, Sep. 27, 2010, pp 2187-2194).

Nivolumab (BMS-936558) is an anti-PD-1 antibody that was approved for the treatment of melanoma in Japan in July 2014. Other anti-PD-1 antibodies are described in WO 2010/077634, WO 2006/121168, WO2008/156712 and WO2012/135408.

T cell immunoglobulin mucin 3 (TIM-3) is an immune regulator identified as being upregulated on exhausted $CD8^+$ T cells (Sakuishi et al., *JEM* Vol. 207, Sep. 27, 2010, pp 2187-2194). TIM-3 was originally identified as being selectively expressed on IFN-γ-secreting Th1 and Tc1 cells. Interaction of TIM-3 with its ligand, galectin-9, triggers cell death in $TIM-3^+$ T cells. Anti-TIM-3 antibodies are described in Ngiow et al (Cancer Res. 2011 May 15; 71(10):3540-51), and in U.S. Pat. No. 8,552,156

Both TIM-3 and PD-1 can function as negative regulators of T cell responses and combined targeting of the TIM-3 and PD-1 pathways is more effective in controlling tumor growth than targeting either pathway alone. (Sakuishi et al., *JEM* Vol. 207, Sep. 27, 2010, pp 2187-2194; and Ngiow et al *Cancer Res.* 2011 May 15; 71(10):3540-51).

SUMMARY OF THE INVENTION

The present invention is concerned with antibodies, or antigen binding fragments, that bind to PD-1. Heavy and light chain polypeptides are also disclosed. The antibodies, antigen binding fragments and polypeptides may be provided in isolated and/or purified form and may be formulated into compositions suitable for use in research, therapy and diagnosis.

In some embodiments the antibody, or antigen binding fragment, or polypeptide may be effective to restore T-cell function in T-cells, e.g. $CD8^+$ T-cells, exhibiting T-cell exhaustion or T-cell anergy.

In one aspect of the present invention an antibody, or antigen binding fragment, is provided, the amino acid sequence of the antibody may comprise the amino acid sequences i) to iii), or the amino acid sequences iv) to vi), or preferably the amino acid sequences i) to vi):

```
i) LC-CDR1:
                                    (SEQ ID NO: 25)
   SGSSSNIKFNSVN ii) LC-CDR2:
                                    (SEQ ID NO: 26)
   SNNQRPS iii) LC-CDR3:
                                    (SEQ ID NO: 53)
   X₁X₂WDDX₃X₄X₅GX₆X₇ iv) HC-CDR1:
                                    (SEQ ID NO: 39)
   GFTFSSYGMH
   or
```

HC-CDR1:
(SEQ ID NO: 89)
SYGMH v) HC-CDR2:
(SEQ ID NO: 40)
VISYDGSNKYYADSVKG vi) HC-CDR3:
(SEQ ID NO: 54)
DZ₁GZ₂GZ₃YZ₄YGZ₅DZ₆ or a variant thereof in which one or two or three amino acids in one or more of the sequences (i) to (vi) are replaced with another amino acid, where $X_1$=A or S, $X_2$=S or A, $X_3$=V, Y, F, D, S or A, $X_4$=L, Y, V or A, $X_5$=Y, R or H, $X_6$=S, or T, $X_7$=V, I, or M and $Z_1$=L or Y, $Z_2$=A or S, $Z_3$=P or Y, $Z_4$=Y or L, $Z_5$=K, M or L, $Z_6$=H or V.

In connection with all aspects of the present invention, in embodiments wherein HC-CDR1: SYGMH (SEQ ID NO:89), this sequence may be comprised in the larger sequence GFTFSSYGMH (SEQ ID NO:39).

In some embodiments, LC-CDR3 is one of ASWDDVLYGSV (SEQ ID NO:27), ASWDDYYYGTI (SEQ ID NO:28), ASWDDYLRGTV (SEQ ID NO:29), SAWDDYLHGTV (SEQ ID NO:30), ASWDDYVRGTM (SEQ ID NO:31), SSWDDFLRGTV (SEQ ID NO:32), SSWDDDARGTI (SEQ ID NO:33), AAWDDVYYGTI (SEQ ID NO:34), ASWDDSLYGTV (SEQ ID NO:35), AAWDDAYYGTI (SEQ ID NO:36), ASWDDVYRGTV (SEQ ID NO:37), or SSWDDSLYGTI (SEQ ID NO:38). In some embodiments HC-CDR3 is one of DLGAGPYYYGKDH (SEQ ID NO:41), DLGAGPYYYGKDV (SEQ ID NO:42), DYGAGPYYYGMDV (SEQ ID NO:43), DLGAGPYYYGLDV (SEQ ID NO:44), DLGAGPYYYGMDV (SEQ ID NO:45), DLGAGPYYYGMDV (SEQ ID NO:46), DLGAGPYYYGMDV (SEQ ID NO:47), DLGAGPYYYGMDV (SEQ ID NO:48), DLGAGPYYYGMDV (SEQ ID NO:49), DYGAGPYYYGMDV (SEQ ID NO:50), DLGSGYYLYGMDV (SEQ ID NO:51), or DLGAGPYYYGMDV (SEQ ID NO:52).

In some embodiments the antibody, or antigen binding fragment, may comprise at least one light chain variable region incorporating the following CDRs:

```
                              (SEQ ID NO: 25)
LC-CDR1:
SGSSSNIKFNSVN

LC-CDR2:                      (SEQ ID NO: 26)
SNNQRPS

LC-CDR3:                      (SEQ ID NO: 27)
ASWDDVLYGSV
```

In some embodiments the antibody, or antigen binding fragment, may comprise at least one light chain variable region incorporating the following CDRs:

```
                              (SEQ ID NO: 25)
LC-CDR1: SGSSSNIKFNSVN (SEQ ID NO: 26)
LC-CDR2: SNNQRPS (SEQ ID NO: 28)
LC-CDR3: ASWDDYYYGTI
```

In some embodiments the antibody, or antigen binding fragment, may comprise at least one light chain variable region incorporating the following CDRs:

```
                              (SEQ ID NO: 25)
LC-CDR1: SGSSSNIKFNSVN (SEQ ID NO: 26)
LC-CDR2: SNNQRPS (SEQ ID NO: 29)
LC-CDR3: ASWDDYLRGTV
```

In some embodiments the antibody, or antigen binding fragment, may comprise at least one light chain variable region incorporating the following CDRs:

```
                              (SEQ ID NO: 25)
LC-CDR1: SGSSSNIKFNSVN (SEQ ID NO: 26)
LC-CDR2: SNNQRPS (SEQ ID NO: 30)
LC-CDR3: SAWDDYLHGTV
```

In some embodiments the antibody, or antigen binding fragment, may comprise at least one light chain variable region incorporating the following CDRs:

```
                              (SEQ ID NO: 25)
LC-CDR1: SGSSSNIKFNSVN (SEQ ID NO: 26)
LC-CDR2: SNNQRPS (SEQ ID NO: 31)
LC-CDR3: ASWDDYVRGTM
```

In some embodiments the antibody, or antigen binding fragment, may comprise at least one light chain variable region incorporating the following CDRs:

```
                              (SEQ ID NO: 25)
LC-CDR1: SGSSSNIKFNSVN (SEQ ID NO: 26)
LC-CDR2: SNNQRPS (SEQ ID NO: 32)
LC-CDR3: SSWDDFLRGTV
```

In some embodiments the antibody, or antigen binding fragment, may comprise at least one light chain variable region incorporating the following CDRs:

```
                              (SEQ ID NO: 25)
LC-CDR1: SGSSSNIKFNSVN (SEQ ID NO: 26)
LC-CDR2: SNNQRPS
```

-continued

```
                                   (SEQ ID NO: 33)
LC-CDR3: SSWDDDARGTI
```

In some embodiments the antibody, or antigen binding fragment, may comprise at least one light chain variable region incorporating the following CDRs:

```
                                   (SEQ ID NO: 25)
LC-CDR1: SGSSSNIKFNSVN (SEQ ID NO: 26)
LC-CDR2: SNNQRPS (SEQ ID NO: 34)
LC-CDR3: AAWDDVYYGTI
```

In some embodiments the antibody, or antigen binding fragment, may comprise at least one light chain variable region incorporating the following CDRs:

```
                                   (SEQ ID NO: 25)
LC-CDR1: SGSSSNIKFNSVN (SEQ ID NO: 26)
LC-CDR2: SNNQRPS (SEQ ID NO: 35)
LC-CDR3: ASWDDSLYGTV
```

In some embodiments the antibody, or antigen binding fragment, may comprise at least one light chain variable region incorporating the following CDRs:

```
                                   (SEQ ID NO: 25)
LC-CDR1: SGSSSNIKFNSVN (SEQ ID NO: 26)
LC-CDR2: SNNQRPS (SEQ ID NO: 36)
LC-CDR3: AAWDDAYYGTI
```

In some embodiments the antibody, or antigen binding fragment, may comprise at least one light chain variable region incorporating the following CDRs:

```
                                   (SEQ ID NO: 25)
LC-CDR1: SGSSSNIKFNSVN (SEQ ID NO: 26)
LC-CDR2: SNNQRPS (SEQ ID NO: 37)
LC-CDR3: ASWDDVYRGTV
```

In some embodiments the antibody, or antigen binding fragment, may comprise at least one light chain variable region incorporating the following CDRs:

```
                                   (SEQ ID NO: 25)
LC-CDR1: SGSSSNIKFNSVN (SEQ ID NO: 26)
LC-CDR2: SNNQRPS (SEQ ID NO: 38)
LC-CDR3: SSWDDSLYGTI
```

In some embodiments the antibody, or antigen binding fragment, may comprise at least one heavy chain variable region incorporating the following CDRs:

```
                                   (SEQ ID NO: 39)
HC-CDR1: GFTFSSYGMH
or
                                   (SEQ ID NO: 89)
SYGMH (SEQ ID NO: 40)
HC-CDR2: VISYDGSNKYYADSVKG (SEQ ID NO: 41)
HC-CDR3: DLGAGPYYYGKDH
```

In some embodiments the antibody, or antigen binding fragment, may comprise at least one heavy chain variable region incorporating the following CDRs:

```
                                   (SEQ ID NO: 39)
HC-CDR1: GFTFSSYGMH
or
                                   (SEQ ID NO: 89)
SYGMH (SEQ ID NO: 40)
HC-CDR2: VISYDGSNKYYADSVKG (SEQ ID NO: 42)
HC-CDR3: DLGAGPYYYGKDV
```

In some embodiments the antibody, or antigen binding fragment, may comprise at least one heavy chain variable region incorporating the following CDRs:

```
                                   (SEQ ID NO: 39)
HC-CDR1: GFTFSSYGMH
or
                                   (SEQ ID NO: 89)
SYGMH (SEQ ID NO: 40)
HC-CDR2: VISYDGSNKYYADSVKG (SEQ ID NO: 43)
HC-CDR3: DYGAGPYYYGMDV
```

In some embodiments the antibody, or antigen binding fragment, may comprise at least one heavy chain variable region incorporating the following CDRs:

```
                                   (SEQ ID NO: 39)
HC-CDR1: GFTFSSYGMH
or
                                   (SEQ ID NO: 89)
SYGMH (SEQ ID NO: 40)
HC-CDR2: VISYDGSNKYYADSVKG (SEQ ID NO: 44)
HC-CDR3: DLGAGPYYYGLDV
```

In some embodiments the antibody, or antigen binding fragment, may comprise at least one heavy chain variable region incorporating the following CDRs:

```
                                   (SEQ ID NO: 39)
HC-CDR1: GFTFSSYGMH
or
                                   (SEQ ID NO: 89)
SYGMH (SEQ ID NO: 40)
HC-CDR2: VISYDGSNKYYADSVKG
```

-continued

```
                                    (SEQ ID NO: 45)
HC-CDR3: DLGAGPYYYGMDV
```

In some embodiments the antibody, or antigen binding fragment, may comprise at least one heavy chain variable region incorporating the following CDRs:

```
                                    (SEQ ID NO: 39)
HC-CDR1: GFTFSSYGMH
or
                                    (SEQ ID NO: 89)
SYGMH
                                    (SEQ ID NO: 40)
HC-CDR2: VISYDGSNKYYADSVKG
                                    (SEQ ID NO: 46)
HC-CDR3: DLGAGPYYYGMDV
```

In some embodiments the antibody, or antigen binding fragment, may comprise at least one heavy chain variable region incorporating the following CDRs:

```
                                    (SEQ ID NO: 39)
HC-CDR1: GFTFSSYGMH
or
                                    (SEQ ID NO: 89)
SYGMH
                                    (SEQ ID NO: 40)
HC-CDR2: VISYDGSNKYYADSVKG
                                    (SEQ ID NO: 47)
HC-CDR3: DLGAGPYYYGMDV
```

In some embodiments the antibody, or antigen binding fragment, may comprise at least one heavy chain variable region incorporating the following CDRs:

```
                                    (SEQ ID NO: 39)
HC-CDR1: GFTFSSYGMH
or
                                    (SEQ ID NO: 89)
SYGMH
                                    (SEQ ID NO: 40)
HC-CDR2: VISYDGSNKYYADSVKG
                                    (SEQ ID NO: 48)
HC-CDR3: DLGAGPYYYGMDV
```

In some embodiments the antibody, or antigen binding fragment, may comprise at least one heavy chain variable region incorporating the following CDRs:

```
                                    (SEQ ID NO: 39)
HC-CDR1: GFTFSSYGMH
or
                                    (SEQ ID NO: 89)
SYGMH
                                    (SEQ ID NO: 40)
HC-CDR2: VISYDGSNKYYADSVKG
                                    (SEQ ID NO: 49)
HC-CDR3: DLGAGPYYYGMDV
```

In some embodiments the antibody, or antigen binding fragment, may comprise at least one heavy chain variable region incorporating the following CDRs:

```
                                    (SEQ ID NO: 39)
HC-CDR1: GFTFSSYGMH
or
                                    (SEQ ID NO: 89)
SYGMH
                                    (SEQ ID NO: 40)
HC-CDR2: VISYDGSNKYYADSVKG
                                    (SEQ ID NO: 50)
HC-CDR3: DYGAGPYYYGMDV
```

In some embodiments the antibody, or antigen binding fragment, may comprise at least one heavy chain variable region incorporating the following CDRs:

```
                                    (SEQ ID NO: 39)
HC-CDR1: GFTFSSYGMH
or
                                    (SEQ ID NO: 89)
SYGMH
                                    (SEQ ID NO: 40)
HC-CDR2: VISYDGSNKYYADSVKG
                                    (SEQ ID NO: 51)
HC-CDR3: DLGSGYYLYGMDV
```

In some embodiments the antibody, or antigen binding fragment, may comprise at least one heavy chain variable region incorporating the following CDRs:

```
                                    (SEQ ID NO: 39)
HC-CDR1: GFTFSSYGMH
or
                                    (SEQ ID NO: 89)
SYGMH
                                    (SEQ ID NO: 40)
HC-CDR2: VISYDGSNKYYADSVKG
                                    (SEQ ID NO: 52)
HC-CDR3: DLGAGPYYYGMDV
```

The antibody may comprise at least one light chain variable region incorporating the CDRs shown in FIG. 1 or 3. The antibody may comprise at least one heavy chain variable region incorporating the CDRs shown in FIG. 2 or 3.

The antibody may comprise at least one light chain variable region ($V_L$) comprising the amino acid sequence of one of SEQ ID NOs 1, 25, 26, 27 or 2, 25, 26, 28, or 3, 25, 26, 29 or 4, 25, 26, 30, or 5, 25, 26, 31 or 6, 25, 26, 32 or 7, 25, 26, 33 or 8, 25, 26, 34 or 9, 25, 26, 35 or 10, 25, 26 36 or 11, 25, 26, 37 or 12, 25, 26, 38, or one of the amino acid sequences shown in FIG. 1 or an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to one of SEQ ID NOs 1, 25, 26, 27 or 2, 25, 26, 28, or 3, 25, 26, 29 or 4, 25, 26, 30, or 5, 25, 26, 31 or 6, 25, 26, 32 or 7, 25, 26, 33 or 8, 25, 26, 34 or 9, 25, 26, 35 or 10, 25, 26 36 or 11, 25, 26, 37 or 12, 25, 26, 38, or to the amino acid sequence of the $V_L$ chain amino acid sequence shown in FIG. 1.

The antibody may comprise at least one heavy chain variable region (V$_H$) comprising the amino acid sequence of one of SEQ ID NOs 13, 39 or 89, 40, 41 or 14, 39 or 89, 40, 42, or 15, 39 or 89, 40, 43 or 16, 39 or 89, 40, 44 or 17, 39 or 89, 40, 45 or 18, 39 or 89, 40, 46 or 19, 39 or 89, 40, 47 or 20, 39 or 89, 40, 48 or 21, 39 or 89, 40, 49 or 22, 39 or 89, 40, 50 or 23, 39 or 89, 40, 51 or 24, 39 or 89, 40, 52, or one of the amino acid sequences shown in FIG. 2 or an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to one of SEQ ID NOs 13, 39, 40, 41 or 14, 39 or 89, 40, 42, or 15, 39 or 89, 40, 43 or 16, 39 or 89, 40, 44 or 17, 39 or 89, 40, 45 or 18, 39 or 89, 40, 46 or 19, 39 or 89, 40, 47 or 20, 39 or 89, 40, 48 or 21, 39 or 89, 40, 49 or 22, 39 or 89, 40, 50 or 23, 39 or 89, 40, 51 or 24, 39 or 89, 40, 52, or to the amino acid sequence of the V$_H$ chain amino acid sequence shown in FIG. 2.

The antibody may comprise at least one light chain variable region comprising the amino acid sequence of one of SEQ ID NOs 1, 25, 26, 27 or 2, 25, 26, 28, or 3, 25, 26, 29 or 4, 25, 26, 30, or 5, 25, 26, 31 or 6, 25, 26, 32 or 7, 25, 26, 33 or 8, 25, 26, 34 or 9, 25, 26, 35 or 10, 25, 26 36 or 11, 25, 26, 37 or 12, 25, 26, 38, or to one of the amino acid sequences shown in FIG. 1 (or an amino acid sequence having at least 70%, more preferably one of at least 75%, 80%, 85%, 90%, 95%, 96%, 97%, 98%, 99% or 100%, sequence identity to one of SEQ ID NOs 1, 25, 26, 27 or 2, 25, 26, 28, or 3, 25, 26, 29 or 4, 25, 26, 30, or 5, 25, 26, 31 or 6, 25, 26, 32 or 7, 25, 26, 33 or 8, 25, 26, 34 or 9, 25, 26, 35 or 10, 25, 26 36 or 11, 25, 26, 37 or 12, 25, 26, 38, or to to one of the amino acid sequences of the V$_L$ chain amino acid sequence shown in FIG. 1) and at least one heavy chain variable region comprising the amino acid sequence of one of SEQ ID NOs 13, 39 or 89, 40, 41 or 14, 39 or 89, 40, 42, or 15, 39 or 89, 40, 43 or 16, 39 or 89, 40, 44 or 17, 39 or 89, 40, 45 or 18, 39 or 89, 40, 46 or 19, 39 or 89, 40, 47 or 20, 39 or 89, 40, 48 or 21, 39 or 89, 40, 49 or 22, 39 or 89, 40, 50 or 23, 39 or 89, 40, 51 or 24, 39 or 89, 40, 52, or one of the amino acid sequence shown in FIG. 2 (or an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to one of SEQ ID NOs 13, 39 or 89, 40, 41 or 14, 39 or 89, 40, 42, or 15, 39 or 89, 40, 43 or 16, 39 or 89, 40, 44 or 17, 39 or 89, 40, 45 or 18, 39 or 89, 40, 46 or 19, 39 or 89, 40, 47 or 20, 39 or 89, 40, 48 or 21, 39 or 89, 40, 49 or 22, 39 or 89, 40, 50 or 23, 39 or 89, 40, 51 or 24, 39 or 89, 40, 52, or to one of the amino acid sequences of the V$_H$ chain amino acid sequence shown in FIG. 2).

The antibody may optionally bind PD-1. The antibody may optionally have amino acid sequence components as described above. The antibody may be an IgG. In one embodiment an in vitro complex, optionally isolated, comprising an antibody, or antigen binding fragment, as described herein, bound to PD-1 is provided.

In one aspect of the present invention an isolated heavy chain variable region polypeptide is provided, the heavy chain variable region polypeptide comprising the following CDRs:

```
HC-CDR1: GFTFSSYGMH                    (SEQ ID NO: 39)
or

SYGMH                                   (SEQ ID NO: 89)

HC-CDR2: VISYDGSNKYYADSVKG              (SEQ ID NO: 40)

HC-CDR3: DZ₁GZ₂GZ₃YZ₄YGZ₅DZ₆           (SEQ ID NO: 54)
``` where $Z_1$=L or Y, $Z_2$=A or S, $Z_3$=P or Y, $Z_4$=Y or L, $Z_5$=K, M or L, $Z_6$=H or V.

In some embodiments HC-CDR3 is one of DLGAGPYYYGKDH (SEQ ID NO:41), DLGAGPYYYGKDV (SEQ ID NO:42), DYGAGPYYYGMDV (SEQ ID NO:43), DLGAGPYYYGLDV (SEQ ID NO:44), DLGAGPYYYGMDV (SEQ ID NO:45), DLGAGPYYYGMDV (SEQ ID NO:46), DLGAGPYYYGMDV (SEQ ID NO:47), DLGAGPYYYGMDV (SEQ ID NO:48), DLGAGPYYYGMDV (SEQ ID NO:49), DYGAGPYYYGMDV (SEQ ID NO:50), DLGSGYYLYGMDV (SEQ ID NO:51), or DLGAGPYYYGMDV (SEQ ID NO:52).

In one aspect of the present invention an antibody, or antigen binding fragment, is provided, the antibody, or antigen binding fragment, comprising a heavy chain and a light chain variable region sequence, wherein:

the heavy chain comprises a HC-CDR1, HC-CDR2, HC-CDR3, having at least 85% overall sequence identity to

```
HC-CDR1: GFTFSSYGMH                    (SEQ ID NO: 39)
or

SYGMH,                                  (SEQ ID NO: 89)

HC-CDR2 VISYDGSNKYYADSVKG,              (SEQ ID NO: 40)

HC-CDR3: is one of DZ₁GZ₂GZ₃YZ₄YGZ₅DZ₆, (SEQ ID NO: 54)

DLGAGPYYYGKDH,                          (SEQ ID NO: 41)

DLGAGPYYYGKDV,                          (SEQ ID NO: 42)

DYGAGPYYYGMDV,                          (SEQ ID NO: 43)

DLGAGPYYYGLDV,                          (SEQ ID NO: 44)

DLGAGPYYYGMDV,                          (SEQ ID NO: 45)

DLGAGPYYYGMDV,                          (SEQ ID NO: 46)

DLGAGPYYYGMDV,                          (SEQ ID NO: 47)

DLGAGPYYYGMDV,                          (SEQ ID NO: 48)

DLGAGPYYYGMDV,                          (SEQ ID NO: 49)
```

DYGAGPYYYGMDV, (SEQ ID NO: 50)

DLGSGYYLYGMDV, (SEQ ID NO: 51)
or

DLGAGPYYYGMDV (SEQ ID NO: 52)

respectively, where $Z_1$=L or Y, $Z_2$=A or S, $Z_3$=P or Y, $Z_4$=Y or L, $Z_5$=K, M or L, $Z_6$=H or V, and the light chain comprises a LC-CDR1, LC-CDR2, LC-CDR3, having at least 85% overall sequence identity to

LC-CDR1: SGSSSNIKFNSVN, (SEQ ID NO: 25)

LC-CDR2: SNNQRPS, (SEQ ID NO: 26)

LC-CDR3: is one of $X_1X_2WDDX_3X_4X_5GX_6X_7$, (SEQ ID NO: 53)

ASWDDVLYGSV, (SEQ ID NO: 27)

ASWDDYYYGTI, (SEQ ID NO: 28)

ASWDDYLRGTV, (SEQ ID NO: 29)

SAWDDYLHGTV, (SEQ ID NO: 30)

ASWDDYVRGTM, (SEQ ID NO: 31)

SSWDDFLRGTV, (SEQ ID NO: 32)

SSWDDDARGTI, (SEQ ID NO: 33)

AAWDDVYYGTI, (SEQ ID NO: 34)

ASWDDSLYGTV, (SEQ ID NO: 35)

AAWDDAYYGTI, (SEQ ID NO: 36)

ASWDDVYRGTV, (SEQ ID NO: 37)
or

SSWDDSLYGTI (SEQ ID NO: 38)

respectively, where $X_1$=A or S, $X_2$=S or A, $X_3$=V, Y, F, D, S or A, $X_4$=L, Y, V or A, $X_5$=Y, R or H, $X_6$=S, or T, $X_7$=V, I, or M.

In some embodiments the degree of sequence identity may be one of 86%, 87%, 88%, 89%, 90%, 91%, 92%, 93%, 94%, 95%, 96%, 97%, 98%, 99%, or 100%.

In another aspect of the present invention an antibody, or antigen binding fragment, optionally isolated, is provided comprising a heavy chain and a light chain variable region sequence, wherein:

the heavy chain sequence has at least 85% sequence identity to the heavy chain sequence of one of SEQ ID NOs:13 to 24 (FIG. 2), and the light chain sequence has at least 85% sequence identity to the light chain sequence of one of: SEQ ID NOs:1 to 12 (FIG. 1).

In some embodiments the degree of sequence identity may be one of 86%, 87%, 88%, 89%, 90%, 91%, 92%, 93%, 94%, 95%, 96%, 97%, 98%, 99%, or 100%.

In some embodiments the antibody, antigen binding fragment, or polypeptide further comprises variable region heavy chain framework sequences between the CDRs according to the arrangement HCFR1:HC-CDR1:HCFR2: HC-CDR2:HCFR3:HC-CDR3:HCFR4. The framework sequences may be derived from human consensus framework sequences.

In one aspect of the present invention an isolated light chain variable region polypeptide, optionally in combination with a heavy chain variable region polypeptide as described herein, is provided, the light chain variable region polypeptide comprising the following CDRs:

LC-CDR1: SGSSSNIKFNSVN (SEQ ID NO: 25)

LC-CDR2: SNNQRPS (SEQ ID NO: 26)

LC-CDR3: $X_1X_2WDDX_3X_4X_5GX_6X_7$ (SEQ ID NO: 53)

where $X_1$=A or S, $X_2$=S or A, $X_3$=V, Y, F, D, S or A, $X_4$=L, Y, V or A, $X_5$=Y, R or H, $X_6$=S, or T, $X_7$=V, I, or M.

In some embodiments LC-CDR3 is one of ASWDDVLYGSV (SEQ ID NO:27), ASWDDYYYGTI (SEQ ID NO:28), ASWDDYLRGTV (SEQ ID NO:29), SAWDDYLHGTV (SEQ ID NO:30), ASWDDYVRGTM (SEQ ID NO:31), SSWDDFLRGTV (SEQ ID NO:32), SSWDDDARGTI (SEQ ID NO:33), AAWDDVYYGTI (SEQ ID NO:34), ASWDDSLYGTV (SEQ ID NO:35), AAWDDAYYGTI (SEQ ID NO:36), ASWDDVYRGTV (SEQ ID NO:37), or SSWDDSLYGTI (SEQ ID NO:38).

In some embodiments the antibody, antigen binding fragment, or polypeptide further comprises variable region light chain framework sequences between the CDRs according to the arrangement LCFR1:LC-CDR1:LCFR2:LC-CDR2: LCFR3:LC-CDR3:LCFR4. The framework sequences may be derived from human consensus framework sequences.

In some embodiments, the antibody, or antibody binding fragment, may further comprise a human constant region. For example selected from one of IgG1, IgG2, IgG3 and IgG4.

In some embodiments, the antibody, or antibody binding fragment, may further comprise a murine constant region. For example, selected from one of IgG1, IgG2A, IgG2B and IgG3.

In another aspect of the present invention, an antibody or antigen binding fragment is provided, optionally isolated, which is capable of binding to PD-1, and which is a bispecific antibody or a bispecific antigen binding fragment. In some embodiments, the bispecific antibody or bispecific antigen binding fragment comprises an antigen binding fragment or polypeptide capable of binding to PD-1 as described herein, and additionally comprises an antigen binding domain which is capable of binding to another target protein, e.g. a target protein other than PD-1. In some embodiments, the target protein is a cell surface receptor. In some embodiments, the target protein is a cell surface receptor expressed on the cell surface of immune cells, e.g. T cells. In some embodiments, the target protein may be a member of the CD28 family. In some embodiments, the member of the CD28 family is selected from TIM-3, LAG3, ICOS, CTLA4, BTLA or CD28.

In another aspect of the present invention, a composition, e.g. a pharmaceutical composition or medicament, is provided. The composition may comprise an antibody, antigen binding fragment, or polypeptide as described herein and at least one pharmaceutically-acceptable carrier, excipient, adjuvant or diluent.

In another aspect of the present invention an isolated nucleic acid encoding an antibody, antigen binding fragment, or polypeptide as described herein is provided. The nucleic acid may have a sequence of one of SEQ ID NOs 55, 56, 58, 59, 60, 61, 62, 63, 64, 65, 66, 67, 68, 69, 70, 71, 72, 73, 75, 76, 77, 78, 79, 80, 81, 82, 83, 84, 85, 86, 87, or 88 (FIG. 4), or a coding sequence which is degenerate as a result of the genetic code, or may have a nucleotide sequence having at least 70% identity thereto, optionally one of 75%, 80%, 85%, 86%, 87%, 88%, 89%, 90%, 91%, 92%, 93%, 94%, 95%, 96%, 97%, 98%, 99%, or 100%.

In one aspect of the present invention there is provided a vector comprising a nucleic acid described herein. In another aspect of the present invention, there is provided a host cell comprising the vector. For example, the host cell may be eukaryotic, or mammalian, e.g. Chinese Hamster Ovary (CHO), or human or may be a prokaryotic cell, e.g. *E. coli*. In one aspect of the present invention a method for making an antibody, or antigen binding fragment or polypeptide as described herein is provided, the method comprising culturing a host cell as described herein under conditions suitable for the expression of a vector encoding the antibody, or antigen binding fragment or polypeptide, and recovering the antibody, or antigen binding fragment or polypeptide.

In another aspect of the present invention an antibody, antigen binding fragment or polypeptide is provided for use in therapy, or in a method of medical treatment. In another aspect of the present invention an antibody, antigen binding fragment or polypeptide as described herein is provided for use in the treatment of a T-cell dysfunctional disorder. In another aspect of the present invention, the use of an antibody, antigen binding fragment or polypeptide as described herein in the manufacture of a medicament or pharmaceutical composition for use in the treatment of a T-cell dysfunctional disorder is provided.

In another aspect of the present invention a method of enhancing T-cell function comprising administering an antibody, antigen binding fragment or polypeptide as described herein to a dysfunctional T-cell is provided. The method may be performed in vitro or in vivo.

In another aspect of the present invention a method of treating a T-cell dysfunctional disorder is provided, the method comprising administering an antibody, antigen binding fragment or polypeptide as described herein to a patient suffering from a T-cell dysfunctional disorder.

In another aspect of the present invention a method of modulating an immune response in a subject is provided, the method comprising administering to the subject an antibody, antigen binding fragment or polypeptide as described herein such that the immune response in the subject is modulated.

In another aspect of the present invention a method of inhibiting growth of tumor cells in a subject is provided, the method comprising administering to the subject a therapeutically effective amount of an antibody, antigen binding fragment or polypeptide as described herein.

In another aspect of the present invention a method is provided, the method comprising contacting a sample containing, or suspected to contain, PD-1 with an antibody or antigen binding fragment, as described herein, and detecting the formation of a complex of antibody, or antigen binding fragment, and PD-1.

In another aspect of the present invention a method of diagnosing a disease or condition in a subject is provided, the method comprising contacting, in vitro, a sample from the subject with an antibody, or antigen binding fragment, as described herein, and detecting the formation of a complex of antibody, or antigen binding fragment, and PD-1.

In a further aspect of the present invention a method of selecting or stratifying a subject for treatment with PD-1 targeted agents is provided, the method comprising contacting, in vitro, a sample from the subject with an antibody, or antigen binding fragment, according to the present invention and detecting the formation of a complex of antibody, or antigen binding fragment, and PD-1.

In a further aspect of the present invention the use of an antibody, or antigen binding fragment, as described herein, for the detection of PD-1 in vitro is provided. In another aspect of the present invention the use of an antibody, or antigen binding fragment, as described herein, as an in vitro diagnostic agent is provided.

In a further aspect of the present invention a method for expanding a population of T cells is provided, wherein T cells are contacted in vitro or ex vivo with an antibody, antigen binding fragment or polypeptide according to the present invention.

In a further aspect of the present invention a method of treatment of a subject having a T-cell dysfunctional disorder is provided, the method comprising culturing T cells obtained from a blood sample from a subject in the presence of an antibody, antigen binding fragment or polypeptide according to the present invention so as to expand the T cell population, collecting expanded T cells, and administering the expanded T cells to a subject in need of treatment.

In methods of the present invention the antibody, antigen binding fragment or polypeptide may be provided as a composition as described herein.

In some embodiments the antibody may be antibody clone A3, A10, B6, C4, D4, E1, F2, G1, G2, G10, H4, or H9 as described herein.

DESCRIPTION

Antibodies

Antibodies according to the present invention preferably bind to PD-1 (the antigen), preferably human or rhesus PD-1, optionally with a $K_D$ in the range 0.1 to 2 nM.

In any aspect of the present invention the antibody preferably specifically binds PD-1 (e.g. human or rhesus) over other members of the CD28 family (preferably from the same organism), such as one or more or each of TIM-3 (HAVCR2), LAG3 (CD223), ICOS (CD278), CTLA4 (CD152), BTLA (CD272) or CD28.

Antibodies according to the present invention may be provided in isolated form.

Antibodies according to the present invention may exhibit least one of the following properties:
  a) binds to human PD-1 with a $K_D$ of 1 µM or less, preferably one of ≤10 nM, ≤1 nM, ≤800 pM, ≤700 pM, ≤600 pM, ≤500 pM, ≤400 pM, ≤300 pM, ≤200 pM or ≤100 pM;
  b) does not substantially bind to human TIM-3, LAG3, ICOS, CTLA4, BTLA or CD28;
  c) increases T-cell proliferation in an Mixed Lymphocyte Reaction (MLR) assay (e.g. see Bromelow et al *J. Immunol Methods*, 2001 Jan. 1; 247(1-2):1-8);

d) increases interferon-gamma production in an MLR assay; or e) increases interleukin-2 (IL-2) secretion in an MLR assay.

In some embodiments, the antibodies may be capable of increasing interferon-gamma production in an MLR assay in a dose-dependent manner. In some embodiments, the antibodies may be capable of increasing interferon-gamma production in an MLR assay by lymphocytes expressing one or more markers of exhaustion, e.g. PD-1.

By "antibody" we include a fragment or derivative thereof, or a synthetic antibody or synthetic antibody fragment.

In view of today's techniques in relation to monoclonal antibody technology, antibodies can be prepared to most antigens. The antigen-binding portion may be a part of an antibody (for example a Fab fragment) or a synthetic antibody fragment (for example a single chain Fv fragment [ScFv]). Suitable monoclonal antibodies to selected antigens may be prepared by known techniques, for example those disclosed in "Monoclonal Antibodies: A manual of techniques", H Zola (CRC Press, 1988) and in "Monoclonal Hybridoma Antibodies: Techniques and Applications", J G R Hurrell (CRC Press, 1982). Chimaeric antibodies are discussed by Neuberger et al (1988, 8th International Biotechnology Symposium Part 2, 792-799).

Monoclonal antibodies (mAbs) are useful in the methods of the invention and are a homogenous population of antibodies specifically targeting a single epitope on an antigen.

Polyclonal antibodies are useful in the methods of the invention. Monospecific polyclonal antibodies are preferred. Suitable polyclonal antibodies can be prepared using methods well known in the art.

Antigen binding fragments of antibodies, such as Fab and Fab$_2$ fragments may also be used/provided as can genetically engineered antibodies and antibody fragments. The variable heavy ($V_H$) and variable light ($V_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parented antibody (Morrison et al (1984) Proc. Natl. Acad. Sd. USA 81, 6851-6855).

That antigenic specificity is conferred by variable domains and is independent of the constant domains is known from experiments involving the bacterial expression of antibody fragments, all containing one or more variable domains. These molecules include Fab-like molecules (Better et al (1988) Science 240, 1041); Fv molecules (Skerra et al (1988) Science 240, 1038); single-chain Fv (ScFv) molecules where the $V_H$ and $V_L$ partner domains are linked via a flexible oligopeptide (Bird et al (1988) Science 242, 423; Huston et al (1988) Proc. Natl. Acad. Sd. USA 85, 5879) and single domain antibodies (dAbs) comprising isolated V domains (Ward et al (1989) Nature 341, 544). A general review of the techniques involved in the synthesis of antibody fragments which retain their specific binding sites is to be found in Winter & Milstein (1991) Nature 349, 293-299.

By "ScFv molecules" we mean molecules wherein the $V_H$ and $V_L$ partner domains are covalently linked, e.g. by a flexible oligopeptide.

Fab, Fv, ScFv and dAb antibody fragments can all be expressed in and secreted from E. coli, thus allowing the facile production of large amounts of the said fragments.

Whole antibodies, and F(ab')$_2$ fragments are "bivalent". By "bivalent" we mean that the said antibodies and F(ab')$_2$ fragments have two antigen combining sites. In contrast, Fab, Fv, ScFv and dAb fragments are monovalent, having only one antigen combining site. Synthetic antibodies which bind to PD-1 may also be made using phage display technology as is well known in the art.

The present application also provides an antibody or antigen binding fragment which is capable of binding to PD-1, and which is a bispecific antibody or a bispecific antigen binding fragment. In some embodiments, the bispecific antibody or bispecific antigen binding fragment may be isolated.

In some embodiments, the bispecific antibodies and bispecific antigen binding fragments comprise an antigen binding fragment or a polypeptide according to the present invention. In some embodiments, the bispecific antibodies and bispecific antigen binding fragments comprise an antigen binding domain capable of binding to PD-1, wherein the antigen binding domain which is capable of binding to PD-1 comprises or consists of an antigen binding fragment or a polypeptide according to the present invention.

In some embodiments the bispecific antibodies and bispecific antigen binding fragments comprise an antigen binding domain capable of binding to PD-1, and an antigen binding domain capable of binding to another target protein.

The antigen binding domain capable of binding to another target protein may be capable of binding to another protein other than PD-1. In some embodiments, the target protein is a cell surface receptor. In some embodiments, the target protein is a cell surface receptor expressed on the cell surface of immune cells, e.g. T cells. In some embodiments, the target protein may be a member of the CD28 family. In some embodiments, the target protein may be a member of the CD28 family such as TIM-3 (HAVCR2), LAG3 (CD223), ICOS (CD278), CTLA4 (CD152), BTLA (CD272) or CD28. In particular embodiments, the target protein may be CTLA4 or LAG3.

In some embodiments, the antigen binding domain for TIM-3 may comprise the CDRs, light and heavy chain variable domains or other TIM-3 binding fragment of e.g. anti-TIM-3 antibody clone F38-2E2 (BioLegend), clone 2E2 (Merck Millipore), clone 6136E2, clone 024 (Sino Biological) clone 344801 (R&D Systems), clone E-18, clone H-191 (Santa Cruz Biotechnology), or clone 13A224 (United States Biological). In some embodiments, the antigen binding domain for LAG3 may comprise the CDRs, light and heavy chain variable domains or other LAG3 binding fragment of e.g. anti-LAG3 antibody clone 17B4 (Enzo Life Sciences), clone 333210 (R&D Systems), or clone 14L676 (United States Biological). In some embodiments, the antigen binding domain for ICOS may comprise the CDRs, light and heavy chain variable domains or other ICOS binding fragment of e.g. anti-ICOS antibody clone ISA-3 (eBioscience), clone SP98 (Novus Biologicals), clone 1G1, clone 3G4 (Abnova Corporation), clone 669222 (R&D Systems), clone TQ09 (Creative Diagnostics), or clone C398.4A (BioLegend). In some embodiments, the antigen binding domain for CTLA4 may comprise the CDRs, light and heavy chain variable domains or other CTLA4 binding fragment of e.g. anti-CTLA4 antibody clone 2F1, clone 1 F4 (Abnova Corporation), clone 9H10 (EMD Millipore), clone BNU3 (GeneTex), clone 1E2, clone AS32 (LifeSpan Biosciences) clone A3.4H2.H12 (Acris Antibodies), clone 060 (Sino Biological), clone BU5G3 (Creative Diagnostics), clone MIH8 (MBL International), clone A3.6B10.G1, or clone L3D10 (BioLegend). In some embodiments, the antigen binding domain for BTLA may comprise the CDRs, light and heavy chain variable domains or other BTLA binding fragment of e.g. anti-BTLA antibody clone 1B7, clone 2G8, clone 4C5 (Abnova Corporation), clone 4B8 (antibodies-online), clone MIH26 (Thermo Scientific Pierce Antibodies), clone UMAB61 (OriGene Technologies), clone 330104 (R&D Systems), clone 1B4 (LifeSpan BioSciences), clone 440205, clone 5E7 (Creative Diagnostics). In some embodiments, the antigen binding domain for CD28 may comprise the CDRs, light and heavy chain variable domains or other CD28 binding fragment of e.g. anti-CD28 antibody clone CD28.6 (eBioscience), clone CD28.2, clone JJ319 (Novus Biologicals), clone 204.12, clone B-23, clone 10F3 (Thermo Scientific Pierce Antibodies), clone 37407 (R&D Systems), clone 204-12 (Abnova Corporation), clone 15E8 (EMD Millipore), clone 204-12, clone YTH913.12 (AbD Serotec), clone B-T3 (Acris Antibodies), clone 9H6E2 (Sino Biological), clone C28/77 (MyBioSource.com), clone KOLT-2 (ALPCO), clone 152-2E10 (Santa Cruz Biotechnology), or clone XPH-56 (Creative Diagnostics).

An antigen binding domain of a bispecific antibody or bispecific antigen binding fragment according to the present invention may be any domain of a polypeptide which is capable of binding to an antigen. In some embodiments, an antigen binding domain comprises at least the three light chain CDRs (i.e. LC-CDR1, LC-CDR2 and LC-CDR3) and three heavy chain CDRs (i.e. HC-CDR1, HC-CDR2 and HC-CDR3) which together define the antigen binding region of an antibody or antigen binding fragment. In some embodiments, an antigen binding domain may comprise the light chain variable domain and heavy chain variable domain of an antibody or antigen binding fragment. In some embodiments, an antigen binding domain may comprise the light chain polypeptide and heavy chain polypeptide of an antibody or antigen binding fragment.

Bispecific antibodies and bispecific antigen binding fragments according to the invention may be provided in any suitable format, such as those formats described in Kontermann MAbs 2012, 4(2): 182-197, which is hereby incorporated by reference in its entirety. For example, a bispecific antibody or bispecific antigen binding fragment may be a bispecific antibody conjugate (e.g. an IgG2, F(ab')$_2$ or CovX-Body), a bispecific IgG or IgG-like molecule (e.g. an IgG, scFv$_4$-Ig, IgG-scFv, scFv-IgG, DVD-Ig, IgG-sVD, sVD-IgG, 2 in 1-IgG, mAb$^2$, or Tandemab common LC), an asymmetric bispecific IgG or IgG-like molecule (e.g. a kih IgG, kih IgG common LC, CrossMab, kih IgG-scFab, mAb-Fv, charge pair or SEED-body), a small bispecific antibody molecule (e.g. a Diabody (Db), dsDb, DART, scDb, tand-Abs, tandem scFv (taFv), tandem dAb/VHH, triple body, triple head, Fab-scFv, or F(ab')$_2$-scFv$_2$), a bispecific Fc and C$_H$3 fusion protein (e.g. a taFv-Fc, Di-diabody, scDb-C$_H$3, scFv-Fc-scFv, HCAb-VHH, scFv-kih-Fc, or scFv-kih-C$_H$3), or a bispecific fusion protein (e.g. a scFv$_2$-albumin, scDb-albumin, taFv-toxin, DNL-Fab$_3$, DNL-Fab$_4$-IgG, DNL-Fab$_4$-IgG-cytokine$_2$). See in particular FIG. 2 of Kontermann MAbs 2012, 4(2): 182-19.

The skilled person is able to design and prepare bispecific antibodies and bispecific antigen binding fragments according to the present invention.

Methods for producing bispecific antibodies include chemically crosslinking of antibodies or antibody fragments, e.g. with reducible disulphide or non-reducible thioether bonds, for example as described in Segal and Bast, 2001. Production of Bispecific Antibodies. Current Protocols in Immunology. 14:IV:2.13:2.13.1-2.13.16, which is hereby incorporated by reference in its entirety. For example, N-succinimidyl-3-(-2-pyridyldithio)-propionate (SPDP) can be used to chemically crosslink e.g. Fab fragments via hinge region SH— groups, to create disulfide-linked bispecific F(ab)$_2$ heterodimers.

Other methods for producing bispecific antibodies include fusing antibody-producing hybridomas e.g. with polyethylene glycol, to produce a quadroma cell capable of secreting bispecific antibody, for example as described in D. M. and Bast, B. J. 2001. Production of Bispecific Antibodies. Current Protocols in Immunology. 14:IV:2.13:2.13.1-2.13.16.

Bispecific antibodies and bispecific antigen binding fragments according to the present invention can also be produced recombinantly, by expression from e.g. a nucleic acid construct encoding polypeptides for the antigen binding molecules, for example as described in Antibody Engineering: Methods and Protocols, Second Edition (Humana Press, 2012), at Chapter 40: Production of Bispecific Antibodies: Diabodies and Tandem scFv (Hornig and Färber-Schwarz), or French, How to make bispecific antibodies, Methods Mol. Med. 2000; 40:333-339, the entire contents of both of which are hereby incorporated by reference.

For example, a DNA construct encoding the light and heavy chain variable domains for the two antigen binding domains (i.e. the light and heavy chain variable domains for the antigen binding domain capable of binding PD-1, and the light and heavy chain variable domains for the antigen binding domain capable of binding to another target protein), and including sequences encoding a suitable linker or dimerization domain between the antigen binding domains can be prepared by molecular cloning techniques. Recombinant bispecific antibody can thereafter be produced by expression (e.g. in vitro) of the construct in a suitable host cell (e.g. a mammalian host cell), and expressed recombinant bispecific antibody can then optionally be purified.

Antibodies may be produced by a process of affinity maturation in which a modified antibody is generated that has an improvement in the affinity of the antibody for antigen, compared to an unmodified parent antibody. Affinity-matured antibodies may be produced by procedures known in the art, e.g., Marks et al., *Rio/Technology* 10:779-783 (1992); Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):331 0-15 9 (1995); and Hawkins et al, *J. Mol. Biol.* 226:889-896 (1992).

Antibodies according to the present invention preferably exhibit specific binding to PD-1. An antibody that specifically binds to a target molecule preferably binds the target with greater affinity, and/or with greater duration than it binds to other targets. In one embodiment, the extent of binding of an antibody to an unrelated target is less than about 10% of the binding of the antibody to the target as measured, e.g., by ELISA, or by a radioimmunoassay (RIA). Alternatively, the binding specificity may be reflected in terms of binding affinity where the anti-PD-1 antibody of the present invention binds to PD-1 with a $K_D$ that is at least 0.1 order of magnitude (i.e. $0.1 \times 10^n$, where n is an integer representing the order of magnitude) greater than the $K_D$ of the antibody towards another target molecule, e.g. another member of the CD28 family. This may optionally be one of at least 0.2, 0.3, 0.4, 0.5, 0.6, 0.7, 0.8, 0.9, 1.0, 1.5, or 2.0.

Antibodies according to the present invention preferably have a dissociation constant ($K_D$) of one of ≤1 µM, ≤100 nM, ≤10 nM, nM or ≤100 pM. Binding affinity of an antibody for its target is often described in terms of its dissociation constant ($K_D$). Binding affinity can be measured by methods known in the art, such as by Surface Plasmon Resonance, or by a radiolabeled antigen binding assay (RIA) performed with the Fab version of the antibody and antigen molecule.

Antibodies according to the present invention may be "antagonist" antibodies that inhibit or reduce a biological activity of the antigen to which it binds. Blocking of PD-1 assists in the restoration of T-cell function by inhibiting the immune-inhibitory signalling pathway mediated by PD-1.

In some aspects, the antibody is clone A3, or a variant of A3. A3 comprises the following CDR sequences:

```
Light chain:
                                    (SEQ ID NO: 25)
    LC-CDR1: SGSSSNIKFNSVN (SEQ ID NO: 26)
    LC-CDR2: SNNQRPS (SEQ ID NO: 27)
    LC-CDR3: ASWDDVLYGSV Heavy chain:
                                    (SEQ ID NO: 39)
    HC-CDR1: GFTFSSYGMH
    or
                                    (SEQ ID NO: 89)
    SYGMH (SEQ ID NO: 40)
    HC-CDR2: VISYDGSNKYYADSVKG (SEQ ID NO: 41)
    HC-CDR3: DLGAGPYYYGKDH
```

CDR sequences determined by Kabat definition.

In some aspects, the antibody is clone A10, or a variant of A10. A10 comprises the following CDR sequences:

```
Light chain:
                                    (SEQ ID NO: 25)
    LC-CDR1: SGSSSNIKFNSVN (SEQ ID NO: 26)
    LC-CDR2: SNNQRPS (SEQ ID NO: 28)
    LC-CDR3: ASWDDYYYGTI Heavy chain:
                                    (SEQ ID NO: 39)
    HC-CDR1: GFTFSSYGMH
    or
                                    (SEQ ID NO: 89)
    SYGMH (SEQ ID NO: 40)
    HC-CDR2: VISYDGSNKYYADSVKG (SEQ ID NO: 42)
    HC-CDR3: DLGAGPYYYGKDV
```

CDR sequences determined by Kabat definition.

In some aspects, the antibody is clone B6, or a variant of B6. B6 comprises the following CDR sequences:

```
Light chain:
                                    (SEQ ID NO: 25)
    LC-CDR1: SGSSSNIKFNSVN (SEQ ID NO: 26)
    LC-CDR2: SNNQRPS (SEQ ID NO: 29)
    LC-CDR3: ASWDDYLRGTV Heavy chain:
                                    (SEQ ID NO: 39)
    HC-CDR1: GFTFSSYGMH
    or
                                    (SEQ ID NO: 89)
    SYGMH (SEQ ID NO: 40)
    HC-CDR2: VISYDGSNKYYADSVKG (SEQ ID NO: 43)
    HC-CDR3: DYGAGPYYYGMDV
```

CDR sequences determined by Kabat definition.

In some aspects, the antibody is clone C4, or a variant of C4. C4 comprises the following CDR sequences:

```
Light chain:
                                    (SEQ ID NO: 25)
    LC-CDR1: SGSSSNIKFNSVN (SEQ ID NO: 26)
    LC-CDR2: SNNQRPS (SEQ ID NO: 30)
    LC-CDR3: SAWDDYLHGTV Heavy chain:
                                    (SEQ ID NO: 39)
    HC-CDR1: GFTFSSYGMH
    or
                                    (SEQ ID NO: 89)
    SYGMH (SEQ ID NO: 40)
    HC-CDR2: VISYDGSNKYYADSVKG (SEQ ID NO: 44)
    HC-CDR3: DLGAGPYYYGLDV
```

CDR sequences determined by Kabat definition.

In some aspects, the antibody is clone D4, or a variant of D4. D4 comprises the following CDR sequences:

```
Light chain:
                                    (SEQ ID NO: 25)
    LC-CDR1: SGSSSNIKFNSVN (SEQ ID NO: 26)
    LC-CDR2: SNNQRPS (SEQ ID NO: 31)
    LC-CDR3: ASWDDYVRGTM Heavy chain:
                                    (SEQ ID NO: 39)
    HC-CDR1: GFTFSSYGMH
    or
                                    (SEQ ID NO: 89)
    SYGMH (SEQ ID NO: 40)
    HC-CDR2: VISYDGSNKYYADSVKG (SEQ ID NO: 45)
    HC-CDR3: DLGAGPYYYGMDV
```

CDR sequences determined by Kabat definition.

In some aspects, the antibody is clone E1, or a variant of E1. E1 comprises the following CDR sequences:

```
Light chain:
                            (SEQ ID NO: 25)
LC-CDR1: SGSSSNIKFNSVN (SEQ ID NO: 26)
LC-CDR2: SNNQRPS (SEQ ID NO: 32)
LC-CDR3: SSWDDFLRGTV Heavy chain:
                            (SEQ ID NO: 39)
HC-CDR1: GFTFSSYGMH
or
                            (SEQ ID NO: 89)
SYGMH (SEQ ID NO: 40)
HC-CDR2: VISYDGSNKYYADSVKG (SEQ ID NO: 46)
HC-CDR3: DLGAGPYYYGMDV
```

CDR sequences determined by Kabat definition.

In some aspects, the antibody is clone F2, or a variant of F2. F2 comprises the following CDR sequences:

```
Light chain:
                            (SEQ ID NO: 25)
LC-CDR1: SGSSSNIKFNSVN (SEQ ID NO: 26)
LC-CDR2: SNNQRPS (SEQ ID NO: 33)
LC-CDR3: SSWDDDARGTI Heavy chain:
                            (SEQ ID NO: 39)
HC-CDR1: GFTFSSYGMH
or
                            (SEQ ID NO: 89)
SYGMH (SEQ ID NO: 40)
HC-CDR2: VISYDGSNKYYADSVKG (SEQ ID NO: 47)
HC-CDR3: DLGAGPYYYGMDV
```

CDR sequences determined by Kabat definition.

In some aspects, the antibody is clone G1, or a variant of G1. G1 comprises the following CDR sequences:

```
Light chain:
                            (SEQ ID NO: 25)
LC-CDR1: SGSSSNIKFNSVN (SEQ ID NO: 26)
LC-CDR2: SNNQRPS (SEQ ID NO: 34)
LC-CDR3: AAWDDVYYGTI Heavy chain:
                            (SEQ ID NO: 39)
HC-CDR1: GFTFSSYGMH
or
                            (SEQ ID NO: 89)
SYGMH (SEQ ID NO: 40)
HC-CDR2: VISYDGSNKYYADSVKG (SEQ ID NO: 48)
HC-CDR3: DLGAGPYYYGMDV
```

CDR sequences determined by Kabat definition.

In some aspects, the antibody is clone G2, or a variant of G2. G2 comprises the following CDR sequences:

```
Light chain:
                            (SEQ ID NO: 25)
LC-CDR1: SGSSSNIKFNSVN (SEQ ID NO: 26)
LC-CDR2: SNNQRPS (SEQ ID NO: 35)
LC-CDR3: ASWDDSLYGTV Heavy chain:
                            (SEQ ID NO: 39)
HC-CDR1: GFTFSSYGMH
or
                            (SEQ ID NO: 89)
SYGMH (SEQ ID NO: 40)
HC-CDR2: VISYDGSNKYYADSVKG (SEQ ID NO: 49)
HC-CDR3: DLGAGPYYYGMDV
```

CDR sequences determined by Kabat definition.

In some aspects, the antibody is clone G10, or a variant of G10. G10 comprises the following CDR sequences:

```
Light chain:
                            (SEQ ID NO: 25)
LC-CDR1: SGSSSNIKFNSVN (SEQ ID NO: 26)
LC-CDR2: SNNQRPS (SEQ ID NO: 36)
LC-CDR3: AAWDDAYYGTI Heavy chain:
                            (SEQ ID NO: 39)
HC-CDR1: GFTFSSYGMH
or
                            (SEQ ID NO: 89)
SYGMH (SEQ ID NO: 40)
HC-CDR2: VISYDGSNKYYADSVKG (SEQ ID NO: 50)
HC-CDR3: DYGAGPYYYGMDV
```

CDR sequences determined by Kabat definition.

In some aspects, the antibody is clone H4, or a variant of H4. H4 comprises the following CDR sequences:

```
Light chain:
                            (SEQ ID NO: 25)
LC-CDR1: SGSSSNIKFNSVN (SEQ ID NO: 26)
LC-CDR2: SNNQRPS (SEQ ID NO: 37)
LC-CDR3: ASWDDVYRGTV Heavy chain:
                            (SEQ ID NO: 39)
HC-CDR1: GFTFSSYGMH
or
                            (SEQ ID NO: 89)
SYGMH (SEQ ID NO: 40)
HC-CDR2: VISYDGSNKYYADSVKG
```

```
HC-CDR3: DLGSGYYLYGMDV            (SEQ ID NO: 51)
```

CDR sequences determined by Kabat definition.

In some aspects, the antibody is clone H9, or a variant of H9. H9 comprises the following CDR sequences:

```
Light chain:
                                  (SEQ ID NO: 25)
LC-CDR1: SGSSSNIKFNSVN (SEQ ID NO: 26)
LC-CDR2: SNNQRPS (SEQ ID NO: 38)
LC-CDR3: SSWDDSLYGTI Heavy chain:
                                  (SEQ ID NO: 39)
HC-CDR1: GFTFSSYGMH
or
                                  (SEQ ID NO: 89)
SYGMH (SEQ ID NO: 40)
HC-CDR2: VISYDGSNKYYADSVKG (SEQ ID NO: 52)
HC-CDR3: DLGAGPYYYGMDV
```

CDR sequences determined by Kabat definition.

Antibodies according to the present invention may comprise the CDRs of one of A3, A10, B6, C4, D4, E1, F2, G1, G2, G10, H4, or H9 or one of SEQ ID NOs 1 and 13, 2 and 14, 3 and 15, 4 and 16, 5 and 17, 6 and 18, 7 and 19, 8 and 20, 9 and 21, 10 and 22, 11 and 23, or 12 and 24. In an antibody according to the present invention one or two or three or four of the six CDR sequences may vary. A variant may have one or two amino acid substitutions in one or two of the six CDR sequences.

Amino acid sequences of the $V_H$ and $V_L$ chains of ant-PD-1 clones are shown in FIGS. 1 and 2. The encoding nucleotide sequences are shown in FIG. 4.

The light and heavy chain CDRs may also be particularly useful in conjunction with a number of different framework regions. Accordingly, light and/or heavy chains having LC-CDR1-3 or HC-CDR1-3 may possess an alternative framework region. Suitable framework regions are well known in the art and are described for example in M. Lefranc & G. Lefranc (2001) "The Immunoglobulin Facts-Book", Academic Press, incorporated herein by reference.

In this specification, antibodies may have $V_H$ and/or VL chains comprising an amino acid sequence that has a high percentage sequence identity to one or more of the $V_H$ and/or $V_L$ amino acid sequences of SEQ ID Nos 1 and 13, 2 and 14, 3 and 15, 4 and 16, 5 and 17, 6 and 18, 7 and 19, 8 and 20, 9 and 21, 10 and 22, 11 and 23, or 12 and 24 respectively, or to one or the amino acid sequences shown in FIGS. 1 and 2.

For example, antibodies according to the present invention include antibodies that bind PD-1 and have a $V_H$ or $V_L$ chain that comprises an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to the $V_H$ or $V_L$ chain amino acid sequence of one of SEQ ID NOs 1 to 24 or to one or the amino acid sequences shown in FIGS. 1 and 2.

Antibodies according to the present invention may be detectably labelled or, at least, capable of detection. For example, the antibody may be labelled with a radioactive atom or a coloured molecule or a fluorescent molecule or a molecule which can be readily detected in any other way. Suitable detectable molecules include fluorescent proteins, luciferase, enzyme substrates, and radiolabels. The binding moiety may be directly labelled with a detectable label or it may be indirectly labelled. For example, the binding moiety may be an unlabelled antibody which can be detected by another antibody which is itself labelled. Alternatively, the second antibody may have bound to it biotin and binding of labelled streptavidin to the biotin is used to indirectly label the first antibody.

Methods of Detection

Antibodies, or antigen binding fragments, described herein may be used in methods that involve the binding of the antibody or antigen binding fragment to PD-1. Such methods may involve detection of the bound complex of antibody, or antigen binding fragment, and PD-1. As such, in one embodiment a method is provided, the method comprising contacting a sample containing, or suspected to contain, PD-1 with an antibody or antigen binding fragment as described herein and detecting the formation of a complex of antibody, or antigen binding fragment, and PD-1.

Suitable method formats are well known in the art, including immunoassays such as sandwich assays, e.g. ELISA. The method may involve labelling the antibody, or antigen binding fragment, or PD-1, or both, with a detectable label, e.g. fluorescent, luminescent or radio-label.

Methods of this kind may provide the basis of a method of diagnosis of a disease or condition requiring detection and or quantitation of PD-1. Such methods may be performed in vitro on a patient sample, or following processing of a patient sample. Once the sample is collected, the patient is not required to be present for the in vitro method of diagnosis to be performed and therefore the method may be one which is not practised on the human or animal body.

Such methods may involve determining the amount of PD-1 present in a patient sample. The method may further comprise comparing the determined amount against a standard or reference value as part of the process of reaching a diagnosis. Other diagnostic tests may be used in conjunction with those described here to enhance the accuracy of the diagnosis or prognosis or to confirm a result obtained by using the tests described here.

The level of PD-1 present in a patient sample may be indicative that a patient may respond to treatment with an anti-PD1 antibody. The presence of a high level of PD-1 in a sample may be used to select a patient for treatment with an anti-PD1 antibody. The antibodies of the present invention may therefore be used to select a patient for treatment with anti-PD-1 therapy.

Detection in a sample of PD-1 may be used for the purpose of diagnosis of a T-cell dysfunctional disorder or a cancerous condition in the patient, diagnosis of a predisposition to a cancerous condition or for providing a prognosis (prognosticating) of a cancerous condition. The diagnosis or prognosis may relate to an existing (previously diagnosed) cancerous condition, which may be benign or malignant, may relate to a suspected cancerous condition or may relate to the screening for cancerous conditions in the patient (which may be previously undiagnosed).

In one embodiment the level of PD-1 expression on $CD8^+$ T cells may be detected in order to indicate the degree of T-cell exhaustion and severity of the disease state.

A sample may be taken from any tissue or bodily fluid. The sample may comprise or may be derived from: a quantity of blood; a quantity of serum derived from the individual's blood which may comprise the fluid portion of the blood obtained after removal of the fibrin clot and blood cells; a tissue sample or biopsy; or cells isolated from said individual.

Methods according to the present invention are preferably performed in vitro. The term "in vitro" is intended to encompass experiments with cells in culture whereas the term "in vivo" is intended to encompass experiments with intact multi-cellular organisms.

Therapeutic Applications

Antibodies, antigen binding fragments and polypeptides according to the present invention and compositions comprising such agents may be provided for use in methods of medical treatment. Treatment may be provided to subjects having a disease or condition in need of treatment. The disease or condition may be one of a T-cell dysfunctional disorder, including a T-cell dysfunctional disorder associated with a cancer, or a cancer, or a T-cell dysfunctional disorder associated with an infection, or an infection.

A T-cell dysfunctional disorder may be a disease or condition in which normal T-cell function is impaired causing downregulation of the subject's immune response to pathogenic antigens, e.g. generated by infection by exogenous agents such as microorganisms, bacteria and viruses, or generated by the host in some disease states such as in some forms of cancer (e.g. in the form of tumor associated antigens).

The T-cell dysfunctional disorder may comprise T-cell exhaustion or T-cell anergy. T-cell exhaustion comprises a state in which $CD8^+$ T-cells fail to proliferate or exert T-cell effector functions such as cytotoxicity and cytokine (e.g. IFNγ) secretion in response to antigen stimulation. Exhausted T-cells may also be characterised by sustained expression of PD-1, where blockade of PD-1:PD-L1 interactions may reverse the T-cell exhaustion and restore antigen-specific T cell responses.

The T-cell dysfunctional disorder may be manifest as an infection, or inability to mount an effective immune response against an infection. The infection may be chronic, persistent, latent or slow, and may be the result of bacterial, viral, fungal or parasitic infection. As such, treatment may be provided to patients having a bacterial, viral or fungal infection. Examples of bacterial infections include infection with *Helicobacter pylori*. Examples of viral infections include infection with HIV, hepatitis B or hepatitis C.

The T-cell dysfunctional disorder may be associated with a cancer, such as tumor immune escape. Many human tumors express tumor-associated antigens recognised by T cells and capable of inducing an immune response. However, immune evasion is common and is believed to be mediated by a number of soluble factors, including PD-L1. As such, blocking the interaction of PD-1 and PD-L1 may inhibit this negative immunoregulatory signal to tumor cells and enhance tumor-specific $CD8^+$ T-cell immunity.

Cancers may also be treated where there is no indication of a T-cell dysfunctional disorder such as T-cell exhaustion but the use of an antibody, antigen binding fragment or polypeptide according to the present invention allows the subject to suppress PD-1 signalling and mount an effective immune response with limited impairment, evasion or induction of tumor immune escape. In such treatments, the antibody, antigen binding fragment or polypeptide may provide a treatment for cancer that involves prevention of the development of tumor immune escape.

The treatment may be aimed at prevention of the T-cell dysfunctional disorder, e.g. prevention of infection or of the development or progression of a cancer. As such, the antibodies, antigen binding fragments and polypeptides may be used to formulate pharmaceutical compositions or medicaments and subjects may be prophylactically treated against development of a disease state. This may take place before the onset of symptoms of the disease state, and/or may be given to subjects considered to be at greater risk of infection or development of cancer.

Treatment may comprise co-therapy with a vaccine, e.g. T-cell vaccine, which may involve simultaneous, separate or sequential therapy, or combined administration of vaccine and antibody, antigen binding fragment or polypeptide in a single composition. In this context, the antibody, antigen binding fragment or polypeptide may be provided as an adjuvant to the vaccine. Limited proliferative potential of exhausted T cells has been attributed as a main reason for failure of T-cell immunotherapy and combination an agent capable of blocking or reversing T cell exhaustion is a potential strategy for improving the efficacy of T-cell immunotherapy (Barber et al., *Nature* Vol 439, No. 9 p 682-687 February 2006).

Administration of an antibody, antigen binding fragment or polypeptide is preferably in a "therapeutically effective amount", this being sufficient to show benefit to the individual. The actual amount administered, and rate and time-course of administration, will depend on the nature and severity of the disease being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

Formulating Pharmaceutically Useful Compositions and Medicaments

Antibodies, antigen binding fragments and polypeptides according to the present invention may be formulated as pharmaceutical compositions for clinical use and may comprise a pharmaceutically acceptable carrier, diluent, excipient or adjuvant.

In accordance with the present invention methods are also provided for the production of pharmaceutically useful compositions, such methods of production may comprise one or more steps selected from: isolating an antibody, antigen binding fragment or polypeptide as described herein; and/or mixing an isolated antibody, antigen binding fragment or polypeptide as described herein with a pharmaceutically acceptable carrier, adjuvant, excipient or diluent.

For example, a further aspect of the present invention relates to a method of formulating or producing a medicament or pharmaceutical composition for use in the treatment of a T-cell dysfunctional disorder, the method comprising formulating a pharmaceutical composition or medicament by mixing an antibody, antigen binding fragment or polypeptide as described herein with a pharmaceutically acceptable carrier, adjuvant, excipient or diluent.

Infection

An infection may be any infection or infectious disease, e.g. bacterial, viral, fungal, or parasitic infection. In some embodiments it may be particularly desirable to treat chronic/persistent infections, e.g. where such infections are associated with T cell dysfunction or T cell exhaustion.

It is well established that T cell exhaustion is a state of T cell dysfunction that arises during many chronic infections (including viral, bacterial and parasitic), as well as in cancer (Wherry *Nature Immunology* Vol. 12, No. 6, p 492-499, June 2011).

An infection or infectious disease may be one in which PD-1 is upregulated (e.g. as reported by Radziewicz H, et al., J Virol. 2007; 81(6):2545-2553 and Golden-Mason L et al., J Virol. 2007; 81(17):9249-9258).

Examples of bacterial infections that may be treated include infection by *Bacillus* spp., *Bordetella pertussis*, *Clostridium* spp., *Corynebacterium* spp., *Vibrio chloerae*, *Staphylococcus* spp., *Streptococcus* spp. *Escherichia*, *Klebsiella*, *Proteus*, *Yersinia*, *Erwina*, *Salmonella*, *Listeria* sp, *Helicobacter pylori*, mycobacteria (e.g. *Mycobacterium tuberculosis*) and *Pseudomonas aeruginosa*. For example, the bacterial infection may be sepsis or tuberculosis.

Yao et al (PD-1 on dendritic cells impedes innate immunity against bacterial infection. *Blood* 113(23):5811-5818 Jun. 4, 2009) established PD-1 in the negative regulation of DC function during innate immune response to infection by *Listeria monocytogenes*. Brahmamdam et al (Delayed administration of anti-PD-1 antibody reverses immune dysfunction and improves survival during sepsis. *Journal of Leukocyte Biology* vo. 88, no. 2 233-240, August 2010) reported that anti-PD-1 antibody administered 24 h after sepsis prevented sepsis-induced depletion of lymphocytes and DCs, increased Bcl-xL, blocked apoptosis and improved survival. Tim3:Galectin-9 interactions have been reported to mediate T cell exhaustion and mediate the innate and adaptive immune response to infection by *Mycobacterium tuberculosis* (Jayaraman et al., *The Journal of Immunology* 2012, 188, 70.6).

Examples of viral infections that may be treated include infection by influenza virus, measles virus, hepatitis B virus (HBV), hepatitis C virus (HCV), human immunodeficiency virus (HIV), lymphocytic choriomeningitis virus (LCMV), Herpes simplex virus and human papilloma virus.

Chronic viral infections, such as those caused by HCV, HBV, and HIV commonly involve mechanisms to evade immune clearance. Expression of PD-1 and TIM-3 have been identified as correlating with defective T cell responses to hepatitis C virus (HCV) (McMahan et al., The Journal of Clinical Investigation Vol. 120, No. 12 p 4546-4557, December 2010). In HCV, McMahan et al (supra) found that the level of dual TIM-3 and PD-1 expression on HCV-specific CTLs predated the development of viral persistence, providing prognostic information. Barber et al. (Nature Vol 439, No. 9 p 682-687 February 2006) reported that PD-1 is upregulated during chronic viral infection. In mice infected with LCMV they reported that blockade of the PD-1/PD-L1 inhibitory pathway had a beneficial effect on CD8 T cells, restoring their ability to undergo proliferation, secrete cytokines, kill infected cells and decrease viral load. PD-1 is also upregulated in HIV infection (Said et al., *Nature Medicine* Vol. 16, No. 4 p 452-460 April 2010). Blocking interaction between PD-1 and PD-L1 contributed to viral clearance and improved T cell function in animal models of chronic viral infection (Said et al., supra).

Examples of fungal infections that may be treated include infection by *Alternaria* sp, *Aspergillus* sp, *Candida* sp and *Histoplasma* sp. The fungal infection may be fungal sepsis or histoplasmosis.

Chang et al (Blockade of the negative co-stimulatory molecules PD-1 and CTLA-4 improves survival in primary and secondary fungal sepsis. *Critical Care* 2013, 17:R85) reported that anti-PD1 antibodies were highly effective at improving survival in primary and secondary fungal sepsis. Lázár-Molnár et al (The PD-1/PD-L costimulatory pathway critically affects host resistance to the pathogenic fungus *Histoplasma capsulatum* PNAS vol. 105, no. 7, p 2658-2663, 19 Feb. 2008) reported that anti-PD-1 antibody significantly increased survival of mice infected with *Histoplasma capsulatum*. As such, the importance of T cell exhaustion in mediating fungal infection is well established.

Examples of parasitic infections that may be treated include infection by *Plasmodium* species (e.g. *Plasmodium falciparum, Plasmodium yoeli, Plasmodium ovale, Plasmodium vivax*, or *Plasmodium chabaudi chabaudi*). The parasitic infection may be a disease such as malaria, leishmaniasis and toxoplasmosis.

Infection of humans with *Plasmodium falciparum* has been shown to result in higher expression of PD-1 and T cell exhaustion mice (Butler et al., *Nature Immunology* Vol. 13, No. 12, p 188-195 February 2012). Blockade of PD-L1 and LAG-3 using anti-PD-L1 and anti-LAG-3 monoclonal antibodies in vivo contributed to the restoration of CD4$^+$ T-cell function, amplification of the number of follicular helper T cells, germinal-center B cells and plasmablasts, enhanced protective antibodies and rapidly cleared blood-stage malaria in mice. It was also shown to block the development of chronic infection (Butler et al., supra).

Cancer

A cancer may be any unwanted cell proliferation (or any disease manifesting itself by unwanted cell proliferation), neoplasm or tumor or increased risk of or predisposition to the unwanted cell proliferation, neoplasm or tumor. The cancer may be benign or malignant and may be primary or secondary (metastatic). A neoplasm or tumor may be any abnormal growth or proliferation of cells and may be located in any tissue. Examples of tissues include the adrenal gland, adrenal medulla, anus, appendix, bladder, blood, bone, bone marrow, brain, breast, cecum, central nervous system (including or excluding the brain) cerebellum, cervix, colon, duodenum, endometrium, epithelial cells (e.g. renal epithelia), gallbladder, oesophagus, glial cells, heart, ileum, jejunum, kidney, lacrimal glad, larynx, liver, lung, lymph, lymph node, lymphoblast, maxilla, mediastinum, mesentery, myometrium, nasopharynx, omentume, oral cavity, ovary, pancreas, parotid gland, peripheral nervous system, peritoneum, pleura, prostate, salivary gland, sigmoid colon, skin, small intestine, soft tissues, spleen, stomach, testis, thymus, thyroid gland, tongue, tonsil, trachea, uterus, vulva, white blood cells.

Tumors to be treated may be nervous or non-nervous system tumors. Nervous system tumors may originate either in the central or peripheral nervous system, e.g. glioma, medulloblastoma, meningioma, neurofibroma, ependymoma, Schwannoma, neurofibrosarcoma, astrocytoma and oligodendroglioma. Non-nervous system cancers/tumors may originate in any other non-nervous tissue, examples include melanoma, mesothelioma, lymphoma, myeloma, leukemia, Non-Hodgkin's lymphoma (NHL), Hodgkin's lymphoma, chronic myelogenous leukemia (CML), acute myeloid leukemia (AML), myelodysplastic syndrome (MDS), cutaneous T-cell lymphoma (CTCL), chronic lymphocytic leukemia (CLL), hepatoma, epidermoid carcinoma, prostate carcinoma, breast cancer, lung cancer, colon cancer, ovarian cancer, pancreatic cancer, thymic carcinoma, NSCLC, haematologic cancer and sarcoma.

In some embodiments, the cancer is one or more of lung cancer, renal cancer and bladder cancer.

Adoptive T Cell Transfer Therapy

Adoptive T cell transfer therapy generally refers to a process in which white blood cells are removed from a subject, typically by drawing a blood sample from which white blood cells are separated, expanded in vitro or ex vivo and returned either to the same subject or to a different subject. The treatment is typically aimed at increasing the amount/concentration of an active form of the required T cell population in the subject. Such treatment may be beneficial in subjects experiencing T cell exhaustion.

Antibodies capable of blocking the mechanism of T cell exhaustion, or reversing it, provide a means of enhancing T cell activity and promoting T cell expansion.

Accordingly, in a further aspect of the present invention a method is provided for expanding a population of T cells, wherein T cells are contacted in vitro or ex vivo with an antibody, antigen binding fragment or polypeptide according to the present invention.

The method may optionally comprise one or more of the following steps: taking a blood sample from a subject; isolating T cells from the blood sample; culturing the T cells in in vitro or ex vivo cell culture (where they may be contacted with the antibody, antigen binding fragment or polypeptide), collecting an expanded population of T cells; mixing the T cells with an adjuvant, diluent, or carrier; administering the expanded T cells to a subject.

Accordingly, in some aspects of the present invention a method of treatment of a subject having a T-cell dysfunctional disorder is provided, the method comprising obtaining a blood sample from a subject in need of treatment, culturing T cells obtained from the blood sample in the presence of an antibody, antigen binding fragment or polypeptide according to the present invention so as to expand the T cell population, collecting expanded T cells, and administering the expanded T cells to a subject in need of treatment.

The T cells may be obtained from a subject requiring treatment, and may be isolated and/or purified. They may be a $CD4^+$ and/or $CD8^+$ T-cell population. The T-cells may represent a population experiencing T cell exhaustion and may optionally have upregulated expression of PD-1.

During culture, T cells may be contacted with the antibody, antigen binding fragment or polypeptide under conditions and for a period of time suitable to allow expansion of the T cells to a desired number of cells. After a suitable period of time the T cells may be harvested, optionally concentrated, and may be mixed with a suitable carrier, adjuvant or diluent and returned to the subject's body. A subject may undergo one or more rounds of such therapy.

Methods of T cell expansion are well known in the art, such as those described in Kalamasz et al., *J Immunother* 2004 September-October; 27(5):405-18; Montes et al., *Clin Exp Immunol* 2005 November; 142(2):292-302; Wölfl and Greenburg *Nature Protocols* 9 p 950-966 27 Mar. 2014; Trickett and Kwan *Journal of Immunological Methods* Vol. 275, Issues 1-2, 1 Apr. 2003, p 251-255; Butler et al *PLoSONE* 7(1) 12 Jan. 2012.

Simultaneous or Sequential Administration

Compositions may be administered alone or in combination with other treatments, either simultaneously or sequentially dependent upon the condition to be treated.

In this specification an antibody, antigen binding fragment or polypeptide of the present invention and an anti-infective agent or chemotherapeutic agent (therapeutic agent) may be administered simultaneously or sequentially.

In some embodiments, treatment with an antibody, antigen binding fragment or polypeptide of the present invention may be accompanied by chemotherapy.

Simultaneous administration refers to administration of the antibody, antigen binding fragment or polypeptide and therapeutic agent together, for example as a pharmaceutical composition containing both agents (combined preparation), or immediately after each other and optionally via the same route of administration, e.g. to the same artery, vein or other blood vessel.

Sequential administration refers to administration of one of the antibody, antigen binding fragment or polypeptide or therapeutic agent followed after a given time interval by separate administration of the other agent. It is not required that the two agents are administered by the same route, although this is the case in some embodiments. The time interval may be any time interval.

Anti-Infective Agents

In treating infection, an antibody, antigen binding fragment or polypeptide of the present invention may be administered in combination with an anti-infective agent, as described above. The anti-infective agent may be an agent known to have action against the microorganism or virus responsible for the infection.

Suitable anti-infective agents include antibiotics (such as penicillins, cephalosporins, rifamycins, lipiarmycins, quinolones, sulfonamides, macrolides, lincosamides, tetracyclines, cyclic lipopeptides, glycylcyclines, oxazolidinones, and lipiarmycins), anti-viral agents (such as reverse transcriptase inhibitors, integrase inhibitors, transcription factor inhibitors, antisense and siRNA agents and protease inhibitors), anti-fungal agents (such as polyenes, imidiazoles, triazoles, thiazoles, allylamines, and echinocandins) and anti-parasitic agents (such as antinematode agents, anticestode agents, antitrematode agents, antiamoebic agents and antiprotozoal agents).

Chemotherapy

Chemotherapy refers to treatment of a cancer with a drug or with ionising radiation (e.g. radiotherapy using X-rays or y-rays). In preferred embodiments chemotherapy refers to treatment with a drug. The drug may be a chemical entity, e.g. small molecule pharmaceutical, antibiotic, DNA intercalator, protein inhibitor (e.g. kinase inhibitor), or a biological agent, e.g. antibody, antibody fragment, nucleic acid or peptide aptamer, nucleic acid (e.g. DNA, RNA), peptide, polypeptide, or protein. The drug may be formulated as a pharmaceutical composition or medicament. The formulation may comprise one or more drugs (e.g. one or more active agents) together with one or more pharmaceutically acceptable diluents, excipients or carriers.

A treatment may involve administration of more than one drug. A drug may be administered alone or in combination with other treatments, either simultaneously or sequentially dependent upon the condition to be treated. For example, the chemotherapy may be a co-therapy involving administration of two drugs, one or more of which may be intended to treat the cancer.

The chemotherapy may be administered by one or more routes of administration, e.g. parenteral, intravenous injection, oral, subcutaneous, intradermal or intratumoral.

The chemotherapy may be administered according to a treatment regime. The treatment regime may be a pre-determined timetable, plan, scheme or schedule of chemotherapy administration which may be prepared by a physician or medical practitioner and may be tailored to suit the patient requiring treatment.

The treatment regime may indicate one or more of: the type of chemotherapy to administer to the patient; the dose of each drug or radiation; the time interval between administrations; the length of each treatment; the number and nature of any treatment holidays, if any etc. For a co-therapy a single treatment regime may be provided which indicates how each drug is to be administered.

Chemotherapeutic drugs and biologics may be selected from:
- alkylating agents such as cisplatin, carboplatin, mechlorethamine, cyclophosphamide, chlorambucil, ifosfamide;
- purine or pyrimidine anti-metabolites such as azathiopurine or mercaptopurine;
- alkaloids and terpenoids, such as *vinca* alkaloids (e.g. vincristine, vinblastine, vinorelbine, vindesine), podophyllotoxin, etoposide, teniposide, taxanes such as paclitaxel (Taxol™), docetaxel;
- topoisomerase inhibitors such as the type I topoisomerase inhibitors camptothecins irinotecan and topotecan, or the type II topoisomerase inhibitors amsacrine, etoposide, etoposide phosphate, teniposide;
- antitumor antibiotics (e.g. anthracyline antibiotics) such as dactinomycin, doxorubicin (Adriamycin™), epirubicin, bleomycin, rapamycin;
- antibody based agents, such as anti-TIM-3 antibodies, anti-CTLA-4, anti-LAG-3, anti-4-1BB, anti-GITR, anti-CD27, anti-BLTA, anti-OX40, anti-VEGF, anti-TNFα, anti-IL-2, anti-GpIIb/IIIa, anti-CD-52, anti-CD20, anti-RSV, anti-HER2/neu(erbB2), anti-TNF receptor, anti-EGFR antibodies, monoclonal antibodies or antibody fragments, examples include: cetuximab, panitumumab, infliximab, basiliximab, bevacizumab (Avastin®), abciximab, daclizumab, gemtuzumab, alemtuzumab, rituximab (Mabthera®), palivizumab, trastuzumab, etanercept, adalimumab, nimotuzumab
- EGFR inihibitors such as erlotinib, cetuximab and gefitinib
- anti-angiogenic agents such as bevacizumab (Avastin®)
- cancer vaccines such as Sipuleucel-T (Provenge®)

In one embodiment the chemotherapeutic agent is an anti-TIM-3 antibody, anti-CTLA-4, anti-LAG3, anti-41BB, anti-GITR, anti-CD27, anti-BLTA, anti-OX40, anti-VEGF, anti-TNFα, anti-IL2, anti-GpIIb/IIIa, anti-CD-52, anti-CD20, anti-RSV, anti-HER2/neu(erbB2), anti-TNF receptor, anti-EGFR or other antibody. In some embodiments, the chemotherapeutic agent is an immune checkpoint inhibitor or costimulation molecule.

Further chemotherapeutic drugs may be selected from: 13-cis-Retinoic Acid, 2-Chlorodeoxyadenosine, 5-Azacitidine 5-Fluorouracil, 6-Mercaptopurine, 6-Thioguanine, Abraxane, Accutane®, Actinomycin-D Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Aranesp®, Aredia®, Arimidex®, Aromasin®, Arranon®, Arsenic Trioxide, Asparaginase, ATRA Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, Calcium Leucovorin, Campath®, Camptosar®, Camptothecin-11, Capecitabine, Carac™, Carboplatin, Carmustine, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine Cytosar-U®, Cytoxan®, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin, Diftitox, DepoCyt™, Dexamethasone, Dexamethasone Acetate, Dexamethasone Sodium Phosphate, Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Eligard™, Ellence™, Eloxatin™, Elspar®, Emcyt®, Epirubicin, Epoetin Alfa, Erbitux, Erlotinib, Erwinia L-asparaginase, Estramustine, Ethyol Etopophos®, Etoposide, Etoposide Phosphate, Eulexin®, Everolimus, Evista®, Exemestane, Faslodex®, Femara®, Filgrastim, Floxuridine, Fludara®, Fludarabine, Fluoroplex®, Fluorouracil, Fluoxymesterone, Flutamide, Folinic Acid, FUDR®, Fulvestrant, Gefitinib, Gemcitabine, Gemtuzumab ozogamicin, Gleevec™, Gliadel® Wafer, Goserelin, Granulocyte—Colony Stimulating Factor, Granulocyte Macrophage Colony Stimulating Factor, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan, Idamycin®, Idarubicin, Ifex®, IFN-alpha, Ifosfamide, IL-11, IL-2, Imatinib mesylate, Imidazole Carboxamide, Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra™, Kidrolase, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine, Mutamycin®, Myleran®, Mylocel™, Mylotarg®, Navelbine®, Nelarabine, Neosar®, Neulasta™, Neumega®, Neupogen®, Nexavar®, Nilandron®, Nilutamide, Nipent®, Nitrogen Mustard, Novaldex®, Novantrone®, Octreotide, Octreotide acetate, Oncospar®, Oncovin®, Ontak®, Onxal™, Oprevelkin, Oraprep®, Orasone®, Oxaliplatin, Paclitaxel, Paclitaxel Protein-bound, Pamidronate, Panitumumab, Panretin®, Paraplatin®, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant Purinethol®, Raloxifene, Revlimid®, Rheumatrex®, Rituxan®, Rituximab, Roferon-A® (Interferon Alfa-2a), Rubex®, Rubidomycin hydrochloride, Sandostatin® Sandostatin LAR®, Sargramostim, Solu-Cortef®, Solu-Medrol®, Sorafenib, SPRYCEL™, STI-571, Streptozocin, SU11248, Sunitinib, Sutent®, Tamoxifen, Tarceva®, Targretin®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, VP-16, Vumon®, Xeloda®, Zanosar®, Zevalin™, Zinecard®, Zoladex®, Zoledronic acid, Zolinza, Zometa®.

Routes of Administration

Antibodies, antigen binding fragments, polypeptides and other therapeutic agents, medicaments and pharmaceutical compositions according to aspects of the present invention may be formulated for administration by a number of routes, including but not limited to, parenteral, intravenous, intra-arterial, intramuscular, subcutaneous, intradermal, intratumoral and oral. Antibodies, antigen binding fragments, polypeptides and other therapeutic agents, may be formulated in fluid or solid form. Fluid formulations may be formulated for administration by injection to a selected region of the human or animal body.

Dosage Regime

Multiple doses of the antibody, antigen binding fragment or polypeptide may be provided. One or more, or each, of the doses may be accompanied by simultaneous or sequential administration of another therapeutic agent.

Multiple doses may be separated by a predetermined time interval, which may be selected to be one of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days, or 1, 2, 3, 4, 5, or 6 months. By way of example, doses may be given once every 7, 14, 21 or 28 days (plus or minus 3, 2, or 1 days).

Kits

In some aspects of the present invention a kit of parts is provided. In some embodiments the kit may have at least one container having a predetermined quantity of the antibody, antigen binding fragment or polypeptide. The kit may provide the antibody, antigen binding fragment or polypeptide in the form of a medicament or pharmaceutical composition, and may be provided together with instructions for administration to a patient in order to treat a specified disease or condition. The antibody, antigen binding fragment or polypeptide may be formulated so as to be suitable for injection or infusion to a tumor or to the blood.

In some embodiments the kit may further comprise at least one container having a predetermined quantity of another therapeutic agent (e.g. anti-infective agent or chemotherapy agent). In such embodiments, the kit may also comprise a second medicament or pharmaceutical composition such that the two medicaments or pharmaceutical compositions may be administered simultaneously or separately such that they provide a combined treatment for the specific disease or condition. The therapeutic agent may also be formulated so as to be suitable for injection or infusion to a tumor or to the blood.

Subjects

The subject to be treated may be any animal or human. The subject is preferably mammalian, more preferably human. The subject may be a non-human mammal, but is more preferably human. The subject may be male or female. The subject may be a patient. A subject may have been diagnosed with a disease or condition requiring treatment, or be suspected of having such a disease or condition.

Protein Expression

Molecular biology techniques suitable for the producing polypeptides according to the invention in cells are well known in the art, such as those set out in Sambrook et al., Molecular Cloning: A Laboratory Manual, New York: Cold Spring Harbor Press, 1989

The polypeptide may be expressed from a nucleotide sequence. The nucleotide sequence may be contained in a vector present in a cell, or may be incorporated into the genome of the cell.

A "vector" as used herein is an oligonucleotide molecule (DNA or RNA) used as a vehicle to transfer exogenous genetic material into a cell. The vector may be an expression vector for expression of the genetic material in the cell. Such vectors may include a promoter sequence operably linked to the nucleotide sequence encoding the gene sequence to be expressed. A vector may also include a termination codon and expression enhancers. Any suitable vectors, promoters, enhancers and termination codons known in the art may be used to express polypeptides from a vector according to the invention. Suitable vectors include plasmids, binary vectors, viral vectors and artificial chromosomes (e.g. yeast artificial chromosomes).

In this specification the term "operably linked" may include the situation where a selected nucleotide sequence and regulatory nucleotide sequence (e.g. promoter and/or enhancer) are covalently linked in such a way as to place the expression of the nucleotide sequence under the influence or control of the regulatory sequence (thereby forming an expression cassette). Thus a regulatory sequence is operably linked to the selected nucleotide sequence if the regulatory sequence is capable of effecting transcription of the nucleotide sequence. Where appropriate, the resulting transcript may then be translated into a desired protein or polypeptide.

Any cell suitable for the expression of polypeptides may be used for producing peptides according to the invention. The cell may be a prokaryote or eukaryote. Suitable prokaryotic cells include *E. coli*. Examples of eukaryotic cells include a yeast cell, a plant cell, insect cell or a mammalian cell. In some cases the cell is not a prokaryotic cell because some prokaryotic cells do not allow for the same post-translational modifications as eukaryotes. In addition, very high expression levels are possible in eukaryotes and proteins can be easier to purify from eukaryotes using appropriate tags. Specific plasmids may also be utilised which enhance secretion of the protein into the media.

Methods of producing a polypeptide of interest may involve culture or fermentation of a cell modified to express the polypeptide. The culture or fermentation may be performed in a bioreactor provided with an appropriate supply of nutrients, air/oxygen and/or growth factors. Secreted proteins can be collected by partitioning culture media/fermentation broth from the cells, extracting the protein content, and separating individual proteins to isolate secreted polypeptide. Culture, fermentation and separation techniques are well known to those of skill in the art.

Bioreactors include one or more vessels in which cells may be cultured. Culture in the bioreactor may occur continuously, with a continuous flow of reactants into, and a continuous flow of cultured cells from, the reactor. Alternatively, the culture may occur in batches. The bioreactor monitors and controls environmental conditions such as pH, oxygen, flow rates into and out of, and agitation within the vessel such that optimum conditions are provided for the cells being cultured.

Following culture of cells that express the polypeptide of interest, that polypeptide is preferably isolated. Any suitable method for separating polypeptides/proteins from cell culture known in the art may be used. In order to isolate a polypeptide/protein of interest from a culture, it may be necessary to first separate the cultured cells from media containing the polypeptide/protein of interest. If the polypeptide/protein of interest is secreted from the cells, the cells may be separated from the culture media that contains the secreted polypeptide/protein by centrifugation. If the polypeptide/protein of interest collects within the cell, it will be necessary to disrupt the cells prior to centrifugation, for example using sonification, rapid freeze-thaw or osmotic lysis. Centrifugation will produce a pellet containing the cultured cells, or cell debris of the cultured cells, and a supernatant containing culture medium and the polypeptide/protein of interest.

It may then be desirable to isolate the polypeptide/protein of interest from the supernatant or culture medium, which may contain other protein and non-protein components. A common approach to separating polypeptide/protein components from a supernatant or culture medium is by precipitation. Polypeptides/proteins of different solubility are precipitated at different concentrations of precipitating agent such as ammonium sulfate. For example, at low concentrations of precipitating agent, water soluble proteins are extracted. Thus, by adding increasing concentrations of precipitating agent, proteins of different solubility may be distinguished. Dialysis may be subsequently used to remove ammonium sulfate from the separated proteins.

Other methods for distinguishing different polypeptides/proteins are known in the art, for example ion exchange chromatography and size chromatography. These may be used as an alternative to precipitation, or may be performed subsequently to precipitation.

Once the polypeptide/protein of interest has been isolated from culture it may be necessary to concentrate the protein. A number of methods for concentrating a protein of interest are known in the art, such as ultrafiltration or lyophilisation.

Sequence Identity

Alignment for purposes of determining percent amino acid or nucleotide sequence identity can be achieved in various ways known to a person of skill in the art, for instance, using publicly available computer software such as ClustalW 1.82. T-coffee or Megalign (DNASTAR) software. When using such software, the default parameters, e.g. for gap penalty and extension penalty, are preferably used. The default parameters of ClustalW 1.82 are: Protein Gap Open Penalty=10.0, Protein Gap Extension Penalty=0.2, Protein matrix=Gonnet, Protein/DNA ENDGAP=−1, Protein/DNA GAPDIST=4.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

BRIEF DESCRIPTION OF THE FIGURES

Embodiments and experiments illustrating the principles of the invention will now be discussed with reference to the accompanying figures in which:

FIG. 1A. Light chain variable domain sequences for anti-PD-1 antibody clone A3. CDRs are underlined and shown separately.

FIG. 1B. Light chain variable domain sequences for anti-PD-1 antibody clone A10. CDRs are underlined and shown separately.

FIG. 1C. Light chain variable domain sequences for anti-PD-1 antibody clone B6. CDRs are underlined and shown separately.

FIG. 1D. Light chain variable domain sequences for anti-PD-1 antibody clone C4. CDRs are underlined and shown separately.

FIG. 1E. Light chain variable domain sequences for anti-PD-1 antibody clone D4. CDRs are underlined and shown separately.

FIG. 1F. Light chain variable domain sequences for anti-PD-1 antibody clone E1. CDRs are underlined and shown separately.

FIG. 1G. Light chain variable domain sequences for anti-PD-1 antibody clone F2. CDRs are underlined and shown separately.

FIG. 1H. Light chain variable domain sequences for anti-PD-1 antibody clone G1. CDRs are underlined and shown separately.

FIG. 1I. Light chain variable domain sequences for anti-PD-1 antibody clone G2. CDRs are underlined and shown separately.

FIG. 1J. Light chain variable domain sequences for anti-PD-1 antibody clone G10. CDRs are underlined and shown separately.

FIG. 1K. Light chain variable domain sequences for anti-PD-1 antibody clone H4. CDRs are underlined and shown separately.

FIG. 1L. Light chain variable domain sequences for anti-PD-1 antibody clone H9 (human IgG4). CDRs are underlined and shown separately.

FIG. 2A. Heavy chain variable domain sequences for anti-PD-1 antibody A3. CDRs are underlined and shown separately.

FIG. 2B. Heavy chain variable domain sequences for anti-PD-1 antibody A10. CDRs are underlined and shown separately.

FIG. 2C. Heavy chain variable domain sequences for anti-PD-1 antibody B6. CDRs are underlined and shown separately.

FIG. 2D. Heavy chain variable domain sequences for anti-PD-1 antibody C4. CDRs are underlined and shown separately.

FIG. 2E. Heavy chain variable domain sequences for anti-PD-1 antibody D4. CDRs are underlined and shown separately.

FIG. 2F. Heavy chain variable domain sequences for anti-PD-1 antibody E1. CDRs are underlined and shown separately.

FIG. 2G. Heavy chain variable domain sequences for anti-PD-1 antibody F2. CDRs are underlined and shown separately.

FIG. 2H. Heavy chain variable domain sequences for anti-PD-1 antibody G1. CDRs are underlined and shown separately.

FIG. 2I. Heavy chain variable domain sequences for anti-PD-1 antibody G2. CDRs are underlined and shown separately.

FIG. 2J. Heavy chain variable domain sequences for anti-PD-1 antibody G10. CDRs are underlined and shown separately.

FIG. 2K. Heavy chain variable domain sequences for anti-PD-1 antibody H4. CDRs are underlined and shown separately.

FIG. 2L. Heavy chain variable domain sequences for anti-PD-1 antibody H9. (human igG4). CDRs are underlined and shown separately.

FIG. 3A. Table showing light chain CDR sequences for anti-PD-1 antibody clones A3, A10, B6, C4, D4, E1, F2, G1, G2, G10, H4, H9.

FIG. 3B. Table showing heavy chain CDR sequences for anti-PD-1 antibody clones A3, A10, B6, C4, D4, E1, F2, G1.

FIG. 3C. Table showing heavy chain CDR sequences for anti-PD-1 antibody clones G2, G10, H4, H9.

FIG. 4A. Nucleotide and encoded amino acid sequences of light chain variable domain sequences for anti-PD-1 antibody clones A3 and A10.

FIG. 4B. Nucleotide and encoded amino acid sequences of light chain variable domain sequences for anti-PD-1 antibody clones optimised A10, B6 and optimised B6.

FIG. 4C. Nucleotide and encoded amino acid sequences of light chain variable domain sequences for anti-PD-1 antibody clones C4, optimized C4 and D4.

FIG. 4D. Nucleotide and encoded amino acid sequences of light chain variable domain sequences for anti-PD-1 antibody clones E1 and F2.

FIG. 4E. Nucleotide and encoded amino acid sequences of light chain variable domain sequences for anti-PD-1 antibody clones G1 and G2.

FIG. 4F. Nucleotide and encoded amino acid sequences of light chain variable domain sequences for anti-PD-1 antibody clones G10 and H4.

FIG. 4G. Nucleotide and encoded amino acid sequences of light chain variable domain sequences for anti-PD-1 antibody clones optimised H4 and H9 (human IgG4).

FIG. 4H. Nucleotide and encoded amino acid sequences of heavy chain variable domain sequences for anti-PD-1 antibody clones A3 and A10.

FIG. 4I. Nucleotide and encoded amino acid sequences of heavy chain variable domain sequences for anti-PD-1 antibody clones optimised A10 and B6.

FIG. 4J. Nucleotide and encoded amino acid sequences of heavy chain variable domain sequences for anti-PD-1 antibody clones optimised B6, C4 and optimised C4.

FIG. 4K. Nucleotide and encoded amino acid sequences of heavy chain variable domain sequences for anti-PD-1 antibody clones D4 and E1.

FIG. 4L. Nucleotide and encoded amino acid sequences of heavy chain variable domain sequences for anti-PD-1 antibody clones F2 and G1.

FIG. 4M. Nucleotide and encoded amino acid sequences of heavy chain variable domain sequences for anti-PD-1 antibody clones G2 and G10.

FIG. 4N. Nucleotide and encoded amino acid sequences of heavy chain variable domain sequences for anti-PD-1 antibody clones H4, optimised H4 and H9 (human IgG4).

FIG. 5. Table showing binding affinity ($K_D$, nM) of clones A3, A10, B6, C4, D4, E1, F2, G1, G2, G10, H4 and H9, and control antibodies nivolumab and lambrolizumab for human PD-1.

FIG. 23A. Chart showing the expression of exhaustion markers PD-1, PD-L1, TIM-3, LAG-3 and CTLA4 by bladder tumour infiltrating lymphocytes. A majority of tumour infiltrating lymphocytes express PD-1, while only a minority of PBMC lymphocytes express PD-1.

EXAMPLES

The inventors described in the following Examples the identification of nucleotide and amino-acid sequences of isolated antibodies, or the antigen-binding portions thereof, that specifically bind human and rhesus PD-1, block the PD-1 pathway and restore exhausted T cell activity.

Isolation of Anti-Human PD-1 Antibodies

Anti-PD-1 antibodies were isolated from a human antibody phage display library via in vitro selection in a 4-round bio-panning process.

Streptavidin-magnetic beads were coated with biotinylated human PD-1 and used to fish-out anti-PD-1-specific phages using magnetic sorting. Some steps to remove of potential anti-biotin antibodies were added in the selection process.

Specific Fab antibodies were originally identified by ELISA with human-PD-1 as the antigen. A first clonality screening was performed by DNA fingerprinting; clonality was then confirmed by sequencing.

Affinity Maturation

Selected antibodies went through affinity maturation by CDR engineering. Selection of specific anti-PD-1 antibodies was conducted by phage display. More than 80 affinity-matured clones with ~100-fold improved affinity were generated. To select clones, thermostability assays were conducted. Antibodies were heated and their stability monitored based on their ability to bind human PD-1 in ELISA. Clones still stable at 71° C. were kept for further analyses, their affinity for human PD-1 was measured using a ProteOn bioanalyser (Biorad). Briefly, human-PD-1 coupled to Fc was immobilised on a sensor chip and a flow of antibody was applied; association and dissociation rates were measured and the affinity ($K_D$) calculated. Twelve of the affinity-matured clones were designated A3, A10, B6, C4, D4, E1, F2, G1, G2, G10, H4 and H9.

Affinity of the Isolated Anti-PD-1 Antibodies

Affinity of A3, A10, B6, C4, D4, E1, F2, G1, G2, G10, H4 and H9 for human PD-1 was measured by Surface Plasmon Resonance and compared to the affinity of nivolumab and lambrolizumab, two anti-PD-1 antibodies in late clinical development stage (FIG. 5).

Briefly, human or mouse PD-1 coupled to human Fc was immobilised on a sensor chip compatible with the Proteon XPR36 bioanalyser (Biorad). Crude Fab extracts (or the control antibodies) were then flown onto the chip and the association/dissociation of each candidate Fab was then recorded and analysed, the affinity ($K_D$) was calculated.

A3, A10, B6, C4, D4, E1, F2, G1, G2, G10, H4 and H9 show affinity in the range 0.1 to 0.7 nM while nivolumab and lambrolizumab exhibit $K_D$ of 1.9 and 0.5 nM respectively (FIG. 5).

Figure 6:
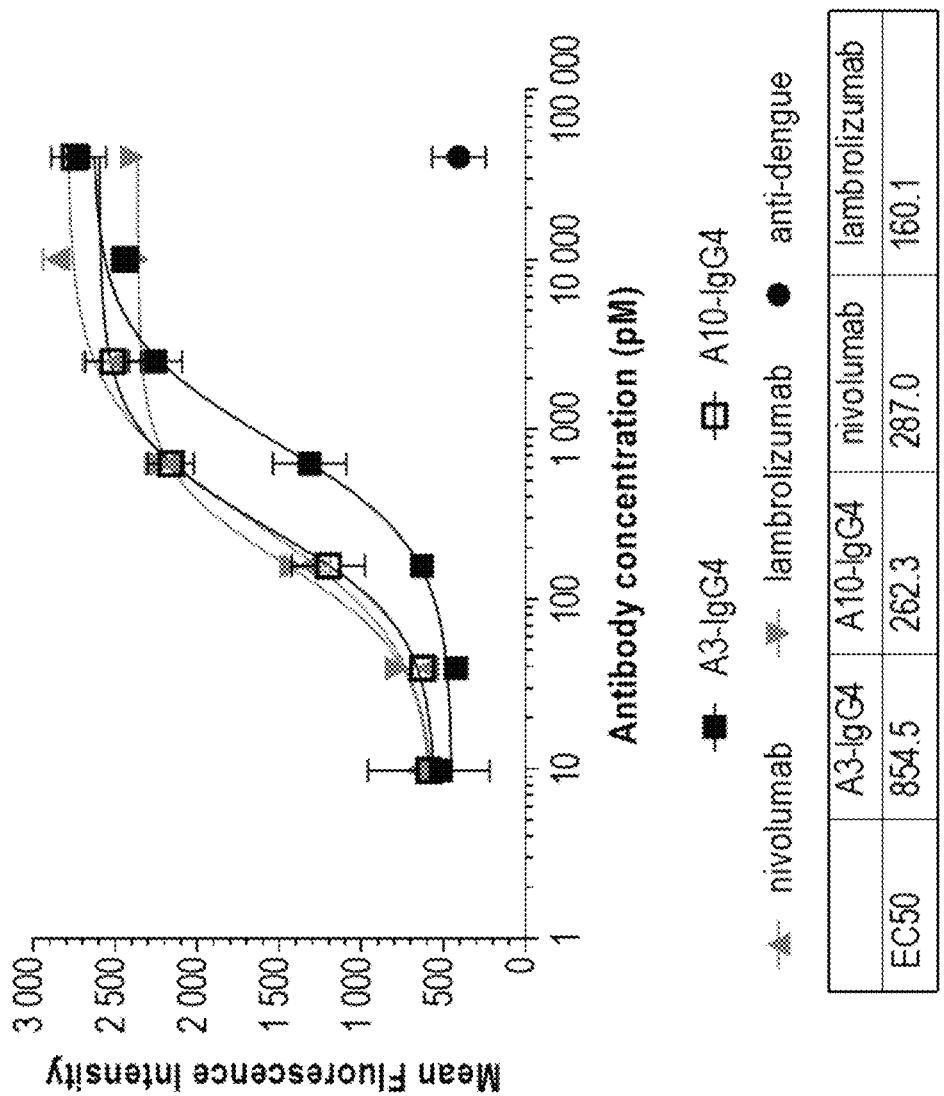
FIG. 6. Chart showing binding of anti-human PD-1 antibodies A3, A10, nivolumab and lambrolizumab to activated T cells.
Figure 7:
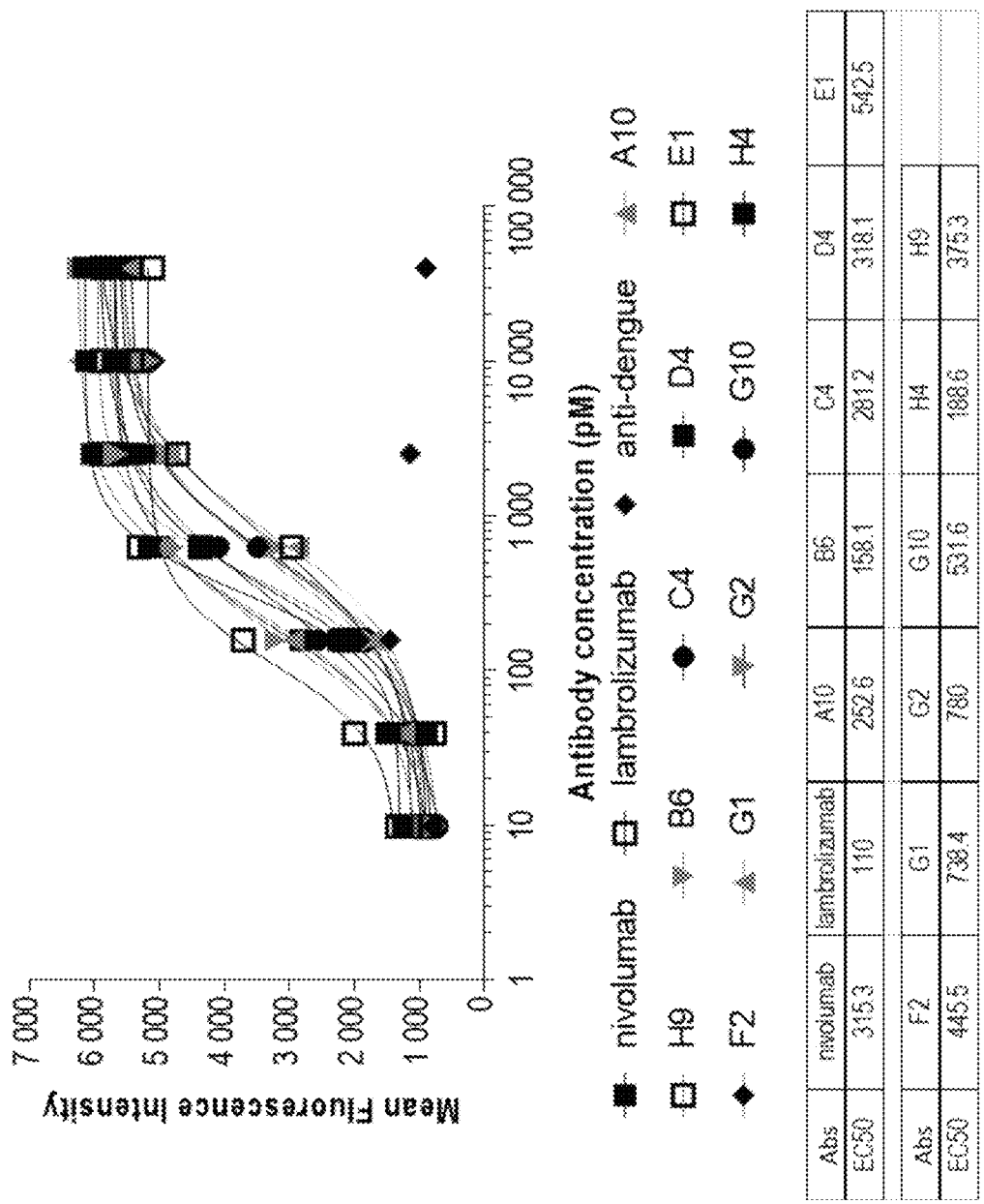
FIG. 7. Chart showing binding of anti-human PD-1 antibodies A10, B6, C4, D4, E1, F2, G1, G2, G10, H4 and H9, nivolumab and lambrolizumab to activated T cells.

Characterisation of the Anti-Human PD-1 Antibodies:
Binding to PD-1 Expressing Cells 50,000 T cells isolated from a healthy donor were incubated in the presence of 5,000 monocyte-derived DCs from another donor for 7 days at 37° C. Antibodies, expressed as IgG4, were incubated with such activated T cells for 30 minutes in PBS. After a wash in PBS, a fluorescent labelled secondary antibody was added for 30 minutes and then washed in PBS. Cells were resuspended in FACS buffer and binding of the antibody to the cells was monitored by flow cytometry (FIGS. 6 and 7).

Cross-Reactivity with Rhesus PD-1

Figure 8:
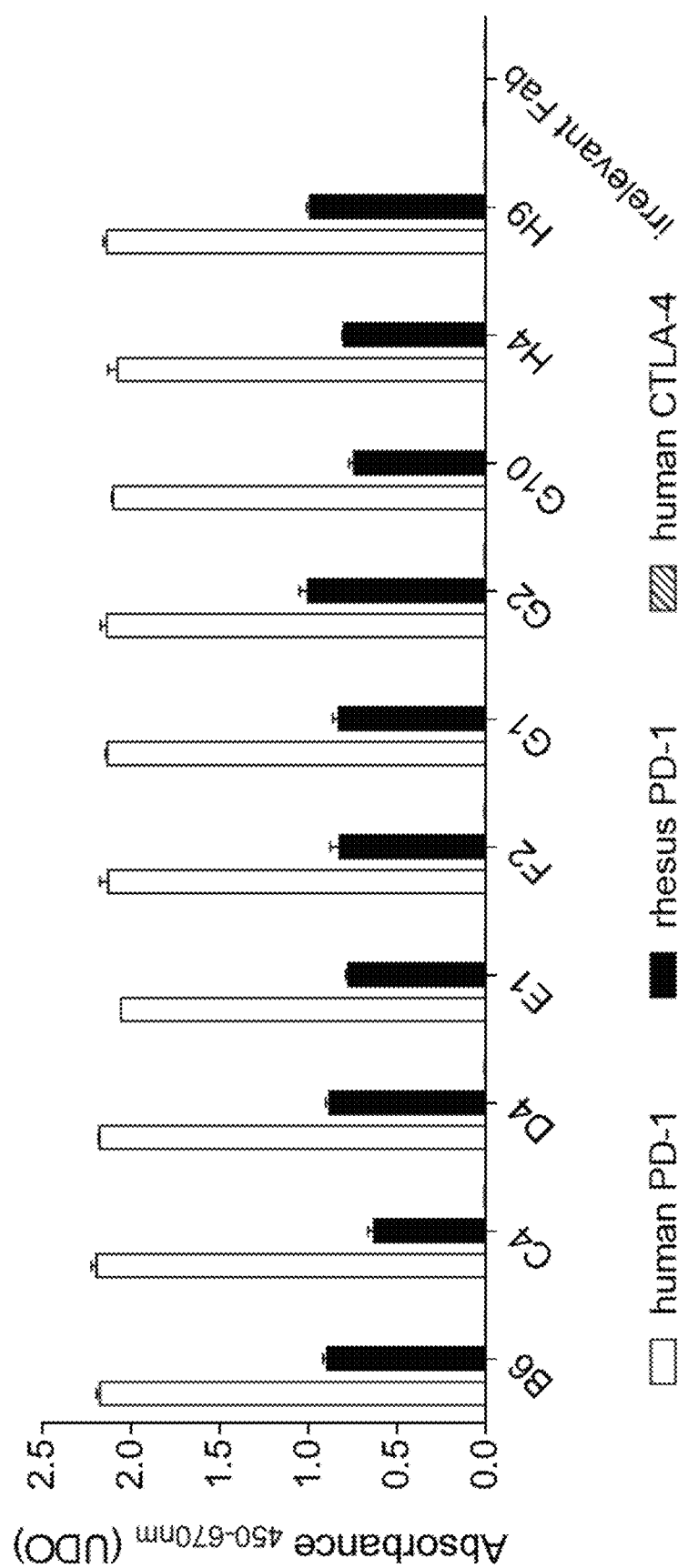
FIG. 8. Chart showing reactivity of clones B6, C4, D4, E1, F2, G1, G2, G10, H4 and H9 with human PD-1, rhesus PD-1 and human CTLA-4.
Figure 9:
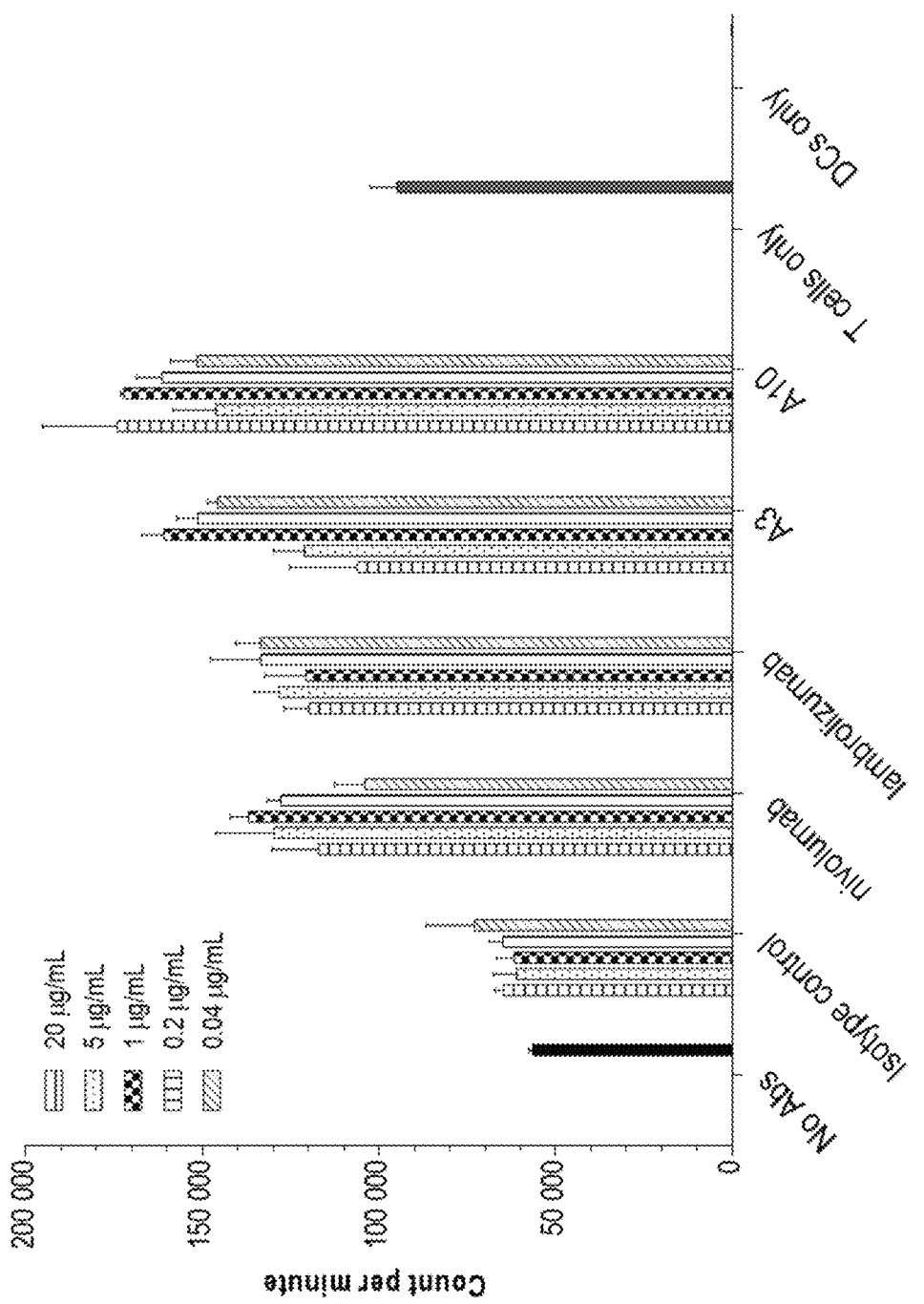
FIG. 9. Chart showing allogeneic CD4$^+$ T cell proliferation of exhausted T cells in response to antibodies A3, A10, nivolumab, lambrolizumab.
Figure 10:
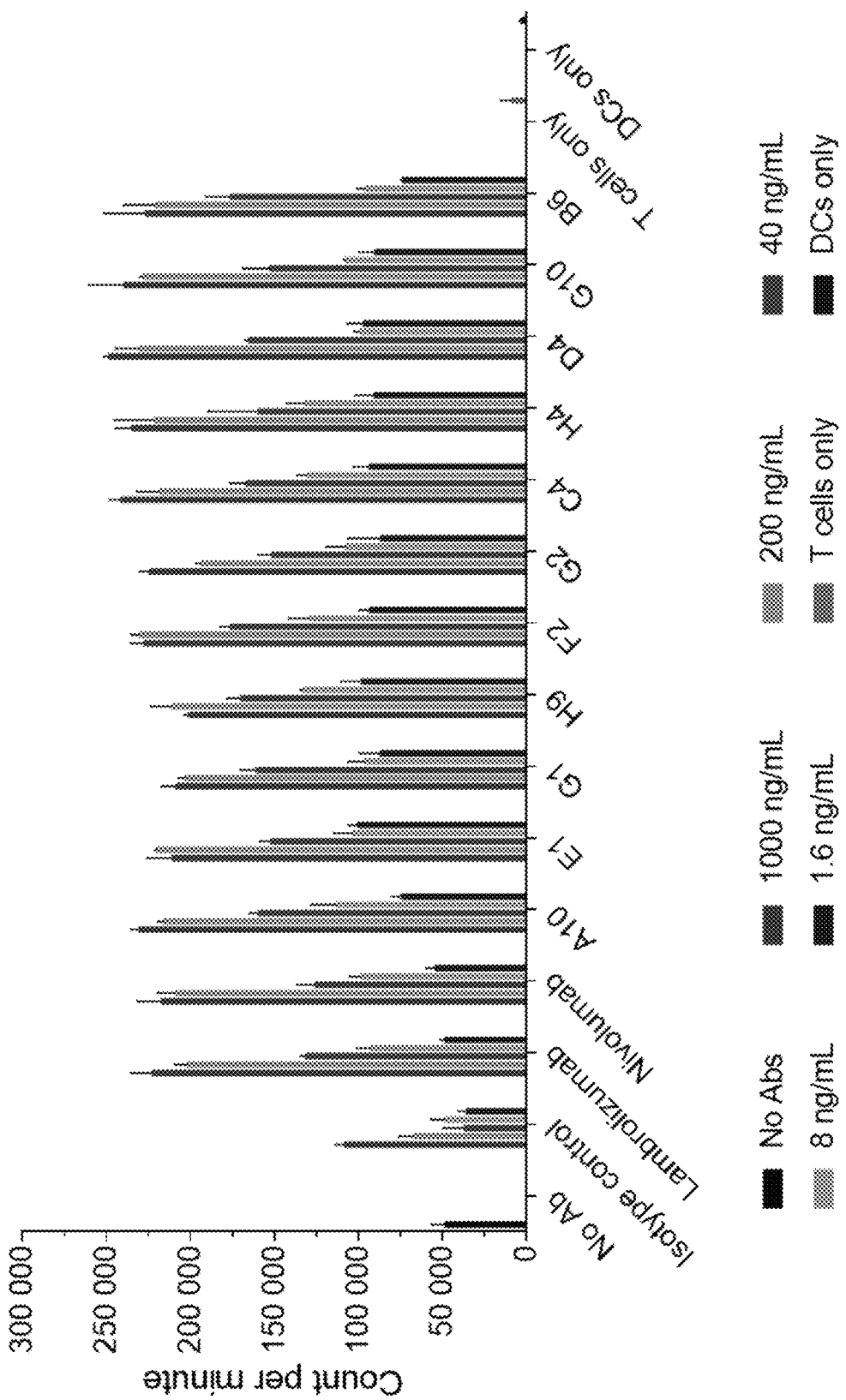
FIG. 10. Chart showing allogeneic CD4$^+$ T cell proliferation of exhausted T cells in response to antibodies A10, B6, C4, D4, E1, F2, G1, G2, G10, H4, H9, nivolumab, lambrolizumab.
Figure 11:
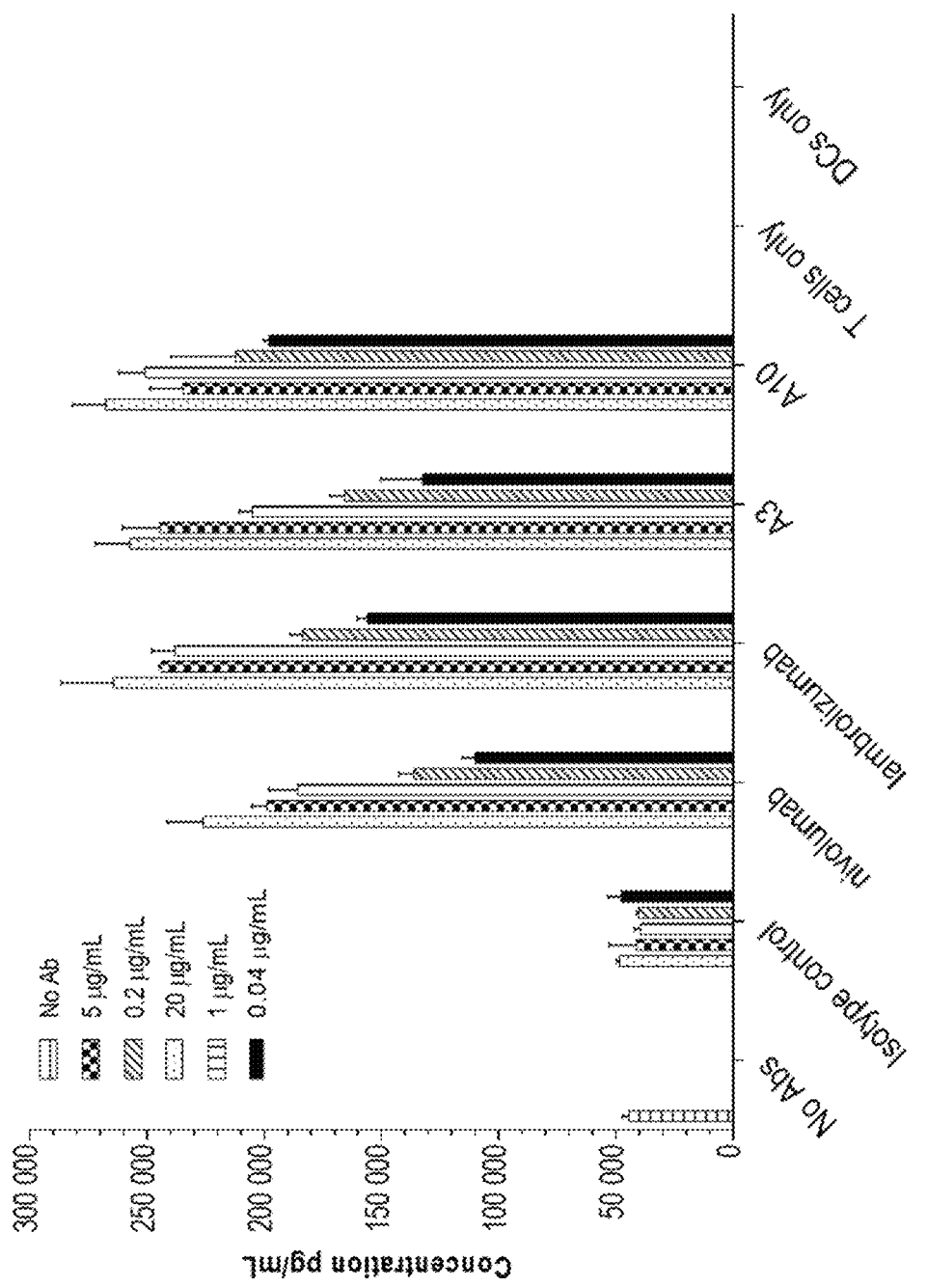
FIG. 11. Chart showing IFNγ secretion of exhausted T cells in response to antibodies A3, A10, nivolumab, lambrolizumab.
Figure 12:
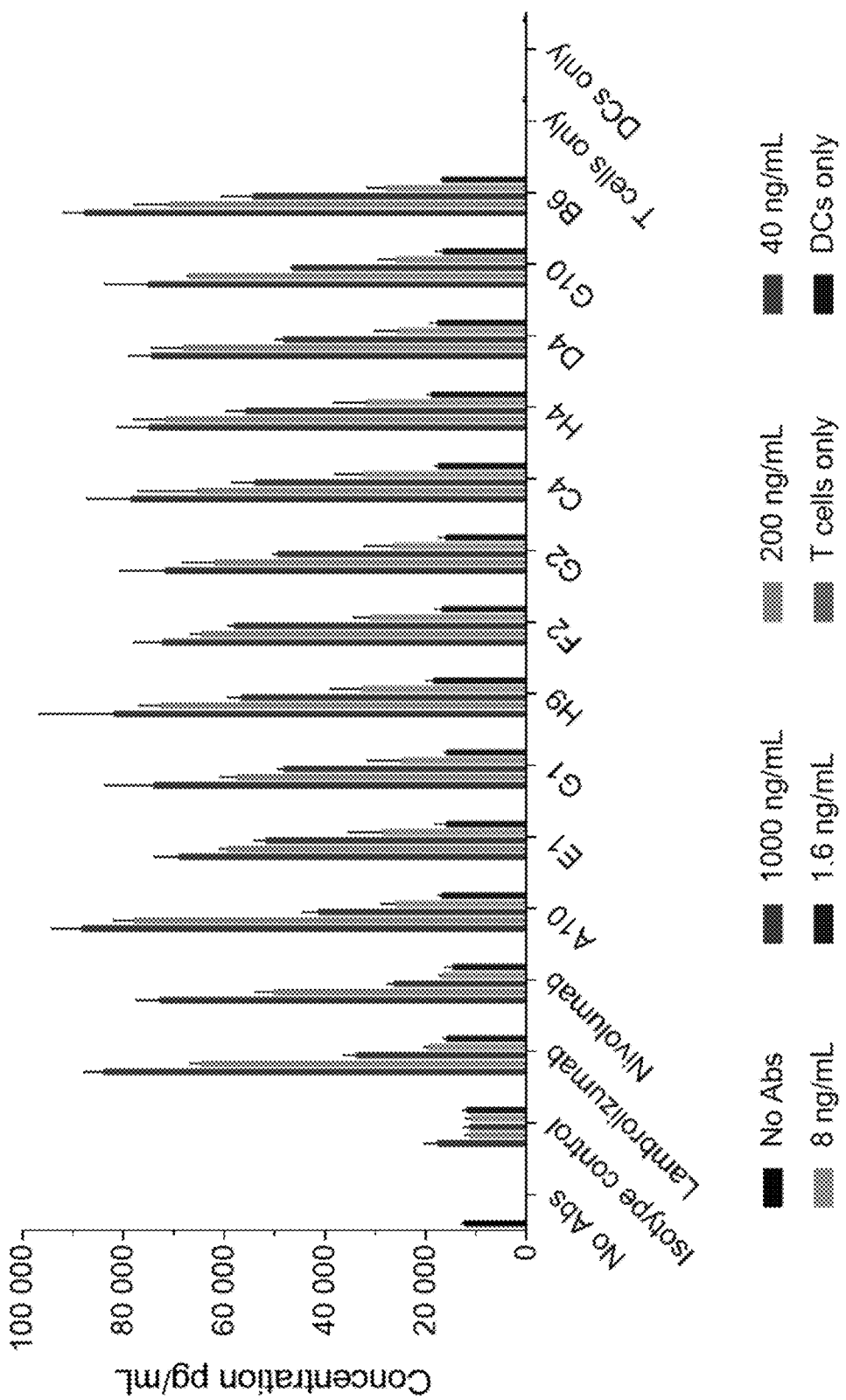
FIG. 12. Chart showing IFNγ secretion of exhausted T cells in response to antibodies A10, B6, C4, D4, E1, F2, G1, G2, G10, H4, H9, nivolumab, lambrolizumab.

Affinity-matured clone Fabs were tested in ELISA for recognition of rhesus PD-1. Briefly, ELISA plates were coated with 350 ng/well of human or rhesus PD-1 in carbonate buffer and then blocked with a solution of casein. After extensive washes in PBS Tween-20, antibody-containing supernatants were transferred into the ELISA plates in the presence of 7% milk in PBS. After 90 minutes at room temperature under agitation and extensive washes, a goat anti-human Fab antibody coupled to HRP was added. One hour later, plates were washed and TMB substrate added. The reaction was stopped with 1M HCl and optical density measured at 450 nm with a reference at 670 nm (FIG. 8).

In Vitro Functional Activity

Anti-PD-1 antibodies were tested in a functional assay measuring 2 activity parameters of T cells: proliferation and secretion of IFN-γ. Briefly, T cells were isolated from a healthy donor and cultured for 7 days in the presence of monocyte-derived dendritic cells from another donor (50,000 Tcells/5,000 DCs). This continuous stimulation induces exhaustion of the T cells. Antibodies were then added to the cultures for 5 more days. After 4 days, supernatants were collected to measure IFN-γ by ELISA, and T cells were cultured for 4 days, with addition of 1 μCi of tritiated thymidine for the last 18 hours. Cells were then harvested and proliferation measured with a β-counter.

Clones A3, A10, B6, C4, D4, E1, F2, G1, G2, G10, H4 and H9 are able to restore proliferation of previously exhausted T cells and to restore their ability to secrete IFN-γ (FIGS. 9 to 12).

Specificity for PD-1

Anti-PD-1 antibodies were tested in an ELISA assay for their ability to bind to other members of the CD28 family.

Briefly, ELISA plates were coated with 350 ng/well of one of the following antigens coupled to human Fc in carbonate buffer: human PD-1, human PD-L1, human TIM-3, human LAG-3, human ICOS, human CTLA4, human BTLA, human CD28, mouse TIM-3, or rhesus PD-1. The plate was then blocked with a solution of casein. After extensive washes in PBS Tween-20, antibodies were added into the ELISA wells in the presence of 7% milk in PBS. After 90 minutes at room temperature under agitation and extensive washes, a goat anti-human Fab antibody coupled to HRP was added. One hour later, plates were washed and TMB substrate added. The reaction was stopped with 1M HCl and optical density measured at 450 nm with a reference at 670 nm.

Figure 13:
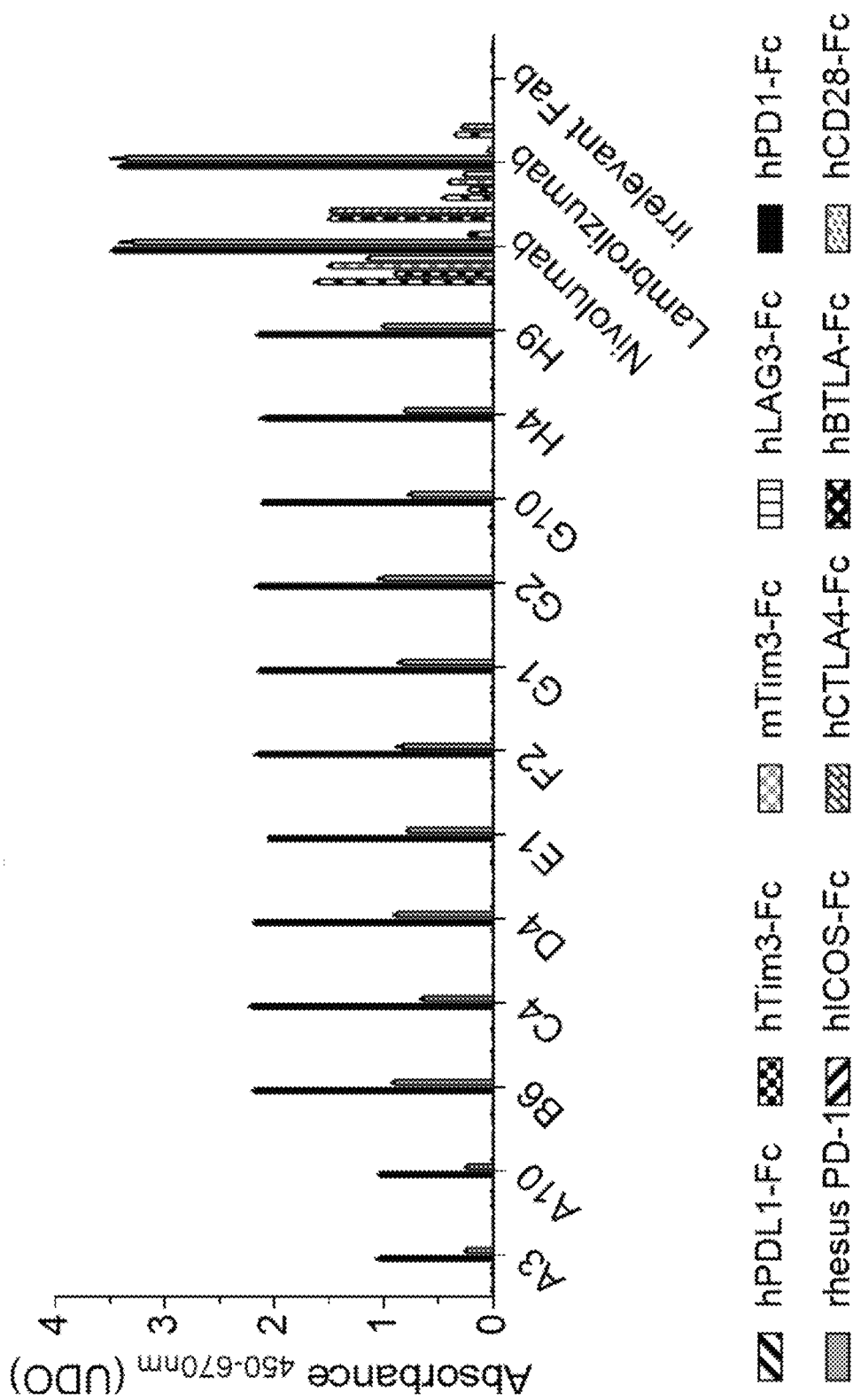
FIG. 13. Chart showing specificity of binding of antibodies A3, A10, B6, C4, D4, E1, F2, G1, G2, G10, H4, H9, for human and rhesus-PD-1 over other human (h) or murine (m) CD28 family members compared with nivolumab, and lambrolizumab, as determined by ELISA.

While nivolumab cross-binds to PD-L1, TIM-3, LAG-3, BTLA and CD28 (and lambrolizumab in a very weak manner too), 1D11 and 1G4 are specific to PD-1 only; showing only a very weak cross-recognition of other members than PD-1 (FIG. 13).

Production Yield

HEK-293.6E cells were transiently transfected to produce anti-PD-1 antibodies in IgG4 format; production yield in this system was compared.

| Antibody | Production yield (mg/L) |
| --- | --- |
| Lambrolizumab | 2.1 |
| A3 | 9.9 |
| A10 | 32.1 |
| E1 | 30.6 |
| F2 | 32.6 |
| G1 | 30.8 |
| G2 | 28.8 |
| H9 | 18.4 |
| D4 | 26.9 |
| B6 | 26.5 |
| C4 | 27.4 |
| H4 | 19.8 |
| G10 | 33.6 |

All novel antibody clones showed better production yield than lambrolizumab.

Codon Optimisation

In order to increase gene expression efficiency, A10, B6, C4 and H4 underwent codon optimisation.

Figure 14:
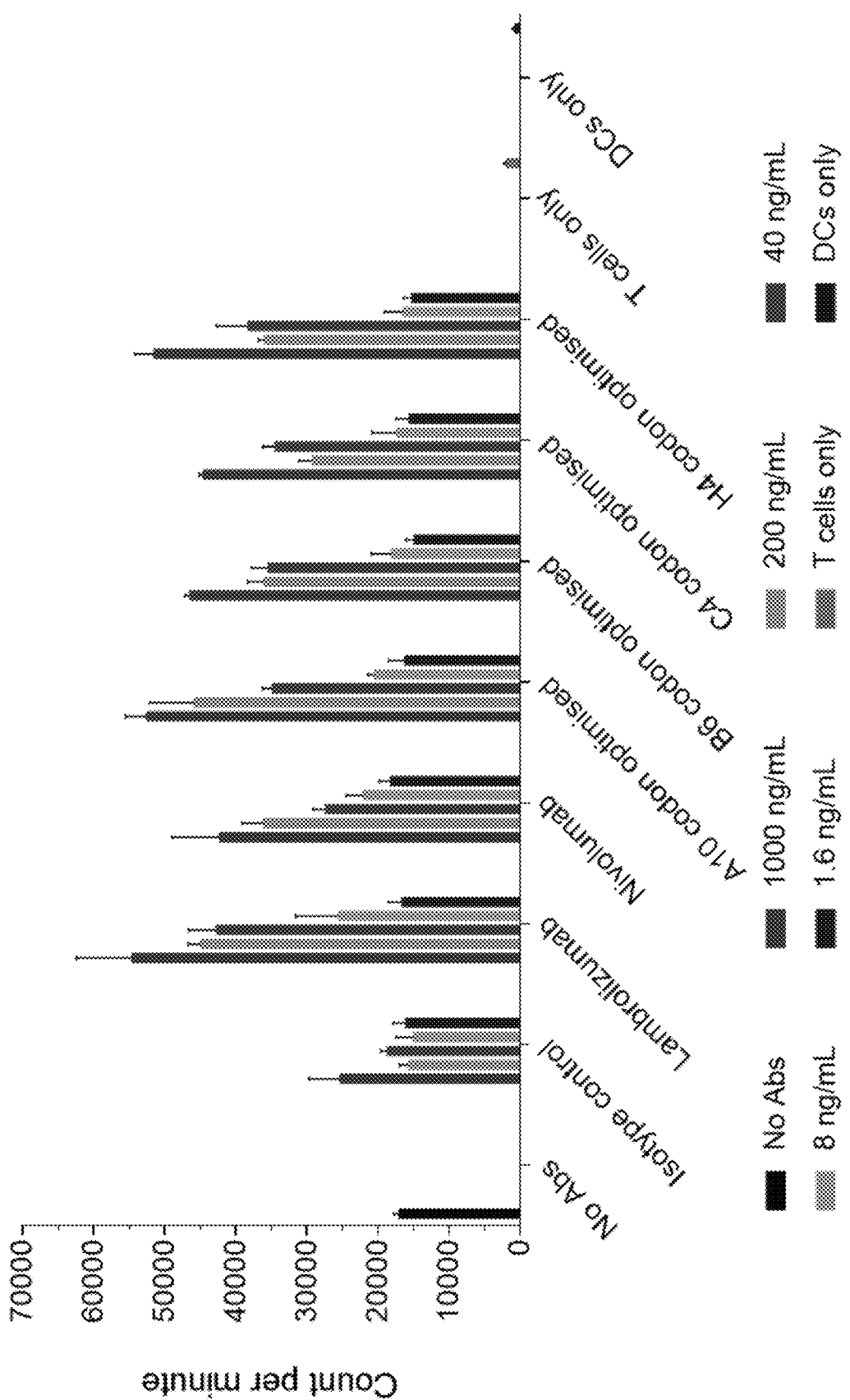
FIG. 14. Chart showing allogeneic CD4$^+$ T cell proliferation of exhausted T cells in response to antibodies A10 codon optimised, B6 codon optimised, C4 codon optimised, H4 codon optimised, nivolumab, lambrolizumab.
Figure 15:
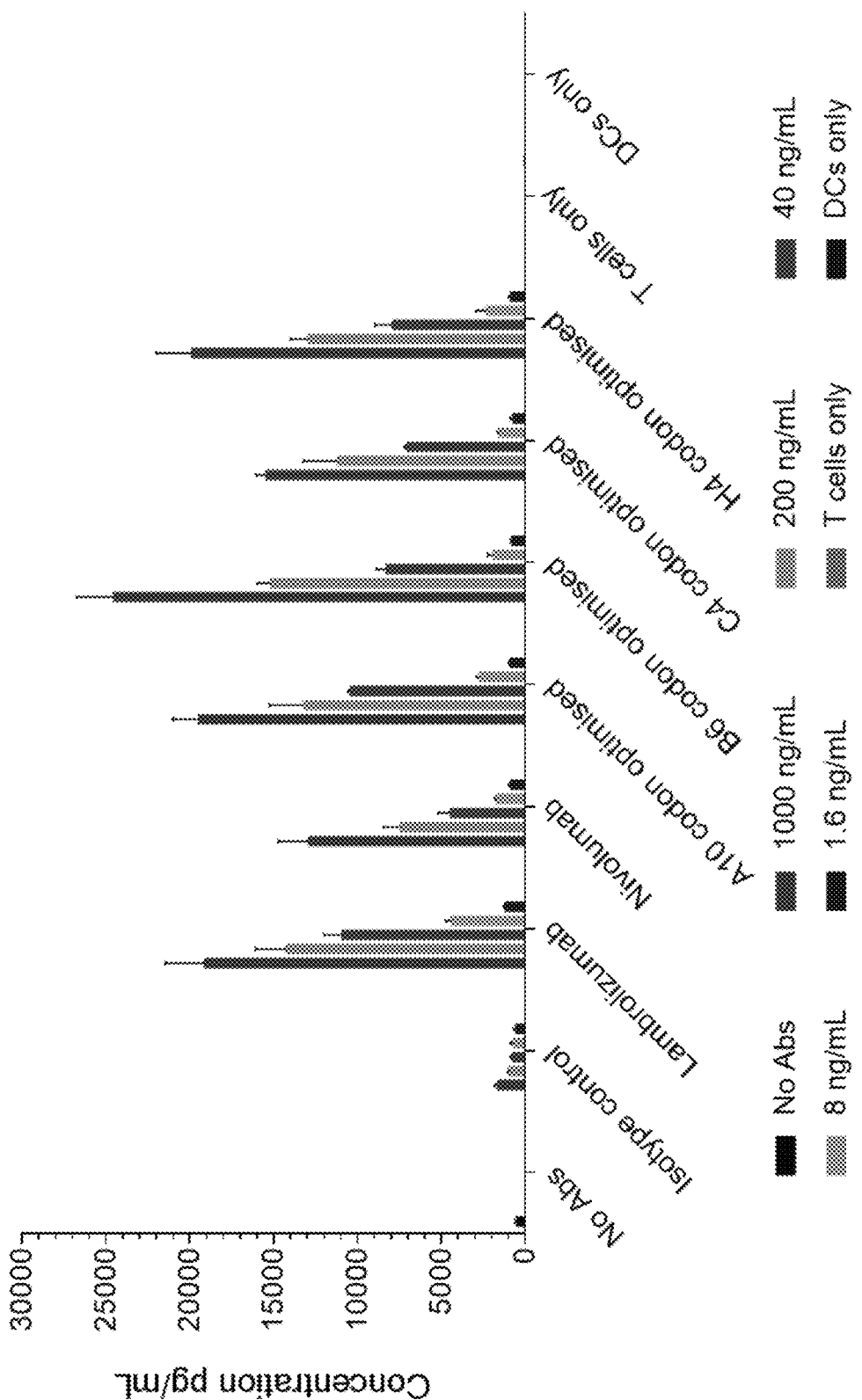
FIG. 15. Chart showing IFNγ secretion of exhausted T cells in response to antibodies A10 codon optimised, B6 codon optimised, C4 codon optimised, H4 codon optimised, nivolumab, lambrolizumab.

Codon-optimised clones retain their ability to neutralise PD-1 and restore T cell activity (T cell proliferation and IFN-γ secretion—FIGS. 14 and 15).

Use of anti-PD-1 antibodies to treat tumours: ex vivo activation of tumour infiltrating lymphocytes Lung tumour samples were obtained from the National Cancer Centre Singapore after approval by the proper IRB. Samples were dissociated using a human tumour dissociation kit and a tissue dissociator device.

Figure 16:
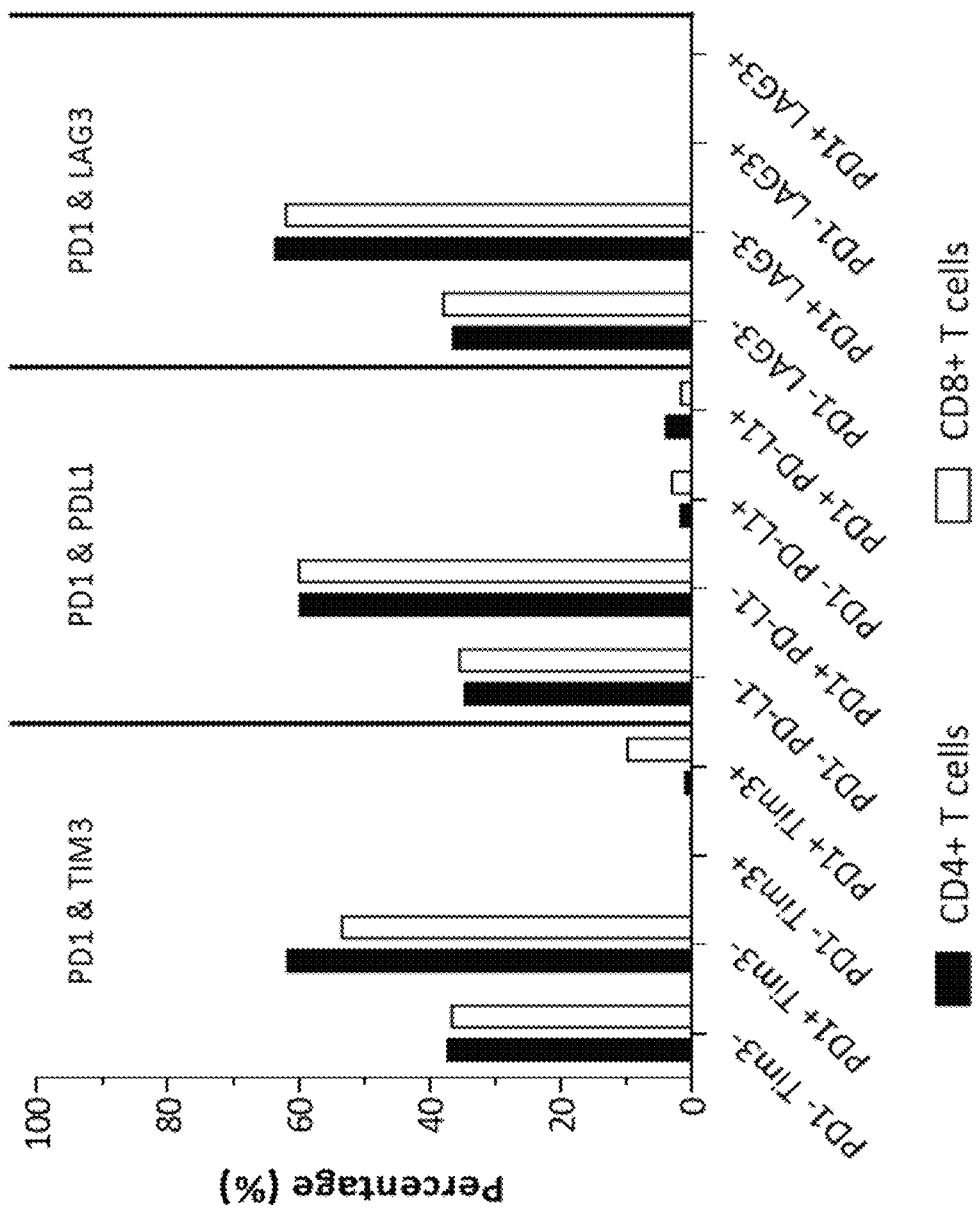
FIG. 16. Chart showing the expression of exhaustion markers PD-1, PD-L1, TIM-3 and LAG-3 by lung tumour infiltrating lymphocytes. Approximately ⅔ of CD4+ and CD8+ lymphocytes in the tumour express PD-1.

To confirm expression of exhaustion markers at the surface of the tumour infiltrating lymphocytes, isolated cell mixture was washed once and passed through 70 μm filter to obtain single cell suspension. Cells were stained with antibodies against CD4, CD8, PD-1, PD-L1, TIM-3 and LAG-3; a live/dead marker was also used to exclude dead cells from the analysis. Cells were analysed by flow cytometry. Results are shown in FIG. 16.

The tumour dissociated mixture was cultured with anti-PD-1 codon-optimised antibodies A10, B6, C4 and H4 for 7 days prior to measurement of IFN-γ in the supernatant by ELISA. Nivolumab and lambrolizumab were used as positive controls, an isotype antibody as a negative control.

Figure 17A:
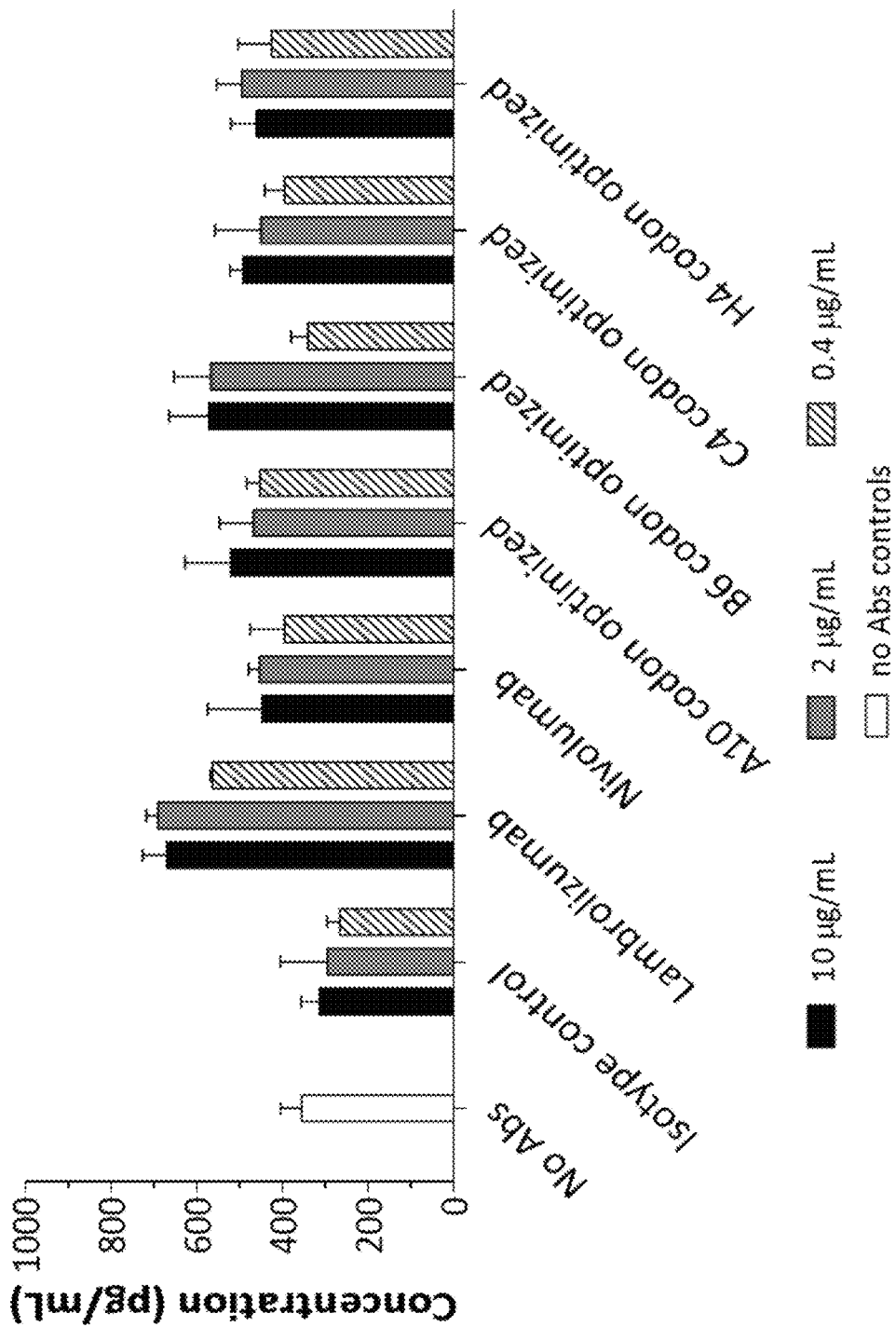
FIG. 17A. Chart showing the secretion of IFN-γ by tumour infiltrating lymphocytes after 7 days of culture in the presence or absence of anti-PD-1 antibodies (direct culture of tumour dissociated tissues).

FIG. 17A presents the secretion of IFN-γ by tumour infiltrating lymphocytes after 7 days of culture in the presence or absence of anti-PD-1 antibodies. Anti-PD-1 antibodies were able to re-activate lymphocytes to secrete IFN-γ in a dose-dependent manner.

Another fraction of the dissociated mixture was co-cultured with allogeneic dendritic cells (DCs) to initiate a mixed lymphocyte reaction (MLR). Cells were first cultured with DCs for 7 days without antibodies and then restimulated with DCs for 7 days in the presence of anti-PD-1 or control antibodies. After these 2 rounds, IFN-γ was assayed in supernatants by ELISA.

Figure 17B:
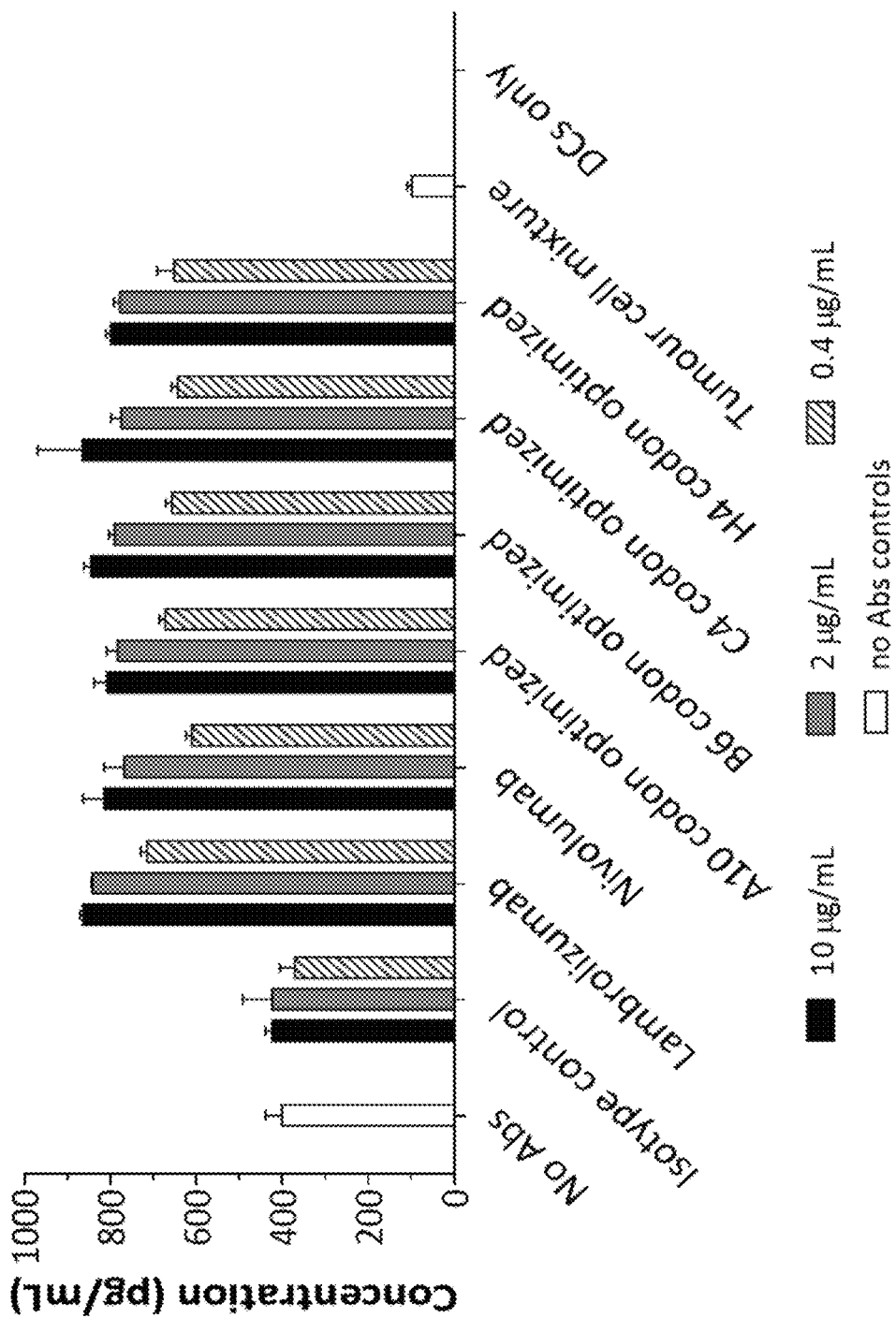
FIG. 17B. Chart showing the secretion of IFN-γ by tumour infiltrating lymphocytes after a mixed lymphocyte reaction in the presence or absence of anti-PD-1 antibodies.

FIG. 17B presents the secretion of IFN-γ after the MLR in the presence or absence of anti-PD-1 antibodies. Anti-PD-1 antibodies were able to restore the ability of lymphocytes located in the tumour site to secrete IFN-γ in a dose-dependent manner.

Use of Anti-PD-1 Antibodies to Treat Infections: Autologous Activation of T Cells in the Presence of Influenza Blood was collected from Influenza-positive donors. Monocyte-derived DCs were infected with influenza virus A/PR/8/34 (H1N1). Infected DCs were then mixed to PBMCs from the same donor for a first round of culture of 5 days. Cells were then restimulated with Influenza-infected DCs and cultured for a second round of 5 days in the presence of anti-PD-1 antibodies. After these 2 rounds, most of the cells in culture are Influenza-specific T cells. At the end of the 2 rounds of culture, IFN-γ was assayed in supernatants by ELISA.

Figure 18:
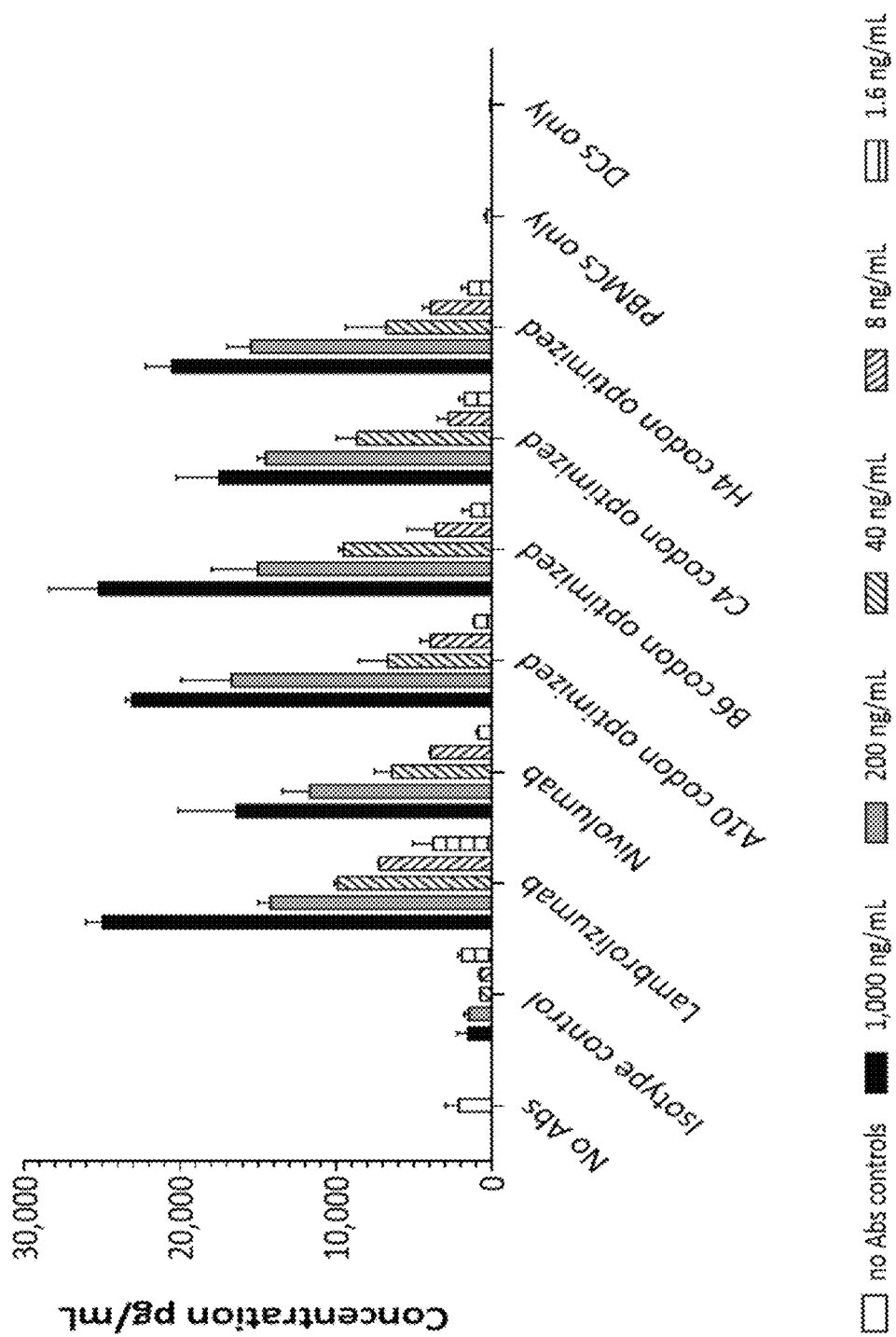
FIG. 18. Chart showing the secreted IFN-γ after culture of PBMCs with Influenza virus infected dendritic cells in the presence or absence of anti-PD-1 antibodies.

FIG. 18 presents the secreted IFN-γ after culture of PBMCs with Influenza virus infected DCs in the presence or absence of anti-PD-1 antibodies. Anti-PD-1 antibodies were able to restore the capacity of lymphocytes to secrete IFN-γ upon viral stimulation in a dose-dependent manner.

Lung Cancer: Use of Anti-PD-1 Antibodies to Re-Activate Lung Tumour Infiltrating Lymphocytes (Ex Vivo Data)

Lung tumour samples were obtained from the National Cancer Centre Singapore after approval by the proper IRB. Samples were dissociated using a human tumour dissociation kit and a tissue dissociator device.

To confirm expression of exhaustion markers at the surface of the tumour infiltrating lymphocytes, isolated cell mixture was washed once and passed through 70 μm filter to obtain single cell suspension. Cells were stained with antibodies against CD4, CD8, PD-1, PD-L1, Tim-3, LAG-3 and CTLA-4; a live/dead marker was also used to exclude dead cells from the analysis. Cells were analysed by flow cytometry.

Figure 19:
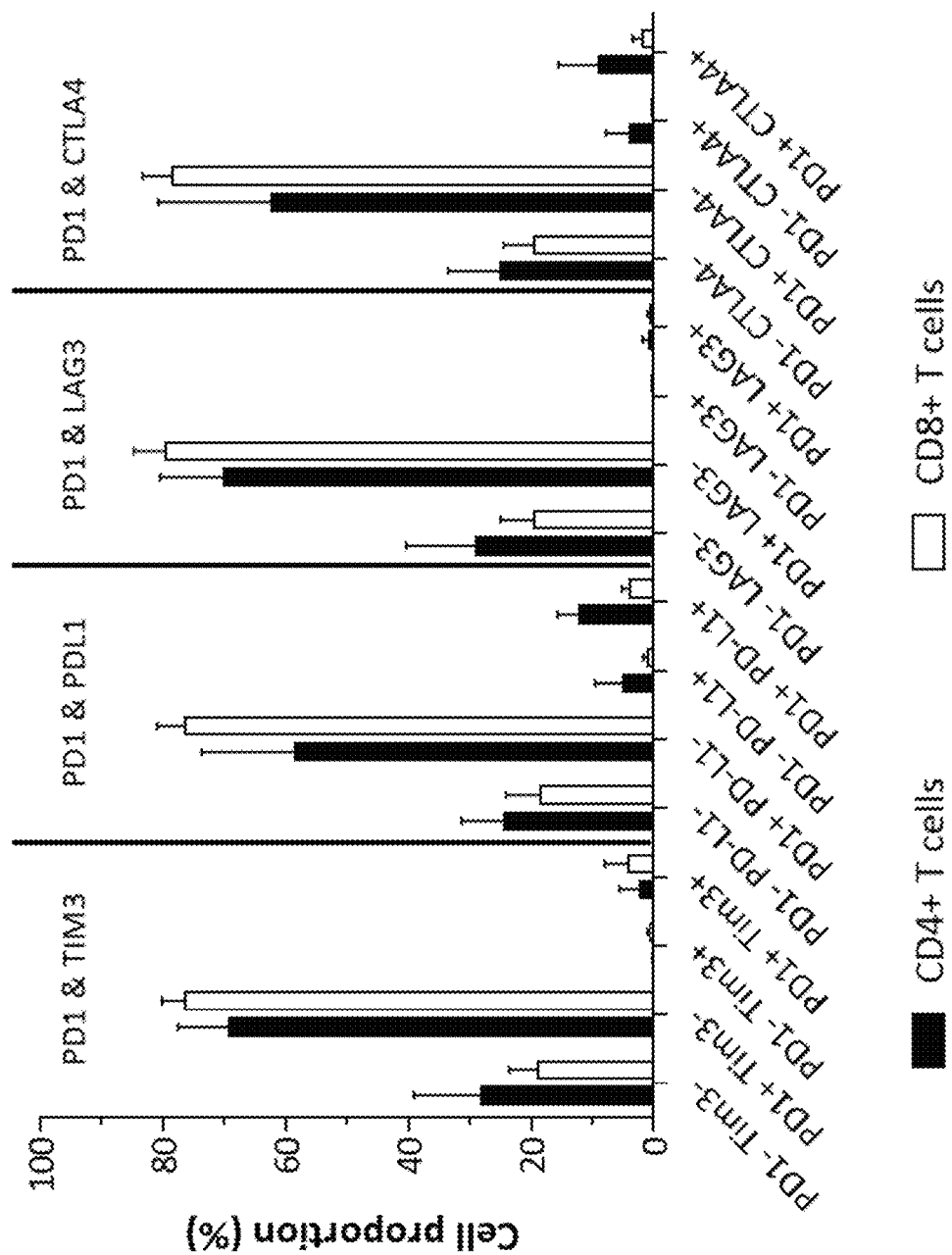
FIG. 19. Chart showing the expression of exhaustion markers PD-1, PD-L1, TIM-3, LAG-3 and CTLA4 by lung tumour infiltrating lymphocytes. Approximately ⅔ of CD4+ and CD8+ lymphocytes in the tumour express PD-1.

FIG. 19 shows the expression of PD-1, PD-L1, TIM-3, LAG-3 and CTLA-4 by tumour infiltrating lymphocytes from 3 different patients (shown are mean±SD from 3 independent experiments using cells from 3 different donors, all experiments done in triplicates). Approximately ⅔ of CD4+ and CD8+ lymphocytes in the tumour express PD-1.

The tumour dissociated mixture was co-cultured with allogeneic dendritic cells (DC) to initiate a mixed lymphocyte reaction (MLR). Cells were first cultured for 7 days without antibodies and then for 7 days in the presence of anti-PD-1 or control antibodies. After these 2 rounds, IFN-γ was assayed in supernatants by ELISA.

Figure 20A:
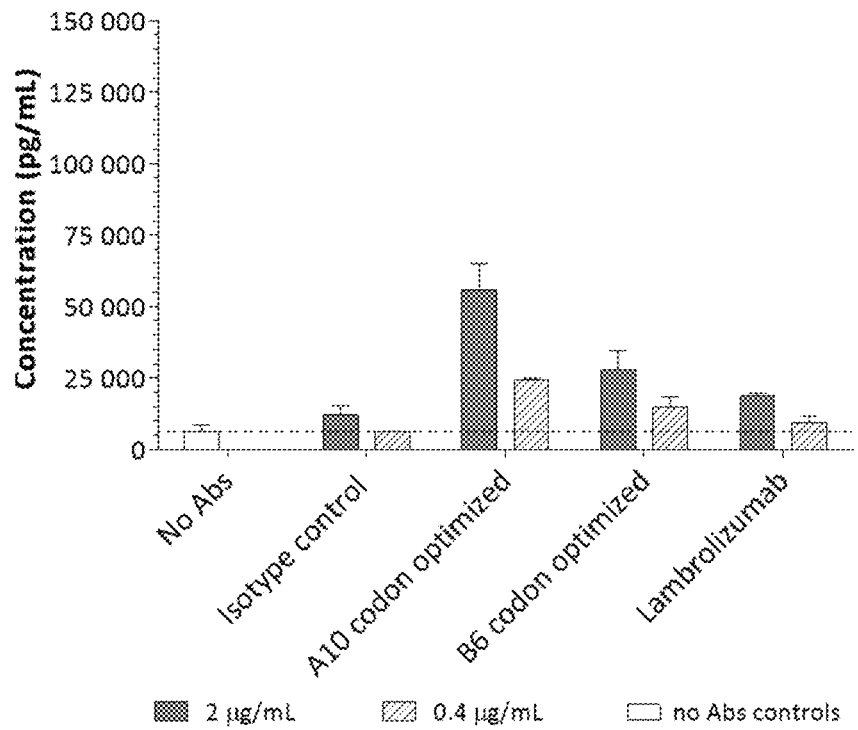
FIG. 20A. Chart showing IFN-γ secretion by tumour infiltrating lymphocytes after a mixed lymphocyte reaction in the presence or absence of anti-PD-1 antibodies for patient #1. Shown are mean±SD from duplicates or triplicates.
Figure 20B:
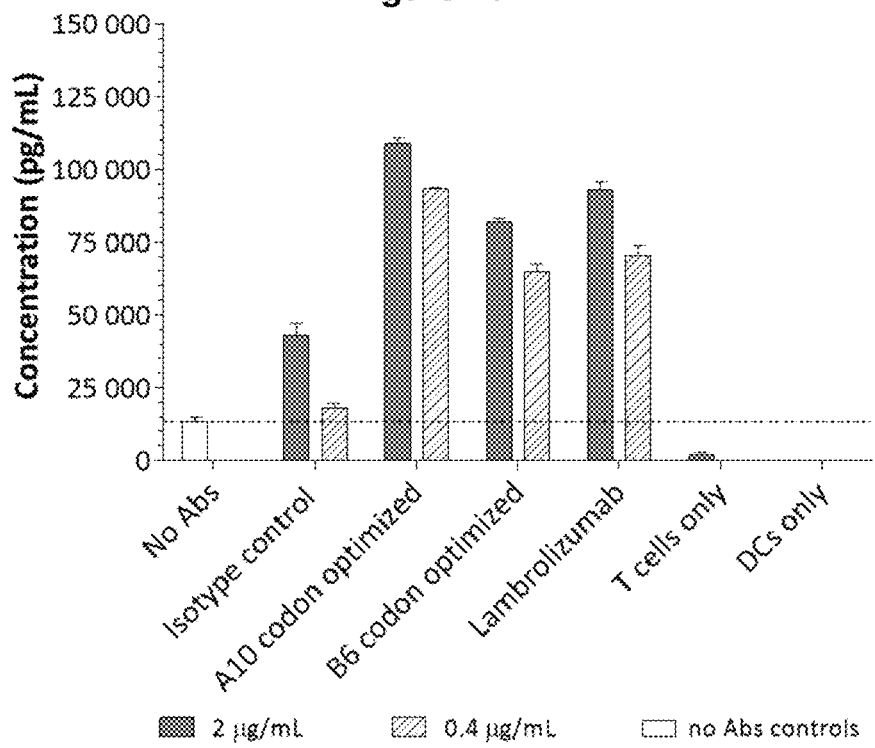
FIG. 20B. Chart showing IFN-γ secretion by tumour infiltrating lymphocytes after a mixed lymphocyte reaction in the presence or absence of anti-PD-1 antibodies for patient #2. Shown are mean±SD from duplicates or triplicates.
Figure 20C:
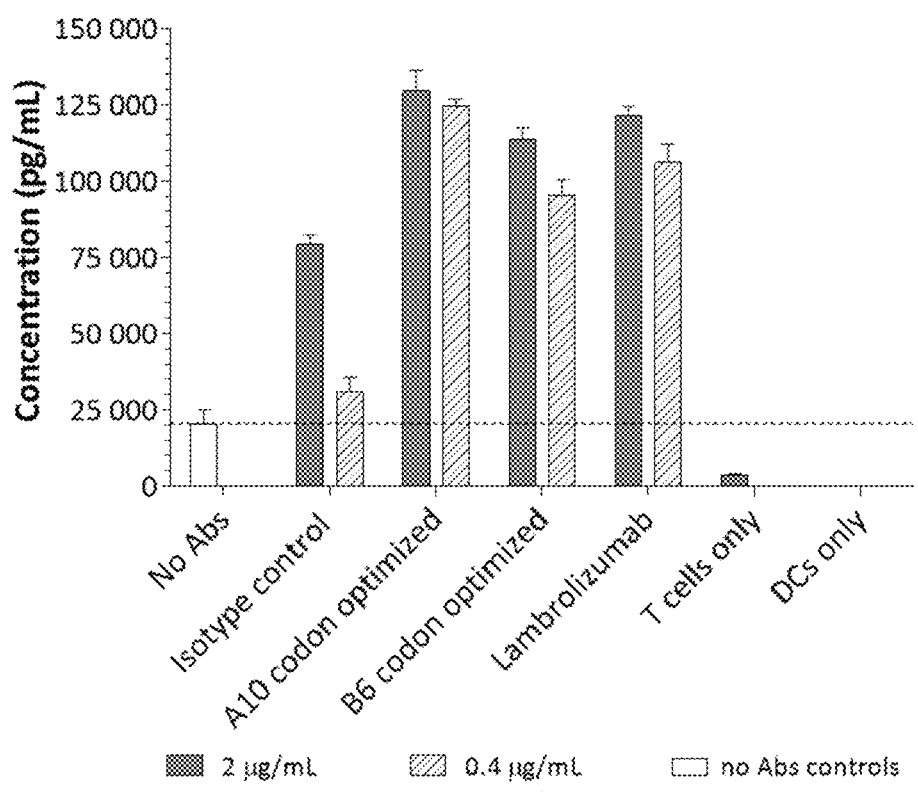
FIG. 20C. Chart showing IFN-γ secretion by tumour infiltrating lymphocytes after a mixed lymphocyte reaction in the presence or absence of anti-PD-1 antibodies for patient #3. Shown are mean±SD from duplicates or triplicates.

FIGS. 20A-20C present the secretion of IFN-γ after the MLR in the presence or absence of anti-PD-1 antibodies.

Shown are mean±SD from triplicates in 3 independent experiments (cells from 3 different patients). Anti-PD-1 antibodies were able to restore the ability of lymphocytes located in the tumour site to secrete IFN-γ in a dose-dependent manner.

Renal cell carcinoma: use of anti-PD-1 antibodies to re-activate kidney tumour infiltrating lymphocytes (ex vivo data)

Kidney tumour samples were obtained from the National Cancer Centre Singapore after approval by the proper IRB. Samples were dissociated using a human tumour dissociation kit and a tissue dissociator device.

To confirm expression of exhaustion markers at the surface of the tumour infiltrating lymphocytes, isolated cell mixture was washed once and passed through 70 μm filter to obtain single cell suspension. Cells were stained with antibodies against CD4, CD8, PD-1, PD-L1, Tim-3, LAG-3 and CTLA-4; a live/dead marker was also used to exclude dead cells from the analysis. Cells were analysed by flow cytometry. As a comparison, same markers expression was assessed on PBMCs from the same patients.

Figure 21A:
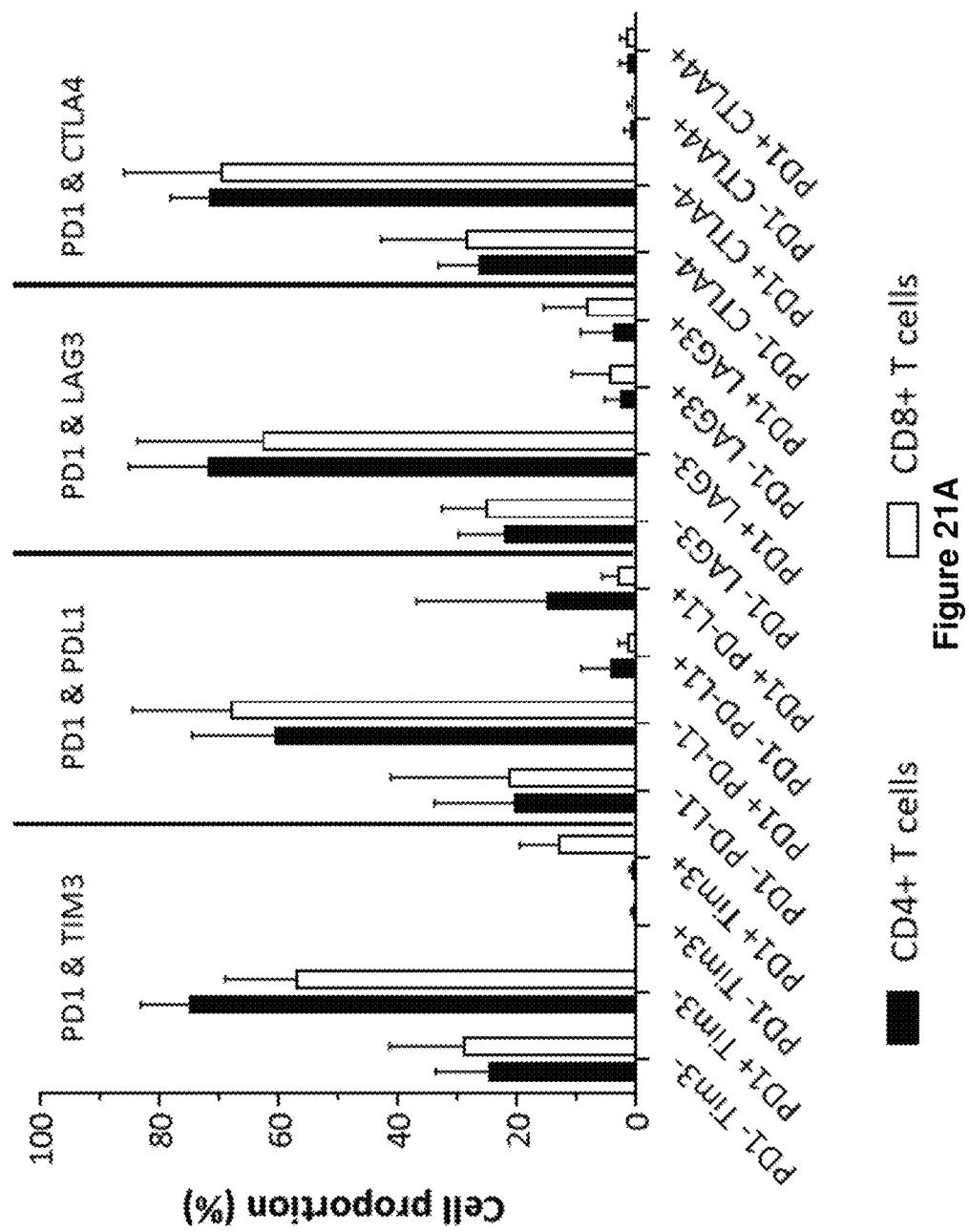
FIG. 21A. Chart showing the expression of exhaustion markers PD-1, PD-L1, TIM-3, LAG-3 and CTLA4 by renal tumour infiltrating lymphocytes. Approximately ⅔ of CD4+ and CD8+ lymphocytes in the tumour express PD-1, while most of PBMC lymphocytes do not express PD-1.
Figure 21B:
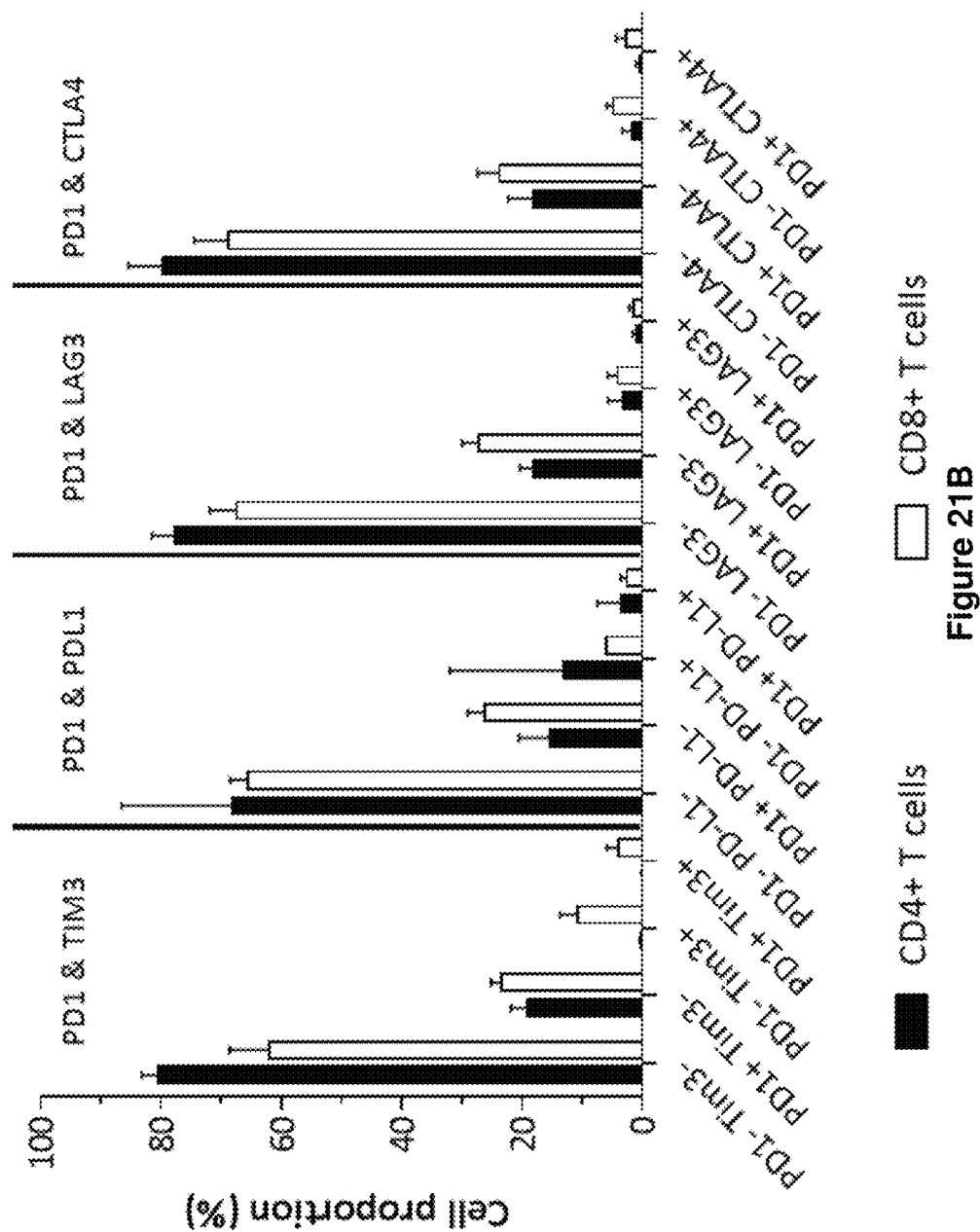
FIG. 21B. Chart showing the expression of exhaustion markers PD-1, PD-L1, TIM-3, LAG-3 and CTLA4 by blood circulating lymphocytes from renal carcinoma patients. Approximately ⅔ of CD4+ and CD8+ lymphocytes in the tumour express PD-1, while most of PBMC lymphocytes do not express PD-1.

FIGS. 21A and 21B show the expression of PD-1, PD-L1, TIM-3, LAG-3 and CTLA-4 by tumour infiltrating lymphocytes (FIG. 21A) and on blood circulating lymphocytes (FIG. 21B) from 3 different patients (shown are mean±SD from 3 independent experiments using cells from 3 different donors, all experiments done in triplicates). Approximately ⅔ of CD4+ and CD8+ lymphocytes in the tumour express PD-1 while most of PBMC lymphocytes do not express PD-1.

The tumour dissociated mixture was co-cultured with allogeneic dendritic cells (DC) to initiate a mixed lymphocyte reaction (MLR). Cells were first cultured for 7 days without antibodies and then for 7 days in the presence of anti-PD-1 or control antibodies. After these 2 rounds, IFN-γ was assayed in supernatants by ELISA.

Figure 22A:
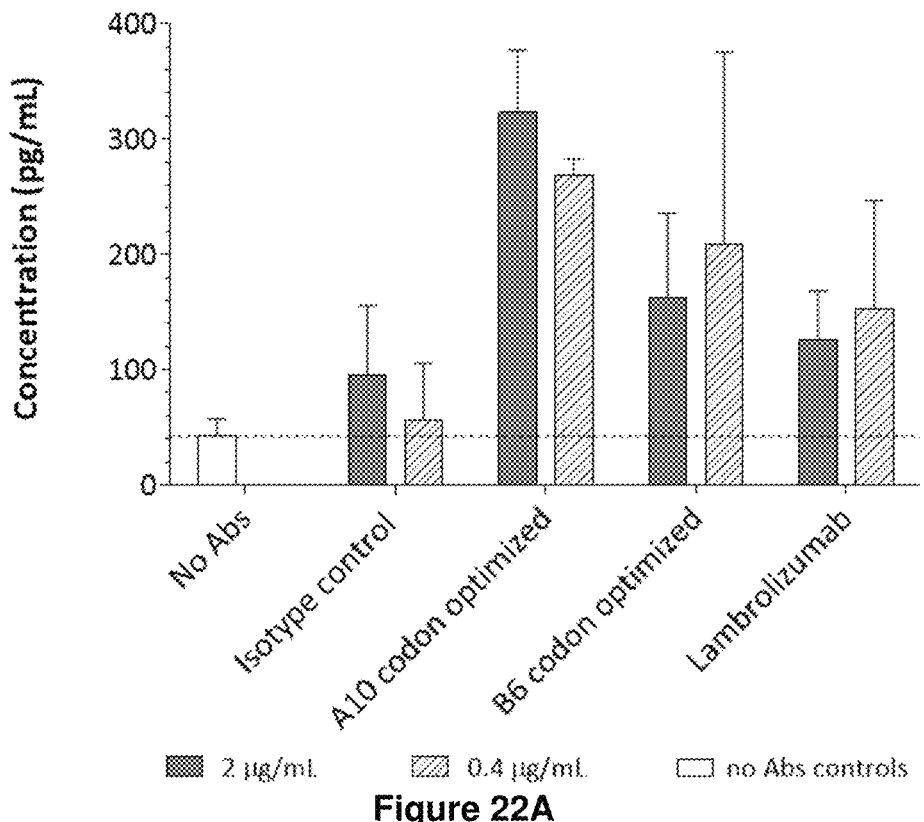
FIG. 22A. Chart showing IFN-γ secretion by tumour infiltrating lymphocytes after a mixed lymphocyte reaction in the presence or absence of anti-PD-1 antibodies for patient #1. Shown are mean±SD from duplicates or triplicates.
Figure 22B:
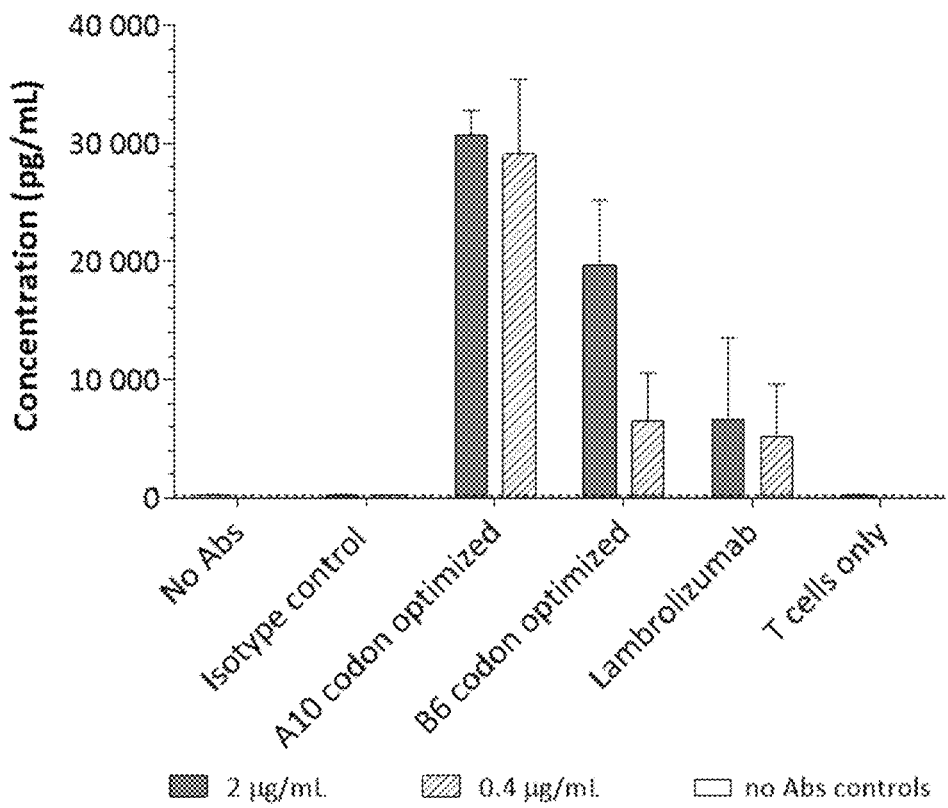
FIG. 22B. Chart showing IFN-γ secretion by tumour infiltrating lymphocytes after a mixed lymphocyte reaction in the presence or absence of anti-PD-1 antibodies for patient #2. Shown are mean±SD from duplicates or triplicates.
Figure 22C:
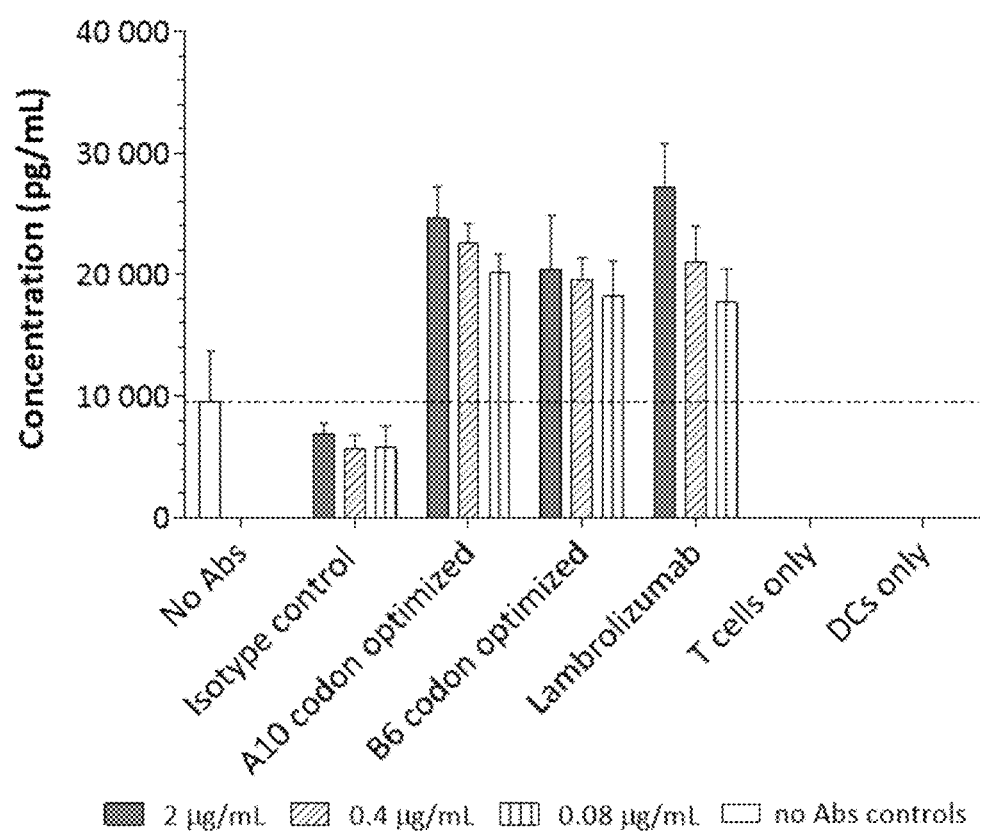
FIG. 22C. Chart showing IFN-γ secretion by tumour infiltrating lymphocytes after a mixed lymphocyte reaction in the presence or absence of anti-PD-1 antibodies for patient #3. Shown are mean±SD from duplicates or triplicates.

FIGS. 22A-22C present the secretion of IFN-γ after the MLR in the presence or absence of anti-PD-1 antibodies. Shown are mean±SD from duplicates or triplicates in 3 independent experiments (cells from 3 different patients). Anti-PD-1 antibodies were able to restore the ability of lymphocytes located in the tumour site to secrete IFN-γ in a dose-dependent manner.

Bladder Cancer: Use of Anti-PD-1 Antibodies to Re-Activate Bladder Tumour Infiltrating Lymphocytes (Ex Vivo Data)

Bladder tumour samples were obtained from the National Cancer Centre Singapore after approval by the proper IRB. Samples were dissociated using a human tumour dissociation kit and a tissue dissociator device.

To confirm expression of exhaustion markers at the surface of the tumour infiltrating lymphocytes, isolated cell mixture was washed once and passed through 70 μm filter to obtain single cell suspension. Cells were stained with antibodies against CD4, CD8, PD-1, PD-L1, Tim-3, LAG-3 and CTLA-4; a live/dead marker was also used to exclude dead cells from the analysis. Cells were analysed by flow cytometry.

Figure 23B:
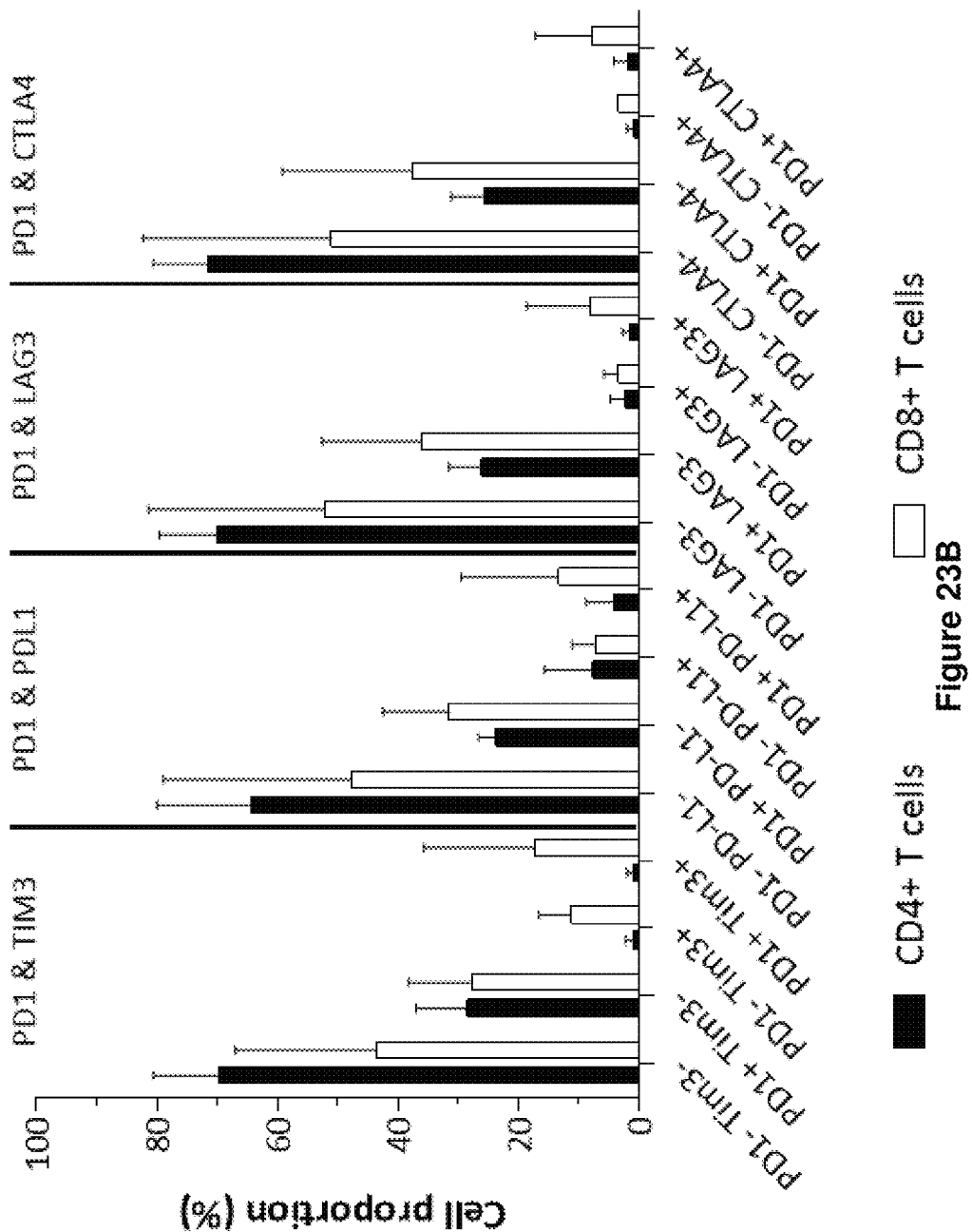
FIG. 23B. Chart showing the expression of exhaustion markers PD-1, PD-L1, TIM-3, LAG-3 and CTLA4 by blood circulating lymphocytes from bladder carcinoma patients. A majority of tumour infiltrating lymphocytes express PD-1, while only a minority of PBMC lymphocytes express PD-1.

FIGS. 23A and 23B show the expression of PD-1, PD-L1, TIM-3, LAG-3 and CTLA-4 by tumour infiltrating lymphocytes (FIG. 23A) and blood circulating lymphocytes (FIG. 23B) from 2 different patients (shown are mean±SD from 2 independent experiments using cells from 2 different donors, all experiments done in triplicates). A majority of tumour infiltrating lymphocytes express PD-1, while only a minority of their blood circulating counterparts do so.

The tumour dissociated mixture was co-cultured with allogeneic dendritic cells (DC) to initiate a mixed lymphocyte reaction (MLR). Cells were first cultured for 7 days without antibodies and then for 7 days in the presence of anti-PD-1 or control antibodies. After these 2 rounds, IFN-γ was assayed in supernatants by ELISA.

Figure 24:
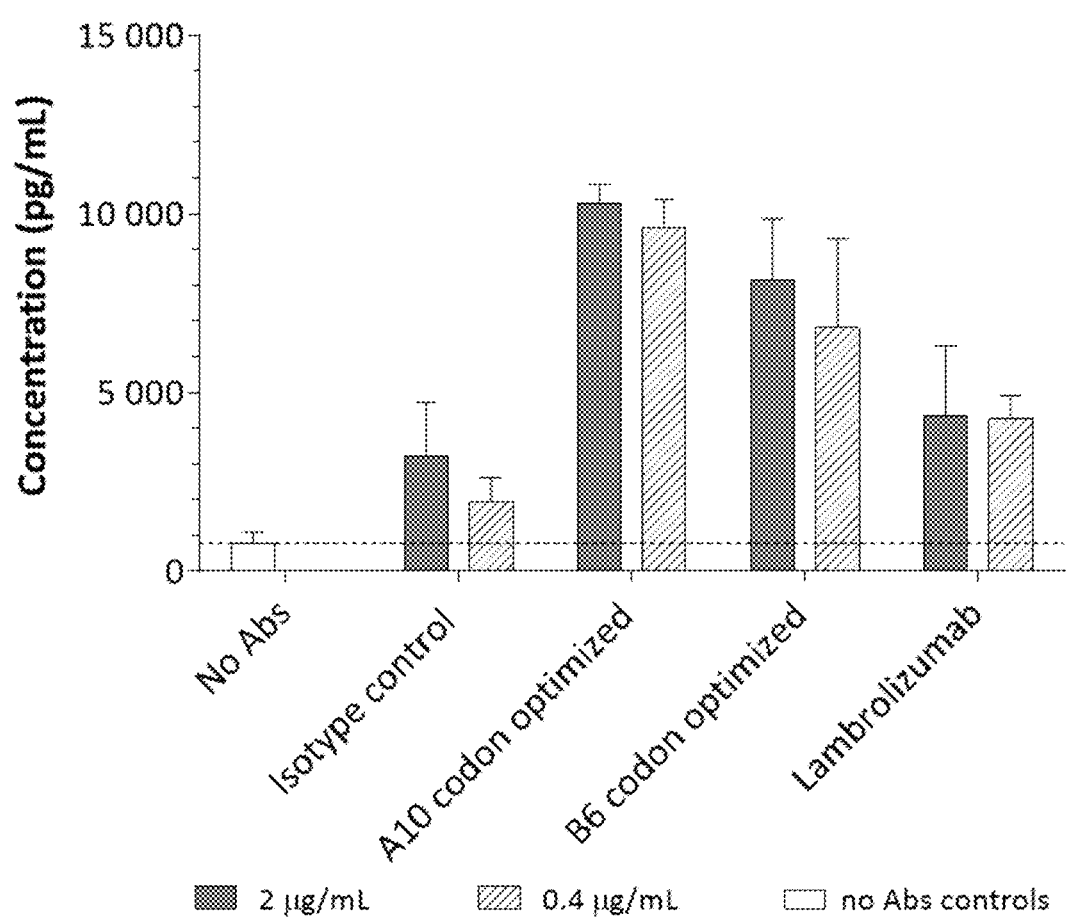
FIG. 24. Chart showing IFN-γ secretion by tumour infiltrating lymphocytes after a mixed lymphocyte reaction in the presence or absence of anti-PD-1 antibodies, for one patient. Shown are mean±SD from duplicates or triplicates.

FIG. 24 presents the secretion of IFN-γ after the MLR in the presence or absence of anti-PD-1 antibodies. Shown are mean±SD from triplicates in 1 experiment. Anti-PD-1 antibodies were able to restore the ability of lymphocytes located in the tumour site to secrete IFN-γ in a dose-dependent manner.

The invention claimed is:

1. An antibody or antigen binding fragment, optionally isolated, which is capable of binding to PD-1, comprising:
at least one light chain variable region incorporating the following CDRs:

LC-CDR1: SGSSSNIKFNSVN (SEQ ID NO: 25)

LC-CDR2: SNNQRPS (SEQ ID NO: 26)

LC-CDR3: ASWDDVLYGSV, (SEQ ID NO: 27)

SAWDDYLHGTV, (SEQ ID NO: 30)

ASWDDYVRGTM, (SEQ ID NO: 31)

SSWDDFLRGTV, (SEQ ID NO: 32)

SSWDDDARGTI, (SEQ ID NO: 33)

AAWDDVYYGTI, (SEQ ID NO: 34)

ASWDDSLYGTV, (SEQ ID NO: 35)

AAWDDAYYGTI, (SEQ ID NO: 36)

ASWDDVYRGTV (SEQ ID NO: 37)
or

SSWDDSLYGTI; (SEQ ID NO: 38)

and at least one heavy chain variable region incorporating the following CDRs:

HC-CDR1: SYGMH (SEQ ID NO: 89)
or

GFTFSSYGMH (SEQ ID NO: 39)

-continued

```
                                        (SEQ ID NO: 40)
HC-CDR2: VISYDGSNKYYADSVKG (SEQ ID NO: 41)
HC-CDR3: DLGAGPYYYGKDH, (SEQ ID NO: 44)
DLGAGPYYYGLDV, (SEQ ID NO: 45)
DLGAGPYYYGMDV, (SEQ ID NO: 46)
DLGAGPYYYGMDV, (SEQ ID NO: 47)
DLGAGPYYYGMDV, (SEQ ID NO: 48)
DLGAGPYYYGMDV, (SEQ ID NO: 49)
DLGAGPYYYGMDV, (SEQ ID NO: 50)
DYGAGPYYYGMDV, (SEQ ID NO: 51)
DLGSGYYLYGMDV,
or (SEQ ID NO: 52)
DLGAGPYYYGMDV.
```

2. The antibody or antigen binding fragment of claim 1, having:
(i) at least one light chain variable region incorporating the following CDRs:

```
                                        (SEQ ID NO: 25)
LC-CDR1: SGSSSNIKFNSVN (SEQ ID NO: 26)
LC-CDR2: SNNQRPS (SEQ ID NO: 27)
LC-CDR3: ASWDDVLYGSV;
``` and
at least one heavy chain variable region incorporating the following CDRs:

```
                                        (SEQ ID NO: 89)
HC-CDR1: SYGMH
or
                                        (SEQ ID NO: 39)
GFTFSSYGMH (SEQ ID NO: 40)
HC-CDR2: VISYDGSNKYYADSVKG (SEQ ID NO: 41)
HC-CDR3: DLGAGPYYYGKDH;
``` or
(ii) at least one light chain variable region incorporating the following CDRs:

```
                                        (SEQ ID NO: 25)
LC-CDR1: SGSSSNIKFNSVN (SEQ ID NO: 26)
LC-CDR2: SNNQRPS (SEQ ID NO: 30)
LC-CDR3: SAWDDYLHGTV;
``` and
at least one heavy chain variable region incorporating the following CDRs:

```
                                        (SEQ ID NO: 89)
HC-CDR1: SYGMH
or
                                        (SEQ ID NO: 39)
GFTFSSYGMH (SEQ ID NO: 40)
HC-CDR2: VISYDGSNKYYADSVKG (SEQ ID NO: 44)
HC-CDR3: DLGAGPYYYGLDV;
``` or
(iii) at least one light chain variable region incorporating the following CDRs:

```
                                        (SEQ ID NO: 25)
LC-CDR1: SGSSSNIKFNSVN (SEQ ID NO: 26)
LC-CDR2: SNNQRPS (SEQ ID NO: 31)
LC-CDR3: ASWDDYVRGTM;
``` and
at least one heavy chain variable region incorporating the following CDRs:

```
                                        (SEQ ID NO: 89)
HC-CDR1: SYGMH
or
                                        (SEQ ID NO: 39)
GFTFSSYGMH (SEQ ID NO: 40)
HC-CDR2: VISYDGSNKYYADSVKG (SEQ ID NO: 45)
HC-CDR3: DLGAGPYYYGMDV;
``` or
(iv) at least one light chain variable region incorporating the following CDRs:

```
                                        (SEQ ID NO: 25)
LC-CDR1: SGSSSNIKFNSVN (SEQ ID NO: 26)
LC-CDR2: SNNQRPS (SEQ ID NO: 32)
LC-CDR3: SSWDDFLRGTV;
``` and
at least one heavy chain variable region incorporating the following CDRs:

HC-CDR1: SYGMH (SEQ ID NO: 89)
or
GFTFSSYGMH (SEQ ID NO: 39)
HC-CDR2: VISYDGSNKYYADSVKG (SEQ ID NO: 40)
HC-CDR3: DLGAGPYYYGMDV; (SEQ ID NO: 46)

or
(v) at least one light chain variable region incorporating the following CDRs:

LC-CDR1: SGSSSNIKFNSVN (SEQ ID NO: 25)
LC-CDR2: SNNQRPS (SEQ ID NO: 26)
LC-CDR3: SSWDDDARGTI; (SEQ ID NO: 33)

and
at least one heavy chain variable region incorporating the following CDRs:

HC-CDR1: SYGMH (SEQ ID NO: 89)
or
GFTFSSYGMH (SEQ ID NO: 39)
HC-CDR2: VISYDGSNKYYADSVKG (SEQ ID NO: 40)
HC-CDR3: DLGAGPYYYGMDV; (SEQ ID NO: 47)

or
(vi) at least one light chain variable region incorporating the following CDRs:

LC-CDR1: SGSSSNIKFNSVN (SEQ ID NO: 25)
LC-CDR2: SNNQRPS (SEQ ID NO: 26)
LC-CDR3: AAWDDVYYGTI; (SEQ ID NO: 34)

and
at least one heavy chain variable region incorporating the following CDRs:

HC-CDR1: SYGMH (SEQ ID NO: 89)
or
GFTFSSYGMH (SEQ ID NO: 39)
HC-CDR2: VISYDGSNKYYADSVKG (SEQ ID NO: 40)
HC-CDR3: DLGAGPYYYGMDV; (SEQ ID NO: 48)

or
(vii) at least one light chain variable region incorporating the following CDRs:

LC-CDR1: SGSSSNIKFNSVN (SEQ ID NO: 25)
LC-CDR2: SNNQRPS (SEQ ID NO: 26)
LC-CDR3: ASWDDSLYGTV; (SEQ ID NO: 35)

and
at least one heavy chain variable region incorporating the following CDRs:

HC-CDR1: SYGMH (SEQ ID NO: 89)
or
GFTFSSYGMH (SEQ ID NO: 39)
HC-CDR2: VISYDGSNKYYADSVKG (SEQ ID NO: 40)
HC-CDR3: DLGAGPYYYGMDV; (SEQ ID NO: 49)

or
(viii) at least one light chain variable region incorporating the following CDRs:

LC-CDR1: SGSSSNIKFNSVN (SEQ ID NO: 25)
LC-CDR2: SNNQRPS (SEQ ID NO: 26)
LC-CDR3: AAWDDAYYGTI; (SEQ ID NO: 36)

and
at least one heavy chain variable region incorporating the following CDRs:

HC-CDR1: SYGMH (SEQ ID NO: 89)
or
GFTFSSYGMH (SEQ ID NO: 39)
HC-CDR2: VISYDGSNKYYADSVKG (SEQ ID NO: 40)
HC-CDR3: DYGAGPYYYGMDV; (SEQ ID NO: 50)

or
(ix) at least one light chain variable region incorporating the following CDRs:

LC-CDR1: SGSSSNIKFNSVN (SEQ ID NO: 25)
LC-CDR2: SNNQRPS (SEQ ID NO: 26)
LC-CDR3: ASWDDVYRGTV; (SEQ ID NO: 37)

and
at least one heavy chain variable region incorporating the following CDRs:

```
                              (SEQ ID NO: 89)
HC-CDR1: SYGMH
or
                              (SEQ ID NO: 39)
GFTFSSYGMH
                              (SEQ ID NO: 40)
HC-CDR2: VISYDGSNKYYADSVKG
                              (SEQ ID NO: 51)
HC-CDR3: DLGSGYYLYGMDV;
``` or (x) at least one light chain variable region incorporating the following CDRs:

```
                              (SEQ ID NO: 25)
LC-CDR1: SGSSSNIKFNSVN
                              (SEQ ID NO: 26)
LC-CDR2: SNNQRPS
                              (SEQ ID NO: 38)
LC-CDR3: SSWDDSLYGTI;
``` and
at least one heavy chain variable region incorporating the following CDRs:

```
                              (SEQ ID NO: 89)
HC-CDR1: SYGMH
or
                              (SEQ ID NO: 39)
GFTFSSYGMH
                              (SEQ ID NO: 40)
HC-CDR2: VISYDGSNKYYADSVKG
                              (SEQ ID NO: 52)
HC-CDR3: DLGAGPYYYGMDV.
```

3. The antibody or antigen binding fragment according to claim 1, wherein:
the heavy chain variable region sequence has at least 70% sequence identity to the heavy chain variable region sequence of SEQ ID NO:13, 16, 17, 18, 19, 20, 21, 22, 23 or 24, and
the light chain variable region sequence has at least 70% sequence identity to the light chain variable region sequence of SEQ ID NO:1, 4, 5, 6, 7, 8, 9, 10, 11 or 12.

4. The antibody or antigen binding fragment according to claim 1, wherein:
(i) the heavy chain variable region sequence has at least 70% sequence identity to the heavy chain variable region sequence of SEQ ID NO:13, and
the light chain variable region sequence has at least 70% sequence identity to the light chain variable region sequence of SEQ ID NO:1;
or
(ii) the heavy chain variable region sequence has at least 70% sequence identity to the heavy chain variable region sequence of SEQ ID NO:16, and
the light chain variable region sequence has at least 70% sequence identity to the light chain variable region sequence of SEQ ID NO:4;
or
(iii) the heavy chain variable region sequence has at least 70% sequence identity to the heavy chain variable region sequence of SEQ ID NO:17, and
the light chain variable region sequence has at least 70% sequence identity to the light chain variable region sequence of SEQ ID NO:5;
or
(iv) the heavy chain variable region sequence has at least 70% sequence identity to the heavy chain variable region sequence of SEQ ID NO:18, and
the light chain variable region sequence has at least 70% sequence identity to the light chain variable region sequence of SEQ ID NO:6;
(v) the heavy chain variable region sequence has at least 70% sequence identity to the heavy chain variable region sequence of SEQ ID NO:19, and
the light chain variable region sequence has at least 70% sequence identity to the light chain variable region sequence of SEQ ID NO:7;
or
(vi) the heavy chain variable region sequence has at least 70% sequence identity to the heavy chain variable region sequence of SEQ ID NO:20, and
the light chain variable region sequence has at least 70% sequence identity to the light chain variable region sequence of SEQ ID NO:8;
(vii) the heavy chain variable region sequence has at least 70% sequence identity to the heavy chain variable region sequence of SEQ ID NO:21, and
the light chain variable region sequence has at least 70% sequence identity to the light chain variable region sequence of SEQ ID NO:9;
or
(viii) the heavy chain variable region sequence has at least 70% sequence identity to the heavy chain variable region sequence of SEQ ID NO:22, and
the light chain variable region sequence has at least 70% sequence identity to the light chain variable region sequence of SEQ ID NO:10;
(ix) the heavy chain variable region sequence has at least 70% sequence identity to the heavy chain variable region sequence of SEQ ID NO:23, and
the light chain variable region sequence has at least 70% sequence identity to the light chain variable region sequence of SEQ ID NO:11;
or
(x) the heavy chain variable region sequence has at least 70% sequence identity to the heavy chain variable region sequence of SEQ ID NO:24, and
the light chain variable region sequence has at least 70% sequence identity to the light chain variable region sequence of SEQ ID NO:12.

5. The antibody or antigen binding fragment of claim 1, wherein the antibody or antigen binding fragment specifically binds human or rhesus PD-1 over other members of the CD28 family.

6. The antibody or antigen binding fragment of claim 1, wherein the antibody or antigen binding fragment is effective to restore T-cell function in T-cells exhibiting T-cell exhaustion or T-cell anergy.

7. The antigen binding fragment of claim 1, wherein the antigen binding fragment is a Fab fragment or scFv fragment.

8. The antibody of claim 1, wherein the antibody comprises a human constant region selected from IgG1, IgG2, IgG3 and IgG4.

9. The antibody or antigen binding fragment of claim 1, which is a bispecific antibody or a bispecific antigen binding fragment comprising (i) an antigen binding fragment according to claim 1, and (ii) an antigen binding domain which is capable of binding to a target protein other than PD-1.

10. The antibody or antigen binding fragment of claim 9, wherein the antigen binding domain which is capable of binding to a target protein other than PD-1 is capable of binding to one of TIM-3, LAGS, ICOS, CTLA4, BTLA or CD28.

11. A method for expanding a population of T cells, wherein T cells are contacted in vitro or ex vivo with an antibody or antigen binding fragment which is capable of binding to PD-1, and which comprises:

at least one light chain variable region incorporating the following CDRs:

```
                              (SEQ ID NO: 25)
    LC-CDR1: SGSSSNIKFNSVN (SEQ ID NO: 26)
    LC-CDR2: SNNQRPS (SEQ ID NO: 27)
    LC-CDR3: ASWDDVLYGSV, (SEQ ID NO: 30)
    SAWDDYLHGTV, (SEQ ID NO: 31)
    ASWDDYVRGTM, (SEQ ID NO: 32)
    SSWDDFLRGTV, (SEQ ID NO: 33)
    SSWDDDARGTI, (SEQ ID NO: 34)
    AAWDDVYYGTI, (SEQ ID NO: 35)
    ASWDDSLYGTV, (SEQ ID NO: 36)
    AAWDDAYYGTI, (SEQ ID NO: 37)
    ASWDDVYRGTV
    or (SEQ ID NO: 38)
    SSWDDSLYGTI;
``` and at least one heavy chain variable region incorporating the following CDRs:

```
                              (SEQ ID NO: 89)
    HC-CDR1: SYGMH
    or (SEQ ID NO: 39)
    GFTFSSYGMH (SEQ ID NO: 40)
    HC-CDR2: VISYDGSNKYYADSVKG (SEQ ID NO: 41)
    HC-CDR3: DLGAGPYYYGKDH, (SEQ ID NO: 44)
    DLGAGPYYYGLDV,
```

-continued
```
                              (SEQ ID NO: 45)
    DLGAGPYYYGMDV, (SEQ ID NO: 46)
    DLGAGPYYYGMDV, (SEQ ID NO: 47)
    DLGAGPYYYGMDV, (SEQ ID NO: 48)
    DLGAGPYYYGMDV, (SEQ ID NO: 49)
    DLGAGPYYYGMDV, (SEQ ID NO: 50)
    DYGAGPYYYGMDV, (SEQ ID NO: 51)
    DLGSGYYLYGMDV,
    or (SEQ ID NO: 52)
    DLGAGPYYYGMDV.
```

12. The method according to claim 11, wherein the antibody or antigen binding fragment comprises:

(i) at least one light chain variable region incorporating the following CDRs:

```
                              (SEQ ID NO: 25)
    LC-CDR1: SGSSSNIKFNSVN (SEQ ID NO: 26)
    LC-CDR2: SNNQRPS (SEQ ID NO: 27)
    LC-CDR3: ASWDDVLYGSV;
``` and at least one heavy chain variable region incorporating the following CDRs:

```
                              (SEQ ID NO: 89)
    HC-CDR1: SYGMH
    or (SEQ ID NO: 39)
    GFTFSSYGMH (SEQ ID NO: 40)
    HC-CDR2: VISYDGSNKYYADSVKG (SEQ ID NO: 41)
    HC-CDR3: DLGAGPYYYGKDH;
``` or (ii) at least one light chain variable region incorporating the following CDRs:

```
                              (SEQ ID NO: 25)
    LC-CDR1: SGSSSNIKFNSVN (SEQ ID NO: 26)
    LC-CDR2: SNNQRPS (SEQ ID NO: 30)
    LC-CDR3: SAWDDYLHGTV;
``` and at least one heavy chain variable region incorporating the following CDRs:

HC-CDR1: SYGMH (SEQ ID NO: 89)
or
GFTFSSYGMH (SEQ ID NO: 39)
HC-CDR2: VISYDGSNKYYADSVKG (SEQ ID NO: 40)
HC-CDR3: DLGAGPYYYGLDV; (SEQ ID NO: 44)

or (iii) at least one light chain variable region incorporating the following CDRs:

LC-CDR1: SGSSSNIKFNSVN (SEQ ID NO: 25)
LC-CDR2: SNNQRPS (SEQ ID NO: 26)
LC-CDR3: ASWDDYVRGTM; (SEQ ID NO: 31)

and
at least one heavy chain variable region incorporating the following CDRs:

HC-CDR1: SYGMH (SEQ ID NO: 89)
or
GFTFSSYGMH (SEQ ID NO: 39)
HC-CDR2: VISYDGSNKYYADSVKG (SEQ ID NO: 40)
HC-CDR3: DLGAGPYYYGMDV; (SEQ ID NO: 45)

or (iv) at least one light chain variable region incorporating the following CDRs:

LC-CDR1: SGSSSNIKFNSVN (SEQ ID NO: 25)
LC-CDR2: SNNQRPS (SEQ ID NO: 26)
LC-CDR3: SSWDDFLRGTV; (SEQ ID NO: 32)

and
at least one heavy chain variable region incorporating the following CDRs:

HC-CDR1: SYGMH (SEQ ID NO: 89)
or
GFTFSSYGMH (SEQ ID NO: 39)
HC-CDR2: VISYDGSNKYYADSVKG (SEQ ID NO: 40)
HC-CDR3: DLGAGPYYYGMDV; (SEQ ID NO: 46)

or (v) at least one light chain variable region incorporating the following CDRs:

LC-CDR1: SGSSSNIKFNSVN (SEQ ID NO: 25)
LC-CDR2: SNNQRPS (SEQ ID NO: 26)
LC-CDR3: SSWDDDARGTI; (SEQ ID NO: 33)

and
at least one heavy chain variable region incorporating the following CDRs:

HC-CDR1: SYGMH (SEQ ID NO: 89)
or
GFTFSSYGMH (SEQ ID NO: 39)
HC-CDR2: VISYDGSNKYYADSVKG (SEQ ID NO: 40)
HC-CDR3: DLGAGPYYYGMDV; (SEQ ID NO: 47)

or (vi) at least one light chain variable region incorporating the following CDRs:

LC-CDR1: SGSSSNIKFNSVN (SEQ ID NO: 25)
LC-CDR2: SNNQRPS (SEQ ID NO: 26)
LC-CDR3: AAWDDVYYGTI; (SEQ ID NO: 34)

and
at least one heavy chain variable region incorporating the following CDRs:

HC-CDR1: SYGMH (SEQ ID NO: 89)
or
GFTFSSYGMH (SEQ ID NO: 39)
HC-CDR2: VISYDGSNKYYADSVKG (SEQ ID NO: 40)
HC-CDR3: DLGAGPYYYGMDV; (SEQ ID NO: 48)

or (vii) at least one light chain variable region incorporating the following CDRs:

LC-CDR1: SGSSSNIKFNSVN (SEQ ID NO: 25)
LC-CDR2: SNNQRPS (SEQ ID NO: 26)
LC-CDR3: ASWDDSLYGTV; (SEQ ID NO: 35)

and
at least one heavy chain variable region incorporating the following CDRs:

```
                                        (SEQ ID NO: 89)
    HC-CDR1: SYGMH
    or
                                        (SEQ ID NO: 39)
    GFTFSSYGMH (SEQ ID NO: 40)
    HC-CDR2: VISYDGSNKYYADSVKG (SEQ ID NO: 49)
    HC-CDR3: DLGAGPYYYGMDV;
``` or (viii) at least one light chain variable region incorporating the following CDRs:

```
                                        (SEQ ID NO: 25)
    LC-CDR1: SGSSSNIKFNSVN (SEQ ID NO: 26)
    LC-CDR2: SNNQRPS (SEQ ID NO: 36)
    LC-CDR3: AAWDDAYYGTI;
``` and
at least one heavy chain variable region incorporating the following CDRs:

```
                                        (SEQ ID NO: 89)
    HC-CDR1: SYGMH
    or
                                        (SEQ ID NO: 39)
    GFTFSSYGMH (SEQ ID NO: 40)
    HC-CDR2: VISYDGSNKYYADSVKG (SEQ ID NO: 50)
    HC-CDR3: DYGAGPYYYGMDV;
``` or (ix) at least one light chain variable region incorporating the following CDRs:

```
                                        (SEQ ID NO: 25)
    LC-CDR1: SGSSSNIKFNSVN (SEQ ID NO: 26)
    LC-CDR2: SNNQRPS (SEQ ID NO: 37)
    LC-CDR3: ASWDDVYRGTV;
``` and
at least one heavy chain variable region incorporating the following CDRs:

```
                                        (SEQ ID NO: 89)
    HC-CDR1: SYGMH
    or
                                        (SEQ ID NO: 39)
    GFTFSSYGMH
```

-continued
```
                                        (SEQ ID NO: 40)
    HC-CDR2: VISYDGSNKYYADSVKG (SEQ ID NO: 51)
    HC-CDR3: DLGSGYYLYGMDV;
``` or (x) at least one light chain variable region incorporating the following CDRs:

```
                                        (SEQ ID NO: 25)
    LC-CDR1: SGSSSNIKFNSVN (SEQ ID NO: 26)
    LC-CDR2: SNNQRPS (SEQ ID NO: 38)
    LC-CDR3: SSWDDSLYGTI;
``` and
at least one heavy chain variable region incorporating the following CDRs:

```
                                        (SEQ ID NO: 89)
    HC-CDR1: SYGMH
    or
                                        (SEQ ID NO: 39)
    GFTFSSYGMH (SEQ ID NO: 40)
    HC-CDR2: VISYDGSNKYYADSVKG (SEQ ID NO: 52)
    HC-CDR3: DLGAGPYYYGMDV.
```

13. The method according to claim 11, wherein:
the heavy chain variable region sequence has at least 70% sequence identity to the heavy chain variable region sequence of SEQ ID NO:13, 16, 17, 18, 19, 20, 21, 22, 23 or 24, and
the light chain variable region sequence has at least 70% sequence identity to the light chain variable region sequence of SEQ ID NO:1, 4, 5, 6, 7, 8, 9, 10, 11 or 12.

14. The method according to claim 11, wherein the:
(i) the heavy chain variable region sequence has at least 70% sequence identity to the heavy chain variable region sequence of SEQ ID NO:13, and
the light chain variable region sequence has at least 70% sequence identity to the light chain variable region sequence of SEQ ID NO:1;
or
(ii) the heavy chain variable region sequence has at least 70% sequence identity to the heavy chain variable region sequence of SEQ ID NO:16, and
the light chain variable region sequence has at least 70% sequence identity to the light chain variable region sequence of SEQ ID NO:4;
(iii) the heavy chain variable region sequence has at least 70% sequence identity to the heavy chain variable region sequence of SEQ ID NO:17, and
the light chain variable region sequence has at least 70% sequence identity to the light chain variable region sequence of SEQ ID NO:5;
or
(iv) the heavy chain variable region sequence has at least 70% sequence identity to the heavy chain variable region sequence of SEQ ID NO:18, and
the light chain variable region sequence has at least 70% sequence identity to the light chain variable region sequence of SEQ ID NO:6;

(v) the heavy chain variable region sequence has at least 70% sequence identity to the heavy chain variable region sequence of SEQ ID NO:19, and
the light chain variable region sequence has at least 70% sequence identity to the light chain variable region sequence of SEQ ID NO:7;
or
(vi) the heavy chain variable region sequence has at least 70% sequence identity to the heavy chain variable region sequence of SEQ ID NO:20, and
the light chain variable region sequence has at least 70% sequence identity to the light chain variable region sequence of SEQ ID NO:8;
(vii) the heavy chain variable region sequence has at least 70% sequence identity to the heavy chain variable region sequence of SEQ ID NO:21, and
the light chain variable region sequence has at least 70% sequence identity to the light chain variable region sequence of SEQ ID NO:9;
or
(viii) the heavy chain variable region sequence has at least 70% sequence identity to the heavy chain variable region sequence of SEQ ID NO:22, and
the light chain variable region sequence has at least 70% sequence identity to the light chain variable region sequence of SEQ ID NO:10;
(ix) the heavy chain variable region sequence has at least 70% sequence identity to the heavy chain variable region sequence of SEQ ID NO:23, and
the light chain variable region sequence has at least 70% sequence identity to the light chain variable region sequence of SEQ ID NO:11;
or
(x) the heavy chain variable region sequence has at least 70% sequence identity to the heavy chain variable region sequence of SEQ ID NO:24, and
the light chain variable region sequence has at least 70% sequence identity to the light chain variable region sequence of SEQ ID NO:12.

15. A method of treating cancer, which comprises administering an antibody or antigen binding fragment to a patient suffering from cancer, wherein the antibody or antigen binding fragment is capable of binding to PD-1, and comprises:

at least one light chain variable region incorporating the following CDRs:

```
                            (SEQ ID NO: 25)
LC-CDR1: SGSSSNIKFNSVN (SEQ ID NO: 26)
LC-CDR2: SNNQRPS (SEQ ID NO: 27)
LC-CDR3: ASWDDVLYGSV, (SEQ ID NO: 30)
SAWDDYLHGTV, (SEQ ID NO: 31)
ASWDDYVRGTM, (SEQ ID NO: 32)
SSWDDFLRGTV, (SEQ ID NO: 33)
SSWDDDARGTI, (SEQ ID NO: 34)
AAWDDVYYGTI, (SEQ ID NO: 35)
ASWDDSLYGTV, (SEQ ID NO: 36)
AAWDDAYYGTI, (SEQ ID NO: 37)
ASWDDVYRGTV
or
                            (SEQ ID NO: 38)
SSWDDSLYGTI;
``` and at least one heavy chain variable region incorporating the following CDRs:

```
                            (SEQ ID NO: 89)
HC-CDR1: SYGMH
or
                            (SEQ ID NO: 39)
GFTFSSYGMH (SEQ ID NO: 40)
HC-CDR2: VISYDGSNKYYADSVKG (SEQ ID NO: 41)
HC-CDR3: DLGAGPYYYGKDH, (SEQ ID NO: 44)
DLGAGPYYYGLDV, (SEQ ID NO: 45)
DLGAGPYYYGMDV, (SEQ ID NO: 46)
DLGAGPYYYGMDV, (SEQ ID NO: 47)
DLGAGPYYYGMDV, (SEQ ID NO: 48)
DLGAGPYYYGMDV, (SEQ ID NO: 49)
DLGAGPYYYGMDV, (SEQ ID NO: 50)
DYGAGPYYYGMDV, (SEQ ID NO: 51)
DLGSGYYLYGMDV,
or
                            (SEQ ID NO: 52)
DLGAGPYYYGMDV.
```

16. The method according to claim 15, wherein the antibody or antigen binding fragment comprises:

(i) at least one light chain variable region incorporating the following CDRs:

```
                            (SEQ ID NO: 25)
LC-CDR1: SGSSSNIKFNSVN (SEQ ID NO: 26)
LC-CDR2: SNNQRPS (SEQ ID NO: 27)
LC-CDR3: ASWDDVLYGSV;
``` and
at least one heavy chain variable region incorporating the following CDRs:

```
                                    (SEQ ID NO: 89)
    HC-CDR1: SYGMH
    or
                                    (SEQ ID NO: 39)
    GFTFSSYGMH
                                    (SEQ ID NO: 40)
    HC-CDR2: VISYDGSNKYYADSVKG
                                    (SEQ ID NO: 41)
    HC-CDR3: DLGAGPYYYGKDH;
``` or
(ii) at least one light chain variable region incorporating the following CDRs:

```
                                    (SEQ ID NO: 25)
    LC-CDR1: SGSSSNIKFNSVN
                                    (SEQ ID NO: 26)
    LC-CDR2: SNNQRPS
                                    (SEQ ID NO: 30)
    LC-CDR3: SAWDDYLHGTV;
``` and
at least one heavy chain variable region incorporating the following CDRs:

```
                                    (SEQ ID NO: 89)
    HC-CDR1: SYGMH
    or
                                    (SEQ ID NO: 39)
    GFTFSSYGMH
                                    (SEQ ID NO: 40)
    HC-CDR2: VISYDGSNKYYADSVKG
                                    (SEQ ID NO: 44)
    HC-CDR3: DLGAGPYYYGLDV;
``` or
(iii) at least one light chain variable region incorporating the following CDRs:

```
                                    (SEQ ID NO: 25)
    LC-CDR1: SGSSSNIKFNSVN
                                    (SEQ ID NO: 26)
    LC-CDR2: SNNQRPS
                                    (SEQ ID NO: 31)
    LC-CDR3: ASWDDYVRGTM;
``` and
at least one heavy chain variable region incorporating the following CDRs:

```
                                    (SEQ ID NO: 89)
    HC-CDR1: SYGMH
    or
                                    (SEQ ID NO: 39)
    GFTFSSYGMH
                                    (SEQ ID NO: 40)
    HC-CDR2: VISYDGSNKYYADSVKG
                                    (SEQ ID NO: 45)
    HC-CDR3: DLGAGPYYYGMDV;
``` or
(iv) at least one light chain variable region incorporating the following CDRs:

```
                                    (SEQ ID NO: 25)
    LC-CDR1: SGSSSNIKFNSVN
                                    (SEQ ID NO: 26)
    LC-CDR2: SNNQRPS
                                    (SEQ ID NO: 32)
    LC-CDR3: SSWDDFLRGTV;
``` and
at least one heavy chain variable region incorporating the following CDRs:

```
                                    (SEQ ID NO: 89)
    HC-CDR1: SYGMH
    or
                                    (SEQ ID NO: 39)
    GFTFSSYGMH
                                    (SEQ ID NO: 40)
    HC-CDR2: VISYDGSNKYYADSVKG
                                    (SEQ ID NO: 46)
    HC-CDR3: DLGAGPYYYGMDV;
``` or
(v) at least one light chain variable region incorporating the following CDRs:

```
                                    (SEQ ID NO: 25)
    LC-CDR1: SGSSSNIKFNSVN
                                    (SEQ ID NO: 26)
    LC-CDR2: SNNQRPS
                                    (SEQ ID NO: 33)
    LC-CDR3: SSWDDDARGTI;
``` and
at least one heavy chain variable region incorporating the following CDRs:

```
                                    (SEQ ID NO: 89)
    HC-CDR1: SYGMH
    or
                                    (SEQ ID NO: 39)
    GFTFSSYGMH
                                    (SEQ ID NO: 40)
    HC-CDR2: VISYDGSNKYYADSVKG
                                    (SEQ ID NO: 47)
    HC-CDR3: DLGAGPYYYGMDV;
``` or
(vi) at least one light chain variable region incorporating the following CDRs:

```
                                    (SEQ ID NO: 25)
    LC-CDR1: SGSSSNIKFNSVN
                                    (SEQ ID NO: 26)
    LC-CDR2: SNNQRPS
```

-continued

```
                                    (SEQ ID NO: 34)
    LC-CDR3: AAWDDVYYGTI;
``` and
at least one heavy chain variable region incorporating the following CDRs:

```
                                    (SEQ ID NO: 89)
    HC-CDR1: SYGMH
    or
                                    (SEQ ID NO: 39)
    GFTFSSYGMH (SEQ ID NO: 40)
    HC-CDR2: VISYDGSNKYYADSVKG (SEQ ID NO: 48)
    HC-CDR3: DLGAGPYYYGMDV;
``` or
(vii) at least one light chain variable region incorporating the following CDRs:

```
                                    (SEQ ID NO: 25)
    LC-CDR1: SGSSSNIKFNSVN (SEQ ID NO: 26)
    LC-CDR2: SNNQRPS (SEQ ID NO: 35)
    LC-CDR3: ASWDDSLYGTV;
``` and
at least one heavy chain variable region incorporating the following CDRs:

```
                                    (SEQ ID NO: 89)
    HC-CDR1: SYGMH
    or
                                    (SEQ ID NO: 39)
    GFTFSSYGMH (SEQ ID NO: 40)
    HC-CDR2: VISYDGSNKYYADSVKG (SEQ ID NO: 49)
    HC-CDR3: DLGAGPYYYGMDV;
``` or
(viii) at least one light chain variable region incorporating the following CDRs:

```
                                    (SEQ ID NO: 25)
    LC-CDR1: SGSSSNIKFNSVN (SEQ ID NO: 26)
    LC-CDR2: SNNQRPS (SEQ ID NO: 36)
    LC-CDR3: AAWDDAYYGTI;
``` and
at least one heavy chain variable region incorporating the following CDRs:

```
                                    (SEQ ID NO: 89)
    HC-CDR1: SYGMH
    or
                                    (SEQ ID NO: 39)
    GFTFSSYGMH
```

```
                                    (SEQ ID NO: 40)
    HC-CDR2: VISYDGSNKYYADSVKG (SEQ ID NO: 50)
    HC-CDR3: DYGAGPYYYGMDV;
``` or
(ix) at least one light chain variable region incorporating the following CDRs:

```
                                    (SEQ ID NO: 25)
    LC-CDR1: SGSSSNIKFNSVN (SEQ ID NO: 26)
    LC-CDR2: SNNQRPS (SEQ ID NO: 37)
    LC-CDR3: ASWDDVYRGTV;
``` and
at least one heavy chain variable region incorporating the following CDRs:

```
                                    (SEQ ID NO: 89)
    HC-CDR1: SYGMH
    or
                                    (SEQ ID NO: 39)
    GFTFSSYGMH (SEQ ID NO: 40)
    HC-CDR2: VISYDGSNKYYADSVKG (SEQ ID NO: 51)
    HC-CDR3: DLGSGYYLYGMDV;
``` or
(x) at least one light chain variable region incorporating the following CDRs:

```
                                    (SEQ ID NO: 25)
    LC-CDR1: SGSSSNIKFNSVN (SEQ ID NO: 26)
    LC-CDR2: SNNQRPS (SEQ ID NO: 38)
    LC-CDR3: SSWDDSLYGTI;
``` and
at least one heavy chain variable region incorporating the following CDRs:

```
                                    (SEQ ID NO: 89)
    HC-CDR1: SYGMH
    or
                                    (SEQ ID NO: 39)
    GFTFSSYGMH (SEQ ID NO: 40)
    HC-CDR2: VISYDGSNKYYADSVKG (SEQ ID NO: 52)
    HC-CDR3: DLGAGPYYYGMDV.
```

17. The method according to claim 15, wherein:
the heavy chain variable region sequence has at least 70% sequence identity to the heavy chain variable region sequence of SEQ ID NO:13, 16, 17, 18, 19, 20, 21, 22, 23 or 24, and
the light chain variable region sequence has at least 70% sequence identity to the light chain variable region sequence of SEQ ID NO:1, 4, 5, 6, 7, 8, 9, 10, 11 or 12.

18. The method according to claim 15, wherein:
(i) the heavy chain variable region sequence has at least 70% sequence identity to the heavy chain variable region sequence of SEQ ID NO:13, and
  the light chain variable region sequence has at least 70% sequence identity to the light chain variable region sequence of SEQ ID NO:1;
or
(ii) the heavy chain variable region sequence has at least 70% sequence identity to the heavy chain variable region sequence of SEQ ID NO:16, and
  the light chain variable region sequence has at least 70% sequence identity to the light chain variable region sequence of SEQ ID NO:4;
(iii) the heavy chain variable region sequence has at least 70% sequence identity to the heavy chain variable region sequence of SEQ ID NO:17, and
  the light chain variable region sequence has at least 70% sequence identity to the light chain variable region sequence of SEQ ID NO:5;
or
(iv) the heavy chain variable region sequence has at least 70% sequence identity to the heavy chain variable region sequence of SEQ ID NO:18, and
  the light chain variable region sequence has at least 70% sequence identity to the light chain variable region sequence of SEQ ID NO:6;
(v) the heavy chain variable region sequence has at least 70% sequence identity to the heavy chain variable region sequence of SEQ ID NO:19, and
  the light chain variable region sequence has at least 70% sequence identity to the light chain variable region sequence of SEQ ID NO:7;
or
(vi) the heavy chain variable region sequence has at least 70% sequence identity to the heavy chain variable region sequence of SEQ ID NO:20, and
  the light chain variable region sequence has at least 70% sequence identity to the light chain variable region sequence of SEQ ID NO:8;
(vii) the heavy chain variable region sequence has at least 70% sequence identity to the heavy chain variable region sequence of SEQ ID NO:21, and
  the light chain variable region sequence has at least 70% sequence identity to the light chain variable region sequence of SEQ ID NO:9;
or
(viii) the heavy chain variable region sequence has at least 70% sequence identity to the heavy chain variable region sequence of SEQ ID NO:22, and
  the light chain variable region sequence has at least 70% sequence identity to the light chain variable region sequence of SEQ ID NO:10;
(ix) the heavy chain variable region sequence has at least 70% sequence identity to the heavy chain variable region sequence of SEQ ID NO:23, and
  the light chain variable region sequence has at least 70% sequence identity to the light chain variable region sequence of SEQ ID NO:11;
or
(x) the heavy chain variable region sequence has at least 70% sequence identity to the heavy chain variable region sequence of SEQ ID NO:24, and
  the light chain variable region sequence has at least 70% sequence identity to the light chain variable region sequence of SEQ ID NO:12.

19. The method according to claim 15, wherein the cancer is a cancer of a tissue selected from the group consisting of lung, kidney, bladder, liver, stomach, cervix, nasopharynx, oral cavity, oesophagus, larynx, salivary gland, tongue, tonsil, trachea, skin, blood, colon and breast.

20. The method according to claim 15, wherein the cancer is selected from the group consisting of lung cancer, non-small cell lung cancer (NSCLC), renal cancer, renal cell carcinoma, bladder cancer, bladder carcinoma, liver cancer, hepatoma, stomach cancer, cervical cancer, nasopharyngeal cancer, oral cavity cancer, oesophageal cancer, laryngeal cancer, salivary gland cancer, tongue cancer, tonsil cancer, tracheal cancer, skin cancer, melanoma, metastatic melanoma, haematologic cancer, lymphoma, Hodgkin's lymphoma, colon cancer, colon carcinoma and breast cancer.

* * * * *

SEQUENCE LISTING

```
<160> NUMBER OF SEQ ID NOS: 89

<210> SEQ ID NO 1
<211> LENGTH: 110
<212> TYPE: PRT
<213> ORGANISM: Artificial sequence
<220> FEATURE:
<223> OTHER INFORMATION: Synthetic sequence: Light chain variable domain
      sequence for anti-PD-1 antibody clone A3

<400> SEQUENCE: 1

Leu Pro Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Lys Phe Asn
            20                  25                  30

Ser Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Phe Cys Ala Ser Trp Asp Asp Val Leu
```

```
                    85                  90                  95

Tyr Gly Ser Val Phe Gly Gly Gly Thr Lys Leu Thr Val Leu
                100                 105                 110

<210> SEQ ID NO 2
<211> LENGTH: 110
<212> TYPE: PRT
<213> ORGANISM: Artificial sequence
<220> FEATURE:
<223> OTHER INFORMATION: Synthetic sequence: Light chain variable domain
      sequence for anti-PD-1 antibody clone A10

<400> SEQUENCE: 2

Leu Pro Val Leu Thr Gln Pro Pro Ser Ala Ser Gly Thr Pro Gly Gln
1               5                   10                  15

Arg Val Thr Ile Ser Cys Ser Gly Ser Ser Asn Ile Lys Phe Asn
            20                  25                  30

Ser Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Phe Cys Ala Ser Trp Asp Asp Tyr Tyr
                85                  90                  95

Tyr Gly Thr Ile Phe Gly Gly Gly Thr Lys Leu Thr Val Leu
                100                 105                 110

<210> SEQ ID NO 3
<211> LENGTH: 110
<212> TYPE: PRT
<213> ORGANISM: Artificial sequence
<220> FEATURE:
<223> OTHER INFORMATION: Synthetic sequence: Light chain variable domain
      sequence for anti-PD-1 antibody clone B6

<400> SEQUENCE: 3

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Lys Phe Asn
            20                  25                  30

Ser Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ser Trp Asp Asp Tyr Leu
                85                  90                  95

Arg Gly Thr Val Phe Gly Gly Gly Thr Lys Leu Thr Val Leu
                100                 105                 110

<210> SEQ ID NO 4
<211> LENGTH: 110
<212> TYPE: PRT
<213> ORGANISM: Artificial sequence
<220> FEATURE:
<223> OTHER INFORMATION: Synthetic sequence: Light chain variable domain
      sequence for anti-PD-1 antibody clone C4

<400> SEQUENCE: 4
```

-continued

Gln Ser Val Leu Thr Gln Pro Pro Ala Ser Gly Thr Pro Gly Gln
1               5                   10                  15

Arg Val Thr Ile Ser Cys Ser Gly Ser Ser Asn Ile Lys Phe Asn
            20                  25                  30

Ser Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ser Ala Trp Asp Asp Tyr Leu
                85                  90                  95

His Gly Thr Val Phe Gly Gly Gly Thr Lys Leu Thr Val Leu
            100                 105                 110

<210> SEQ ID NO 5
<211> LENGTH: 110
<212> TYPE: PRT
<213> ORGANISM: Artificial sequence
<220> FEATURE:
<223> OTHER INFORMATION: Synthetic sequence: Light chain variable domain
      sequence for anti-PD-1 antibody clone D4

<400> SEQUENCE: 5

Gln Ser Val Leu Thr Gln Pro Pro Ala Ser Gly Thr Pro Gly Gln
1               5                   10                  15

Arg Val Thr Ile Ser Cys Ser Gly Ser Ser Asn Ile Lys Phe Asn
            20                  25                  30

Ser Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ser Trp Asp Asp Tyr Val
                85                  90                  95

Arg Gly Thr Met Phe Gly Gly Gly Thr Lys Leu Thr Val Leu
            100                 105                 110

<210> SEQ ID NO 6
<211> LENGTH: 110
<212> TYPE: PRT
<213> ORGANISM: Artificial sequence
<220> FEATURE:
<223> OTHER INFORMATION: Synthetic sequence: Light chain variable domain
      sequence for anti-PD-1 antibody clone E1

<400> SEQUENCE: 6

Gln Ser Val Leu Thr Gln Pro Pro Ala Ser Gly Thr Pro Gly Gln
1               5                   10                  15

Arg Val Thr Ile Ser Cys Ser Gly Ser Ser Asn Ile Lys Phe Asn
            20                  25                  30

Ser Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ser Ser Trp Asp Asp Phe Leu
                85                  90                  95

Arg Gly Thr Val Phe Gly Gly Gly Thr Lys Leu Thr Val Leu
            100                 105                 110

<210> SEQ ID NO 7
<211> LENGTH: 110
<212> TYPE: PRT
<213> ORGANISM: Artificial sequence
<220> FEATURE:
<223> OTHER INFORMATION: Synthetic sequence: Light chain variable domain
      sequence for anti-PD-1 antibody clone F2

<400> SEQUENCE: 7

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Lys Phe Asn
                20                  25                  30

Ser Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ser Ser Trp Asp Asp Ala
                85                  90                  95

Arg Gly Thr Ile Phe Gly Gly Gly Thr Lys Leu Thr Val Leu
            100                 105                 110

<210> SEQ ID NO 8
<211> LENGTH: 110
<212> TYPE: PRT
<213> ORGANISM: Artificial sequence
<220> FEATURE:
<223> OTHER INFORMATION: Synthetic sequence: Light chain variable domain
      sequence for anti-PD-1 antibody clone G1

<400> SEQUENCE: 8

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Lys Phe Asn
                20                  25                  30

Ser Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Val Tyr
                85                  90                  95

Tyr Gly Thr Ile Phe Gly Gly Gly Thr Lys Leu Thr Val Leu
            100                 105                 110

<210> SEQ ID NO 9
<211> LENGTH: 110
<212> TYPE: PRT
<213> ORGANISM: Artificial sequence
<220> FEATURE:
<223> OTHER INFORMATION: Synthetic sequence: Light chain variable domain
      sequence for anti-PD-1 antibody clone G2

-continued

<400> SEQUENCE: 9

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Lys Phe Asn
            20                  25                  30

Ser Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ser Trp Asp Asp Ser Leu
                85                  90                  95

Tyr Gly Thr Val Phe Gly Gly Gly Thr Lys Leu Thr Val Leu
            100                 105                 110

<210> SEQ ID NO 10
<211> LENGTH: 110
<212> TYPE: PRT
<213> ORGANISM: Artificial sequence
<220> FEATURE:
<223> OTHER INFORMATION: Synthetic sequence: Light chain variable domain
      sequence for anti-PD-1 antibody clone G10

<400> SEQUENCE: 10

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Lys Phe Asn
            20                  25                  30

Ser Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ala Tyr
                85                  90                  95

Tyr Gly Thr Ile Phe Gly Gly Gly Thr Lys Leu Thr Val Leu
            100                 105                 110

<210> SEQ ID NO 11
<211> LENGTH: 110
<212> TYPE: PRT
<213> ORGANISM: Artificial sequence
<220> FEATURE:
<223> OTHER INFORMATION: Synthetic sequence: Light chain variable domain
      sequence for anti-PD-1 antibody clone H4

<400> SEQUENCE: 11

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Lys Phe Asn
            20                  25                  30

Ser Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

```
Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ser Trp Asp Asp Val Tyr
                85                  90                  95

Arg Gly Thr Val Phe Gly Gly Gly Thr Lys Leu Thr Val Leu
            100                 105                 110

<210> SEQ ID NO 12
<211> LENGTH: 110
<212> TYPE: PRT
<213> ORGANISM: Artificial sequence
<220> FEATURE:
<223> OTHER INFORMATION: Synthetic sequence: Light chain variable domain
      sequence for anti-PD-1 antibody clone H9

<400> SEQUENCE: 12

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Lys Phe Asn
            20                  25                  30

Ser Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ser Ser Trp Asp Asp Ser Leu
                85                  90                  95

Tyr Gly Thr Ile Phe Gly Gly Gly Thr Lys Leu Thr Val Leu
            100                 105                 110

<210> SEQ ID NO 13
<211> LENGTH: 122
<212> TYPE: PRT
<213> ORGANISM: Artificial sequence
<220> FEATURE:
<223> OTHER INFORMATION: Synthetic sequence: Heavy chain variable domain
      sequence for anti-PD-1 antibody clone A3

<400> SEQUENCE: 13

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Asp Leu Gly Ala Gly Pro Tyr Tyr Tyr Gly Lys Asp His Trp
            100                 105                 110

Gly Gln Gly Thr Thr Val Thr Val Ser Ser
            115                 120

<210> SEQ ID NO 14
<211> LENGTH: 122
```

```
<212> TYPE: PRT
<213> ORGANISM: Artificial sequence
<220> FEATURE:
<223> OTHER INFORMATION: Synthetic sequence: Heavy chain variable domain
      sequence for anti-PD-1 antibody clone A10

<400> SEQUENCE: 14

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Asp Leu Gly Ala Gly Pro Tyr Tyr Tyr Gly Lys Asp Val Trp
            100                 105                 110

Gly Gln Gly Thr Thr Val Thr Val Ser Ser
        115                 120

<210> SEQ ID NO 15
<211> LENGTH: 122
<212> TYPE: PRT
<213> ORGANISM: Artificial sequence
<220> FEATURE:
<223> OTHER INFORMATION: Synthetic sequence: Heavy chain variable domain
      sequence for anti-PD-1 antibody clone B6

<400> SEQUENCE: 15

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Asp Tyr Gly Ala Gly Pro Tyr Tyr Tyr Gly Met Asp Val Trp
            100                 105                 110

Gly Gln Gly Thr Thr Val Thr Val Ser Ser
        115                 120

<210> SEQ ID NO 16
<211> LENGTH: 122
<212> TYPE: PRT
<213> ORGANISM: Artificial sequence
<220> FEATURE:
<223> OTHER INFORMATION: Synthetic sequence: Heavy chain variable domain
      sequence for anti-PD-1 antibody clone C4

<400> SEQUENCE: 16

Gln Val Gln Leu Val Glu Ser Gly Gly Gly Val Val Gln Pro Gly Arg
```

```
                1               5                  10                  15
            Ser Leu Arg Leu Ser Cys Ala Ala Ser Gly Phe Thr Phe Ser Ser Tyr
                        20                  25                  30

Gly Met His Trp Val Arg Gln Ala Pro Gly Lys Gly Leu Glu Trp Val
                        35                  40                  45

Ala Val Ile Ser Tyr Asp Gly Ser Asn Lys Tyr Tyr Ala Asp Ser Val
                        50                  55                  60

Lys Gly Arg Phe Thr Ile Ser Arg Asp Asn Ser Lys Asn Thr Leu Tyr
             65                  70                  75                  80

Leu Gln Met Asn Ser Leu Arg Ala Glu Asp Thr Ala Val Tyr Tyr Cys
                        85                  90                  95

Ala Ser Asp Leu Gly Ala Gly Pro Tyr Tyr Tyr Gly Leu Asp Val Trp
                        100                 105                 110

Gly Gln Gly Thr Thr Val Thr Val Ser Ser
                        115                 120

<210> SEQ ID NO 17
<211> LENGTH: 122
<212> TYPE: PRT
<213> ORGANISM: Artificial sequence
<220> FEATURE:
<223> OTHER INFORMATION: Synthetic sequence: Heavy chain variable domain
      sequence for anti-PD-1 antibody clone D4

<400> SEQUENCE: 17

Gln Val Gln Leu Val Glu Ser Gly Gly Gly Val Val Gln Pro Gly Arg
             1               5                  10                  15

Ser Leu Arg Leu Ser Cys Ala Ala Ser Gly Phe Thr Phe Ser Ser Tyr
                        20                  25                  30

Gly Met His Trp Val Arg Gln Ala Pro Gly Lys Gly Leu Glu Trp Val
                        35                  40                  45

Ala Val Ile Ser Tyr Asp Gly Ser Asn Lys Tyr Tyr Ala Asp Ser Val
                        50                  55                  60

Lys Gly Arg Phe Thr Ile Ser Arg Asp Asn Ser Lys Asn Thr Leu Tyr
             65                  70                  75                  80

Leu Gln Met Asn Ser Leu Arg Ala Glu Asp Thr Ala Val Tyr Tyr Cys
                        85                  90                  95

Ala Ser Asp Leu Gly Ala Gly Pro Tyr Tyr Tyr Gly Met Asp Val Trp
                        100                 105                 110

Gly Gln Gly Thr Thr Val Thr Val Ser Ser
                        115                 120

<210> SEQ ID NO 18
<211> LENGTH: 122
<212> TYPE: PRT
<213> ORGANISM: Artificial sequence
<220> FEATURE:
<223> OTHER INFORMATION: Synthetic sequence: Heavy chain variable domain
      sequence for anti-PD-1 antibody clone E1

<400> SEQUENCE: 18

Gln Val Gln Leu Val Glu Ser Gly Gly Gly Val Val Gln Pro Gly Arg
             1               5                  10                  15

Ser Leu Arg Leu Ser Cys Ala Ala Ser Gly Phe Thr Phe Ser Ser Tyr
                        20                  25                  30

Gly Met His Trp Val Arg Gln Ala Pro Gly Lys Gly Leu Glu Trp Val
                        35                  40                  45

Ala Val Ile Ser Tyr Asp Gly Ser Asn Lys Tyr Tyr Ala Asp Ser Val
```

```
                     50                   55                   60
Lys Gly Arg Phe Thr Ile Ser Arg Asp Asn Ser Lys Asn Thr Leu Tyr
 65                   70                   75                   80

Leu Gln Met Asn Ser Leu Arg Ala Glu Asp Thr Ala Val Tyr Tyr Cys
                     85                   90                   95

Ala Ser Asp Leu Gly Ala Gly Pro Tyr Tyr Tyr Gly Met Asp Val Trp
                100                  105                  110

Gly Gln Gly Thr Thr Val Thr Val Ser Ser
            115                  120

<210> SEQ ID NO 19
<211> LENGTH: 122
<212> TYPE: PRT
<213> ORGANISM: Artificial sequence
<220> FEATURE:
<223> OTHER INFORMATION: Synthetic sequence: Heavy chain variable domain
      sequence for anti-PD-1 antibody clone F2

<400> SEQUENCE: 19

Gln Val Gln Leu Val Glu Ser Gly Gly Gly Val Val Gln Pro Gly Arg
  1               5                   10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Ser Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                   80

Leu Gln Met Asn Ser Leu Arg Ala Glu Asp Thr Ala Val Tyr Tyr Cys
                 85                  90                   95

Ala Ser Asp Leu Gly Ala Gly Pro Tyr Tyr Tyr Gly Met Asp Val Trp
             100                 105                  110

Gly Gln Gly Thr Thr Val Thr Val Ser Ser
         115                 120

<210> SEQ ID NO 20
<211> LENGTH: 122
<212> TYPE: PRT
<213> ORGANISM: Artificial sequence
<220> FEATURE:
<223> OTHER INFORMATION: Synthetic sequence: Heavy chain variable domain
      sequence for anti-PD-1 antibody clone G1

<400> SEQUENCE: 20

Gln Val Gln Leu Val Glu Ser Gly Gly Gly Val Val Gln Pro Gly Arg
  1               5                   10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Ser Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                   80

Leu Gln Met Asn Ser Leu Arg Ala Glu Asp Thr Ala Val Tyr Tyr Cys
                 85                  90                   95

Ala Ser Asp Leu Gly Ala Gly Pro Tyr Tyr Tyr Gly Met Asp Val Trp
```

```
                        100                 105                 110
Gly Gln Gly Thr Thr Val Thr Val Ser Ser
            115                 120

<210> SEQ ID NO 21
<211> LENGTH: 122
<212> TYPE: PRT
<213> ORGANISM: Artificial sequence
<220> FEATURE:
<223> OTHER INFORMATION: Synthetic sequence: Heavy chain variable domain
      sequence for anti-PD-1 antibody clone G2

<400> SEQUENCE: 21

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Asp Leu Gly Ala Gly Pro Tyr Tyr Tyr Gly Met Asp Val Trp
            100                 105                 110

Gly Gln Gly Thr Thr Val Thr Val Ser Ser
            115                 120

<210> SEQ ID NO 22
<211> LENGTH: 122
<212> TYPE: PRT
<213> ORGANISM: Artificial sequence
<220> FEATURE:
<223> OTHER INFORMATION: Synthetic sequence: Heavy chain variable domain
      sequence for anti-PD-1 antibody clone G10

<400> SEQUENCE: 22

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Asp Tyr Gly Ala Gly Pro Tyr Tyr Tyr Gly Met Asp Val Trp
            100                 105                 110

Gly Gln Gly Thr Thr Val Thr Val Ser Ser
            115                 120

<210> SEQ ID NO 23
<211> LENGTH: 122
<212> TYPE: PRT
```

<213> ORGANISM: Artificial sequence
<220> FEATURE:
<223> OTHER INFORMATION: Synthetic sequence: Heavy chain variable domain
      sequence for anti-PD-1 antibody clone H4

<400> SEQUENCE: 23

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Asp Leu Gly Ser Gly Tyr Tyr Leu Tyr Gly Met Asp Val Trp
            100                 105                 110

Gly Gln Gly Thr Thr Val Thr Val Ser Ser
        115                 120
```

<210> SEQ ID NO 24
<211> LENGTH: 122
<212> TYPE: PRT
<213> ORGANISM: Artificial sequence
<220> FEATURE:
<223> OTHER INFORMATION: Synthetic sequence: Heavy chain variable domain
      sequence for anti-PD-1 antibody clone H9

<400> SEQUENCE: 24

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Asp Leu Gly Ala Gly Pro Tyr Tyr Tyr Gly Met Asp Val Trp
            100                 105                 110

Gly Gln Gly Thr Thr Val Thr Val Ser Ser
        115                 120
```

<210> SEQ ID NO 25
<211> LENGTH: 13
<212> TYPE: PRT
<213> ORGANISM: Artificial sequence
<220> FEATURE:
<223> OTHER INFORMATION: Synthetic sequence: LC-CDR1

<400> SEQUENCE: 25

```
Ser Gly Ser Ser Ser Asn Ile Lys Phe Asn Ser Val Asn
1               5                   10
```

```
<210> SEQ ID NO 26
<211> LENGTH: 7
<212> TYPE: PRT
<213> ORGANISM: Artificial sequence
<220> FEATURE:
<223> OTHER INFORMATION: Synthetic sequence: LC-CDR2

<400> SEQUENCE: 26

Ser Asn Asn Gln Arg Pro Ser
1               5

<210> SEQ ID NO 27
<211> LENGTH: 11
<212> TYPE: PRT
<213> ORGANISM: Artificial sequence
<220> FEATURE:
<223> OTHER INFORMATION: Synthetic sequence: LC-CDR3

<400> SEQUENCE: 27

Ala Ser Trp Asp Asp Val Leu Tyr Gly Ser Val
1               5                   10

<210> SEQ ID NO 28
<211> LENGTH: 11
<212> TYPE: PRT
<213> ORGANISM: Artificial sequence
<220> FEATURE:
<223> OTHER INFORMATION: Synthetic sequence: LC-CDR3

<400> SEQUENCE: 28

Ala Ser Trp Asp Asp Tyr Tyr Tyr Gly Thr Ile
1               5                   10

<210> SEQ ID NO 29
<211> LENGTH: 11
<212> TYPE: PRT
<213> ORGANISM: Artificial sequence
<220> FEATURE:
<223> OTHER INFORMATION: Synthetic sequence: LC-CDR3

<400> SEQUENCE: 29

Ala Ser Trp Asp Asp Tyr Leu Arg Gly Thr Val
1               5                   10

<210> SEQ ID NO 30
<211> LENGTH: 11
<212> TYPE: PRT
<213> ORGANISM: Artificial sequence
<220> FEATURE:
<223> OTHER INFORMATION: Synthetic sequence: LC-CDR3

<400> SEQUENCE: 30

Ser Ala Trp Asp Asp Tyr Leu His Gly Thr Val
1               5                   10

<210> SEQ ID NO 31
<211> LENGTH: 11
<212> TYPE: PRT
<213> ORGANISM: Artificial sequence
<220> FEATURE:
<223> OTHER INFORMATION: Synthetic sequence: LC-CDR3

<400> SEQUENCE: 31

Ala Ser Trp Asp Asp Tyr Val Arg Gly Thr Met
1               5                   10
```

```
<210> SEQ ID NO 32
<211> LENGTH: 11
<212> TYPE: PRT
<213> ORGANISM: Artificial sequence
<220> FEATURE:
<223> OTHER INFORMATION: Synthetic sequence: LC-CDR3

<400> SEQUENCE: 32

Ser Ser Trp Asp Asp Phe Leu Arg Gly Thr Val
1               5                   10

<210> SEQ ID NO 33
<211> LENGTH: 11
<212> TYPE: PRT
<213> ORGANISM: Artificial sequence
<220> FEATURE:
<223> OTHER INFORMATION: Synthetic sequence: LC-CDR3

<400> SEQUENCE: 33

Ser Ser Trp Asp Asp Asp Ala Arg Gly Thr Ile
1               5                   10

<210> SEQ ID NO 34
<211> LENGTH: 11
<212> TYPE: PRT
<213> ORGANISM: Artificial sequence
<220> FEATURE:
<223> OTHER INFORMATION: Synthetic sequence: LC-CDR3

<400> SEQUENCE: 34

Ala Ala Trp Asp Asp Val Tyr Tyr Gly Thr Ile
1               5                   10

<210> SEQ ID NO 35
<211> LENGTH: 11
<212> TYPE: PRT
<213> ORGANISM: Artificial sequence
<220> FEATURE:
<223> OTHER INFORMATION: Synthetic sequence: LC-CDR3

<400> SEQUENCE: 35

Ala Ser Trp Asp Asp Ser Leu Tyr Gly Thr Val
1               5                   10

<210> SEQ ID NO 36
<211> LENGTH: 11
<212> TYPE: PRT
<213> ORGANISM: Artificial sequence
<220> FEATURE:
<223> OTHER INFORMATION: Synthetic sequence: LC-CDR3

<400> SEQUENCE: 36

Ala Ala Trp Asp Asp Ala Tyr Tyr Gly Thr Ile
1               5                   10

<210> SEQ ID NO 37
<211> LENGTH: 11
<212> TYPE: PRT
<213> ORGANISM: Artificial sequence
<220> FEATURE:
<223> OTHER INFORMATION: Synthetic sequence: LC-CDR3

<400> SEQUENCE: 37

Ala Ser Trp Asp Asp Val Tyr Arg Gly Thr Val
1               5                   10

<210> SEQ ID NO 38
```

```
<211> LENGTH: 11
<212> TYPE: PRT
<213> ORGANISM: Artificial sequence
<220> FEATURE:
<223> OTHER INFORMATION: Synthetic sequence: LC-CDR3

<400> SEQUENCE: 38

Ser Ser Trp Asp Asp Ser Leu Tyr Gly Thr Ile
1               5                   10

<210> SEQ ID NO 39
<211> LENGTH: 10
<212> TYPE: PRT
<213> ORGANISM: Artificial sequence
<220> FEATURE:
<223> OTHER INFORMATION: Synthetic sequence: HC-CDR1

<400> SEQUENCE: 39

Gly Phe Thr Phe Ser Ser Tyr Gly Met His
1               5                   10

<210> SEQ ID NO 40
<211> LENGTH: 17
<212> TYPE: PRT
<213> ORGANISM: Artificial sequence
<220> FEATURE:
<223> OTHER INFORMATION: Synthetic sequence: HC-CDR2

<400> SEQUENCE: 40

Val Ile Ser Tyr Asp Gly Ser Asn Lys Tyr Tyr Ala Asp Ser Val Lys
1               5                   10                  15

Gly

<210> SEQ ID NO 41
<211> LENGTH: 13
<212> TYPE: PRT
<213> ORGANISM: Artificial sequence
<220> FEATURE:
<223> OTHER INFORMATION: Synthetic sequence: HC-CDR3

<400> SEQUENCE: 41

Asp Leu Gly Ala Gly Pro Tyr Tyr Tyr Gly Lys Asp His
1               5                   10

<210> SEQ ID NO 42
<211> LENGTH: 13
<212> TYPE: PRT
<213> ORGANISM: Artificial sequence
<220> FEATURE:
<223> OTHER INFORMATION: Synthetic sequence: HC-CDR3

<400> SEQUENCE: 42

Asp Leu Gly Ala Gly Pro Tyr Tyr Tyr Gly Lys Asp Val
1               5                   10

<210> SEQ ID NO 43
<211> LENGTH: 13
<212> TYPE: PRT
<213> ORGANISM: Artificial sequence
<220> FEATURE:
<223> OTHER INFORMATION: Synthetic sequence: HC-CDR3

<400> SEQUENCE: 43

Asp Tyr Gly Ala Gly Pro Tyr Tyr Tyr Gly Met Asp Val
1               5                   10
```

```
<210> SEQ ID NO 44
<211> LENGTH: 13
<212> TYPE: PRT
<213> ORGANISM: Artificial sequence
<220> FEATURE:
<223> OTHER INFORMATION: Synthetic sequence: HC-CDR3

<400> SEQUENCE: 44

Asp Leu Gly Ala Gly Pro Tyr Tyr Tyr Gly Leu Asp Val
1               5                   10

<210> SEQ ID NO 45
<211> LENGTH: 13
<212> TYPE: PRT
<213> ORGANISM: Artificial sequence
<220> FEATURE:
<223> OTHER INFORMATION: Synthetic sequence: HC-CDR3

<400> SEQUENCE: 45

Asp Leu Gly Ala Gly Pro Tyr Tyr Tyr Gly Met Asp Val
1               5                   10

<210> SEQ ID NO 46
<211> LENGTH: 13
<212> TYPE: PRT
<213> ORGANISM: Artificial sequence
<220> FEATURE:
<223> OTHER INFORMATION: Synthetic sequence: HC-CDR3

<400> SEQUENCE: 46

Asp Leu Gly Ala Gly Pro Tyr Tyr Tyr Gly Met Asp Val
1               5                   10

<210> SEQ ID NO 47
<211> LENGTH: 13
<212> TYPE: PRT
<213> ORGANISM: Artificial sequence
<220> FEATURE:
<223> OTHER INFORMATION: Synthetic sequence: HC-CDR3

<400> SEQUENCE: 47

Asp Leu Gly Ala Gly Pro Tyr Tyr Tyr Gly Met Asp Val
1               5                   10

<210> SEQ ID NO 48
<211> LENGTH: 13
<212> TYPE: PRT
<213> ORGANISM: Artificial sequence
<220> FEATURE:
<223> OTHER INFORMATION: Synthetic sequence: HC-CDR3

<400> SEQUENCE: 48

Asp Leu Gly Ala Gly Pro Tyr Tyr Tyr Gly Met Asp Val
1               5                   10

<210> SEQ ID NO 49
<211> LENGTH: 13
<212> TYPE: PRT
<213> ORGANISM: Artificial sequence
<220> FEATURE:
<223> OTHER INFORMATION: Synthetic sequence: HC-CDR3

<400> SEQUENCE: 49

Asp Leu Gly Ala Gly Pro Tyr Tyr Tyr Gly Met Asp Val
1               5                   10

<210> SEQ ID NO 50
```

```
<211> LENGTH: 13
<212> TYPE: PRT
<213> ORGANISM: Artificial sequence
<220> FEATURE:
<223> OTHER INFORMATION: Synthetic sequence: HC-CDR3

<400> SEQUENCE: 50

Asp Tyr Gly Ala Gly Pro Tyr Tyr Tyr Gly Met Asp Val
1               5                   10

<210> SEQ ID NO 51
<211> LENGTH: 13
<212> TYPE: PRT
<213> ORGANISM: Artificial sequence
<220> FEATURE:
<223> OTHER INFORMATION: Synthetic sequence: HC-CDR3

<400> SEQUENCE: 51

Asp Leu Gly Ser Gly Tyr Tyr Leu Tyr Gly Met Asp Val
1               5                   10

<210> SEQ ID NO 52
<211> LENGTH: 13
<212> TYPE: PRT
<213> ORGANISM: Artificial sequence
<220> FEATURE:
<223> OTHER INFORMATION: Synthetic sequence: HC-CDR3

<400> SEQUENCE: 52

Asp Leu Gly Ala Gly Pro Tyr Tyr Tyr Gly Met Asp Val
1               5                   10

<210> SEQ ID NO 53
<211> LENGTH: 11
<212> TYPE: PRT
<213> ORGANISM: Artificial sequence
<220> FEATURE:
<223> OTHER INFORMATION: Synthetic sequence: LC-CDR3
<220> FEATURE:
<221> NAME/KEY: VARIANT
<222> LOCATION: (1)..(1)
<223> OTHER INFORMATION: Xaa= Ala or Ser
<220> FEATURE:
<221> NAME/KEY: VARIANT
<222> LOCATION: (2)..(2)
<223> OTHER INFORMATION: Xaa= Ser or Ala
<220> FEATURE:
<221> NAME/KEY: VARIANT
<222> LOCATION: (6)..(6)
<223> OTHER INFORMATION: Xaa= Val, Tyr, Phe, Asp, Ser or Ala
<220> FEATURE:
<221> NAME/KEY: VARIANT
<222> LOCATION: (7)..(7)
<223> OTHER INFORMATION: Xaa= Leu, Tyr, Val or Ala
<220> FEATURE:
<221> NAME/KEY: VARIANT
<222> LOCATION: (8)..(8)
<223> OTHER INFORMATION: Xaa= Tyr, Arg or His
<220> FEATURE:
<221> NAME/KEY: VARIANT
<222> LOCATION: (10)..(10)
<223> OTHER INFORMATION: Xaa= Ser, or Thr
<220> FEATURE:
<221> NAME/KEY: VARIANT
<222> LOCATION: (11)..(11)
<223> OTHER INFORMATION: Xaa= Val, Ile, or Met

<400> SEQUENCE: 53

Xaa Xaa Trp Asp Asp Xaa Xaa Xaa Gly Xaa Xaa
1               5                   10
```

```
<210> SEQ ID NO 54
<211> LENGTH: 13
<212> TYPE: PRT
<213> ORGANISM: Artificial sequence
<220> FEATURE:
<223> OTHER INFORMATION: Synthetic sequence: HC-CDR3
<220> FEATURE:
<221> NAME/KEY: VARIANT
<222> LOCATION: (2)..(2)
<223> OTHER INFORMATION: Xaa= Leu or Tyr
<220> FEATURE:
<221> NAME/KEY: VARIANT
<222> LOCATION: (4)..(4)
<223> OTHER INFORMATION: Xaa= Ala or Ser
<220> FEATURE:
<221> NAME/KEY: VARIANT
<222> LOCATION: (6)..(6)
<223> OTHER INFORMATION: Xaa= Pro or Tyr
<220> FEATURE:
<221> NAME/KEY: VARIANT
<222> LOCATION: (8)..(8)
<223> OTHER INFORMATION: Xaa= Tyr or Leu
<220> FEATURE:
<221> NAME/KEY: VARIANT
<222> LOCATION: (11)..(11)
<223> OTHER INFORMATION: Xaa= Lys, Met or Leu
<220> FEATURE:
<221> NAME/KEY: VARIANT
<222> LOCATION: (13)..(13)
<223> OTHER INFORMATION: Xaa= His or Val

<400> SEQUENCE: 54

Asp Xaa Gly Xaa Gly Xaa Tyr Xaa Tyr Gly Xaa Asp Xaa
1               5                   10

<210> SEQ ID NO 55
<211> LENGTH: 330
<212> TYPE: DNA
<213> ORGANISM: Artificial sequence
<220> FEATURE:
<223> OTHER INFORMATION: Synthetic sequence: Nucleotide sequence of
      light chain variable domain sequence for anti-PD-1 antibody clone
      A3

<400> SEQUENCE: 55
ctgcctgtgc tgactcagcc cccctcagcg tccgggaccc ccgggcagag ggtcaccatc      60
tcttgttctg gaagcagctc caacatcaaa tttaacagtg ttaactggta tcagcaactc     120
ccaggaacgg cccccaaact cctcatctat agtaataatc agcgaccctc aggggtccct     180
gaccgattct ctggctccaa gtctggcact tcagcctccc tggccatcag tgggctccag     240
tctgaggatg aggctgatta tttctgtgct tcttgggatg atgttcttta tgatctgtg      300 ttcggcggag ggaccaagct gaccgtcctg                                     330

<210> SEQ ID NO 56
<211> LENGTH: 330
<212> TYPE: DNA
<213> ORGANISM: Artificial sequence
<220> FEATURE:
<223> OTHER INFORMATION: Synthetic sequence: Nucleotide sequence of
      light chain variable domain sequence for anti-PD-1 antibody clone
      A10

<400> SEQUENCE: 56
ctgcctgtgc tgactcagcc cccctcagcg tccgggaccc ccgggcagag ggtcaccatc      60
tcttgttctg gaagcagctc caacatcaaa tttaacagtg ttaactggta tcagcaactc     120
ccaggaacgg cccccaaact cctcatctat agtaataatc agcgaccctc aggggtccct     180
gaccgattct ctggctccaa gtctggcact tcagcctccc tggccatcag tgggctccag     240
```

```
tctgaggatg aggctgatta tttctgtgct tcttgggatg attattatta tggaactatt    300
ttcggcggag ggaccaagct gaccgtcctg                                     330
```

<210> SEQ ID NO 57
<211> LENGTH: 110
<212> TYPE: PRT
<213> ORGANISM: Artificial sequence
<220> FEATURE:
<223> OTHER INFORMATION: Synthetic sequence: Encoded amino acid sequence
of light chain variable domain sequence for anti-PD-1 antibody
codon-optimised clone A10

<400> SEQUENCE: 57

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Lys Phe Asn
            20                  25                  30

Ser Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ser Trp Asp Asp Tyr Tyr
                85                  90                  95

Tyr Gly Thr Ile Phe Gly Gly Gly Thr Lys Leu Thr Val Leu
            100                 105                 110
```

<210> SEQ ID NO 58
<211> LENGTH: 330
<212> TYPE: DNA
<213> ORGANISM: Artificial sequence
<220> FEATURE:
<223> OTHER INFORMATION: Synthetic sequence: Nucleotide sequence of
light chain variable domain sequence for anti-PD-1 antibody
codon-optimised clone A10

<400> SEQUENCE: 58

```
cagagcgtcc tgacacagcc tcctagtgca agcggaaccc ctgggcagag agtgaccatt    60
tcttgtagcg gcagcagcag taacatcaag ttcaactccg tgaattggta tcagcagctg    120
cccggaactg ctcctaaact gctgatctac tctaacaatc agcgaccaag tggcgtcccc    180
gaccggttca gcggctccaa gtctgggacc agtgcctcac tggctatcag cgggctccag    240
tccgaggacg aagcagatta ctattgcgcc agctgggacg attactatta cggcaccatt    300
ttcggcgggg gaacaaaact gaccgtcctg                                     330
```

<210> SEQ ID NO 59
<211> LENGTH: 330
<212> TYPE: DNA
<213> ORGANISM: Artificial sequence
<220> FEATURE:
<223> OTHER INFORMATION: Synthetic sequence: Nucleotide sequence of
light chain variable domain sequence for anti-PD-1 antibody clone
B6

<400> SEQUENCE: 59

```
cagtctgtgc tgactcagcc cccctcagcg tccgggaccc ccgggcagag ggtcaccatc    60
tcttgttctg gaagcagctc caacatcaaa tttaacagtg ttaactggta tcagcaactc    120
ccaggaacgg cccccaaact cctcatctat agtaataatc agcgaccctc agggggtccct   180
```

```
gaccgattct ctggctccaa gtctggcact cagcctccc tggccatcag tgggctccag      240
tctgaggatg aggctgatta ttactgtgct tcttgggatg attatcttcg tggaactgtt      300
ttcggcggag ggaccaagct gaccgtcctg                                        330
```

<210> SEQ ID NO 60
<211> LENGTH: 330
<212> TYPE: DNA
<213> ORGANISM: Artificial sequence
<220> FEATURE:
<223> OTHER INFORMATION: Synthetic sequence: Nucleotide sequence of
      light chain variable domain sequence for anti-PD-1 antibody
      codon-optimised clone B6

<400> SEQUENCE: 60

```
cagagcgtgc tgacccagcc ccccagcgcc agtggaacac ccggacagag agtgaccatc      60
agttgctcag gcagctcctc taacattaag ttcaactctg tgaattggta tcagcagctg      120
cccggaactg ctcctaaact gctgatctat tctaacaatc agcgaccaag tggcgtcccc      180
gaccggttca gcggctccaa gtctgggacc agtgcctcac tggctattag cgggctccag      240
tccgaggacg aagcagatta ctattgtgcc agctgggacg attacctgag gggcaccgtg      300
ttcggaggag gaacaaaact gaccgtcctg                                        330
```

<210> SEQ ID NO 61
<211> LENGTH: 330
<212> TYPE: DNA
<213> ORGANISM: Artificial sequence
<220> FEATURE:
<223> OTHER INFORMATION: Synthetic sequence: Nucleotide sequence of
      light chain variable domain sequence for anti-PD-1 antibody clone
      C4

<400> SEQUENCE: 61

```
cagtctgtgc tgactcagcc cccctcagcg tccgggaccc ccgggcagag ggtcaccatc      60
tcttgttctg gaagcagctc caacatcaaa tttaacagtg ttaactggta tcagcaactc      120
ccaggaacgg cccccaaact cctcatctat agtaataatc agcgaccctc aggggtccct      180
gaccgattct ctggctccaa gtctggcact cagcctccc tggccatcag tgggctccag      240
tctgaggatg aggctgatta ttactgttct gcttgggatg attatcttca tggaactgtg      300
ttcggcggag ggaccaagct gaccgtcctg                                        330
```

<210> SEQ ID NO 62
<211> LENGTH: 330
<212> TYPE: DNA
<213> ORGANISM: Artificial sequence
<220> FEATURE:
<223> OTHER INFORMATION: Synthetic sequence: Nucleotide sequence of
      light chain variable domain sequence for anti-PD-1 antibody
      codon-optimised clone C4

<400> SEQUENCE: 62

```
cagagcgtcc tgacacagcc ccttccgca agtggaaccc ctgggcagcg agtgactatt      60
tcatgcagtg gatcttcatc taacatcaag ttcaactccg tgaattggta tcagcagctg      120
cccggaactg ctcctaaact gctgatctat tctaacaatc agcgaccaag tggcgtcccc      180
gaccggttca gcggctccaa gtctgggacc agtgcctcac tggctattag cgggctccag      240
tccgaggacg aagcagatta ctattgcagc gcctgggacg attacctgca cggcaccgtg      300
ttcggaggag gaacaaaact gaccgtcctg                                        330
```

<210> SEQ ID NO 63
<211> LENGTH: 330
<212> TYPE: DNA
<213> ORGANISM: Artificial sequence
<220> FEATURE:
<223> OTHER INFORMATION: Synthetic sequence: Nucleotide sequence of
      light chain variable domain sequence for anti-PD-1 antibody clone
      D4

<400> SEQUENCE: 63
cagtctgtgc tgactcagcc cccctcagcg tccgggaccc ccgggcagag ggtcaccatc      60
tcttgttctg gaagcagctc caacatcaaa tttaacagtg ttaactggta tcagcaactc    120
ccaggaacgg cccccaaact cctcatctat agtaataatc agcgaccctc aggggtccct    180
gaccgattct ctggctccaa gtctggcact tcagcctccc tggccatcag tgggctccag    240
tctgaggatg aggctgatta ttactgtgct tcttgggatg attatgttcg tggaactatg    300
ttcggcggag ggaccaagct gaccgtcctg                                     330

<210> SEQ ID NO 64
<211> LENGTH: 330
<212> TYPE: DNA
<213> ORGANISM: Artificial sequence
<220> FEATURE:
<223> OTHER INFORMATION: Synthetic sequence: Nucleotide sequence of
      light chain variable domain sequence for anti-PD-1 antibody clone
      E1

<400> SEQUENCE: 64
cagtctgtgc tgactcagcc cccctcagcg tccgggaccc ccgggcagag ggtcaccatc      60
tcttgttctg gaagcagctc caacatcaaa tttaacagtg ttaactggta tcagcaactc    120
ccaggaacgg cccccaaact cctcatctat agtaataatc agcgaccctc aggggtccct    180
gaccgattct ctggctccaa gtctggcact tcagcctccc tggccatcag tgggctccag    240
tctgaggatg aggctgatta ttactgttct tcttgggatg attttcttcg tggaactgtt    300
ttcggcggag ggaccaagct gaccgtcctg                                     330

<210> SEQ ID NO 65
<211> LENGTH: 330
<212> TYPE: DNA
<213> ORGANISM: Artificial sequence
<220> FEATURE:
<223> OTHER INFORMATION: Synthetic sequence: Nucleotide sequence of
      light chain variable domain sequence for anti-PD-1 antibody clone
      F2

<400> SEQUENCE: 65
cagtctgtgc tgactcagcc cccctcagcg tccgggaccc ccgggcagag ggtcaccatc      60
tcttgttctg gaagcagctc caacatcaaa tttaacagtg ttaactggta tcagcaactc    120
ccaggaacgg cccccaaact cctcatctat agtaataatc agcgaccctc aggggtccct    180
gaccgattct ctggctccaa gtctggcact tcagcctccc tggccatcag tgggctccag    240
tctgaggatg aggctgatta ttactgttct tcttgggatg atgatgctcg tggaactatt    300
ttcggcggag ggaccaagct gaccgtcctg                                     330

<210> SEQ ID NO 66
<211> LENGTH: 330
<212> TYPE: DNA
<213> ORGANISM: Artificial sequence
<220> FEATURE:
<223> OTHER INFORMATION: Synthetic sequence: Nucleotide sequence of light chain variable domain sequence for anti-PD-1 antibody clone
G1

<400> SEQUENCE: 66

```
cagtctgtgc tgactcagcc ccctcagcg tccgggaccc ccgggcagag ggtcaccatc      60
tcttgttctg gaagcagctc caacatcaaa tttaacagtg ttaactggta tcagcaactc     120
ccaggaacgg cccccaaact cctcatctat agtaataatc agcgaccctc aggggtccct    180
gaccgattct ctggctccaa gtctggcact tcagcctccc tggccatcag tgggctccag    240
tctgaggatg aggctgatta ttactgtgct gcttgggatg atgtttatta tggaactatt    300
ttcggcggag ggaccaagct gaccgtcctg                                     330
```

<210> SEQ ID NO 67
<211> LENGTH: 330
<212> TYPE: DNA
<213> ORGANISM: Artificial sequence
<220> FEATURE:
<223> OTHER INFORMATION: Synthetic sequence: Nucleotide sequence of
      light chain variable domain sequence for anti-PD-1 antibody clone
      G2

<400> SEQUENCE: 67

```
cagtctgtgc tgactcagcc ccctcagcg tccgggaccc ccgggcagag ggtcaccatc      60
tcttgttctg gaagcagctc caacatcaaa tttaacagtg ttaactggta tcagcaactc     120
ccaggaacgg cccccaaact cctcatctat agtaataatc agcgaccctc aggggtccct    180
gaccgattct ctggctccaa gtctggcact tcagcctccc tggccatcag tgggctccag    240
tctgaggatg aggctgatta ttactgtgct tcttgggatg attctcttta tggaactgtt    300
ttcggcggag ggaccaagct gaccgtcctg                                     330
```

<210> SEQ ID NO 68
<211> LENGTH: 330
<212> TYPE: DNA
<213> ORGANISM: Artificial sequence
<220> FEATURE:
<223> OTHER INFORMATION: Synthetic sequence: Nucleotide sequence of
      light chain variable domain sequence for anti-PD-1 antibody clone
      G10

<400> SEQUENCE: 68

```
cagtctgtgc tgactcagcc ccctcagcg tccgggaccc ccgggcagag ggtcaccatc      60
tcttgttctg gaagcagctc caacatcaaa tttaacagtg ttaactggta tcagcaactc     120
ccaggaacgg cccccaaact cctcatctat agtaataatc agcgaccctc aggggtccct    180
gaccgattct ctggctccaa gtctggcact tcagcctccc tggccatcag tgggctccag    240
tctgaggatg aggctgatta ttactgtgct gcttgggatg atgcttatta tggaactatt    300
ttcggcggag ggaccaagct gaccgtcctg                                     330
```

<210> SEQ ID NO 69
<211> LENGTH: 330
<212> TYPE: DNA
<213> ORGANISM: Artificial sequence
<220> FEATURE:
<223> OTHER INFORMATION: Synthetic sequence: Nucleotide sequence of
      light chain variable domain sequence for anti-PD-1 antibody clone
      H4

<400> SEQUENCE: 69

```
cagtctgtgc tgactcagcc ccctcagcg tccgggaccc ccgggcagag ggtcaccatc      60
```

```
tcttgttctg aagcagctc caacatcaaa tttaacagtg ttaactggta tcagcaactc     120
ccaggaacgg cccccaaact cctcatctat agtaataatc agcgaccctc aggggtccct     180
gaccgattct ctggctccaa gtctggcact tcagcctccc tggccatcag tgggctccag     240
tctgaggatg aggctgatta ttactgtgct tcttgggatg atgtttatcg tggaactgtt     300
ttcggcggag ggaccaagct gaccgtcctg                                       330
```

<210> SEQ ID NO 70
<211> LENGTH: 330
<212> TYPE: DNA
<213> ORGANISM: Artificial sequence
<220> FEATURE:
<223> OTHER INFORMATION: Synthetic sequence: Nucleotide sequence of
      light chain variable domain sequence for anti-PD-1 antibody
      codon-optimised clone H4

<400> SEQUENCE: 70

```
cagagcgtcc tgacacagcc cccaagcgca agcggaaccc ccggccagcg agtgaccatt     60
agttgtagtg aagtagtag taacatcaag ttcaactccg tgaattggta tcagcagctg     120
cccggaactg ctcctaaact gctgatctat tctaacaatc agcgaccaag tggcgtcccc     180
gaccggttca gcggctccaa gtctgggacc agtgcctcac tggctattag cgggctccag     240
tccgaggacg aagcagatta ctattgcgcc agctgggacg atgtgtacag gggcaccgtc     300
ttcggcgggg gaacaaaact gaccgtcctg                                       330
```

<210> SEQ ID NO 71
<211> LENGTH: 330
<212> TYPE: DNA
<213> ORGANISM: Artificial sequence
<220> FEATURE:
<223> OTHER INFORMATION: Synthetic sequence: Nucleotide sequence of
      light chain variable domain sequence for anti-PD-1 antibody clone
      H9

<400> SEQUENCE: 71

```
cagtctgtgc tgactcagcc cccctcagcg tccgggaccc ccgggcagag ggtcaccatc     60
tcttgttctg gaagcagctc caacatcaaa tttaacagtg ttaactggta tcagcaactc     120
ccaggaacgg cccccaaact cctcatctat agtaataatc agcgaccctc aggggtccct     180
gaccgattct ctggctccaa gtctggcact tcagcctccc tggccatcag tgggctccag     240
tctgaggatg aggctgatta ttactgttct tcttgggatg attctcttta tggaactatt     300
ttcggcggag ggaccaagct gaccgtcctg                                       330
```

<210> SEQ ID NO 72
<211> LENGTH: 366
<212> TYPE: DNA
<213> ORGANISM: Artificial sequence
<220> FEATURE:
<223> OTHER INFORMATION: Synthetic sequence: Nucleotide sequence of
      heavy chain variable domain sequence for anti-PD-1 antibody clone
      A3

<400> SEQUENCE: 72

```
caggtccagc tggtgcagtc cggggggaggc gtggtccagc ctgggcggtc cctgagactc     60
tcctgtgcag cctctggatt caccttcagt agctatggca tgcactgggt ccgccaggct     120
ccaggcaagg ggctggagtg ggtggcagtt atatcatatg atggaagtaa taaatactac     180
gcagactccg tgaagggccg attcaccatc tccagagaca attccaagaa cacgctgtat     240
ctgcaaatga acagcctgag agccgaggac acggctgtgt attactgtgc gagtgatctt     300
```

```
ggtgctggtc cttattatta tggtaaggat cattggggcc aagggaccac ggtcaccgtc    360
tcaagc                                                               366
```

<210> SEQ ID NO 73
<211> LENGTH: 366
<212> TYPE: DNA
<213> ORGANISM: Artificial sequence
<220> FEATURE:
<223> OTHER INFORMATION: Synthetic sequence: Nucleotide sequence of
      heavy chain variable domain sequence for anti-PD-1 antibody clone
      A10

<400> SEQUENCE: 73

```
caggtccagc tggtgcagtc tgggggaggc gtggtccagc ctgggcggtc cctgagactc    60
tcctgtgcag cctctggatt caccttcagt agctatggca tgcactgggt ccgccaggct    120
ccaggcaagg ggctggagtg ggtggcagtt atatcatatg atggaagtaa taaatactac    180
gcagactccg tgaagggccg attcaccatc tccagagaca attccaagaa cacgctgtat    240
ctgcaaatga acagcctgag agccgaggac acggctgtgt attactgtgc gagtgatctt    300
ggtgctggtc cttattatta tggtaaggat gtttggggcc aagggaccac ggtcaccgtc    360
tcaagc                                                               366
```

<210> SEQ ID NO 74
<211> LENGTH: 122
<212> TYPE: PRT
<213> ORGANISM: Artificial sequence
<220> FEATURE:
<223> OTHER INFORMATION: Synthetic sequence: Encoded amino acid sequence
      of heavy chain variable domain sequence for anti-PD-1 antibody
      codon-optimised clone A10

<400> SEQUENCE: 74

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Asp Leu Gly Ala Gly Pro Tyr Tyr Tyr Gly Lys Asp Val Trp
            100                 105                 110

Gly Gln Gly Thr Thr Val Thr Val Ser Ser
        115                 120
```

<210> SEQ ID NO 75
<211> LENGTH: 366
<212> TYPE: DNA
<213> ORGANISM: Artificial sequence
<220> FEATURE:
<223> OTHER INFORMATION: Synthetic sequence: Nucleotide sequence of
      heavy chain variable domain sequence for anti-PD-1 antibody
      codon-optimised clone A10

<400> SEQUENCE: 75

```
caggtgcagc tggtcgaatc cggggggggg gtggtgcagc tggacggtc actgagactg    60 agttgtgccg cctctgggtt tactttcagc tcctatggca tgcactgggt gaggcaggct   120
cccggcaagg ggctggagtg ggtggcagtc atctcttacg acggcagtaa caagtactat   180
gccgatagcg tcaaagggcg gttcactatt tcaagagaca cagcaaaaa tacccctgtac  240 ctccagatga acagcctgcg ggccgaagac acagctgtgt actattgcgc atctgatctg   300
ggagccggcc ttactatta cggcaaggat gtctggggc agggaaccac agtcaccgtc    360
tcaagc                                                              366
```

<210> SEQ ID NO 76
<211> LENGTH: 366
<212> TYPE: DNA
<213> ORGANISM: Artificial sequence
<220> FEATURE:
<223> OTHER INFORMATION: Synthetic sequence: Nucleotide sequence of
      heavy chain variable domain sequence for anti-PD-1 antibody clone
      B6

<400> SEQUENCE: 76

```
caggtccagc tggtagagtc cggggggaggc gtggtccagc ctgggcggtc cctgagactc    60
tcctgtgcag cctctggatt caccttcagt agctatggca tgcactgggt ccgccaggct   120
ccaggcaagg ggctggagtg ggtggcagtt atatcatatg atggaagtaa taaatactac   180
gcagactccg tgaagggccg attcaccatc tccagagaca attccaagaa cacgctgtat   240
ctgcaaatga acagcctgag agccgaggac acggctgtgt attactgtgc gagtgattat   300
ggtgctggtc cttattatta tggtatggat gttggggcc aagggaccac ggtcaccgtc    360
tcaagc                                                              366
```

<210> SEQ ID NO 77
<211> LENGTH: 366
<212> TYPE: DNA
<213> ORGANISM: Artificial sequence
<220> FEATURE:
<223> OTHER INFORMATION: Synthetic sequence: Nucleotide sequence of
      heavy chain variable domain sequence for anti-PD-1 antibody
      codon-optimised clone B6

<400> SEQUENCE: 77

```
caggtgcagc tggtggaaag cggggggggc gtggtgcagc tggaaggtc actgagactg    60 tcttgtgccg catctgggtt tacatttagc tcctatggca tgcactgggt gaggcaggct   120
cccggcaagg ggctggagtg ggtggcagtc atctcttacg acggcagtaa caagtactat   180
gccgatagcg tcaaagggcg gttcactatt tcaagagaca cagcaaaaa tacccctgtac  240 ctccagatga acagcctgcg ggccgaagac acagctgtgt actattgcgc atctgattac   300
ggagccggcc ttactatta cggcatggat gtctggggc agggaaccac agtcaccgtc    360
tcaagc                                                              366
```

<210> SEQ ID NO 78
<211> LENGTH: 366
<212> TYPE: DNA
<213> ORGANISM: Artificial sequence
<220> FEATURE:
<223> OTHER INFORMATION: Synthetic sequence: Nucleotide sequence of
      heavy chain variable domain sequence for anti-PD-1 antibody clone
      C4

<400> SEQUENCE: 78

```
caggtccagc tggtagagtc cggggggaggc gtggtccagc ctgggcggtc cctgagactc    60
```

```
tcctgtgcag cctctggatt caccttcagt agctatggca tgcactgggt ccgccaggct    120
ccaggcaagg ggctggagtg ggtggcagtt atatcatatg atggaagtaa taaatactac    180
gcagactccg tgaagggccg attcaccatc tccagagaca attccaagaa cacgctgtat    240
ctgcaaatga acagcctgag agccgaggac acggctgtgt attactgtgc gagtgatctt    300
ggtgctggtc cttattatta tggttttggat gtttggggcc aagggaccac ggtcaccgtc    360
tcaagc                                                                366
```

<210> SEQ ID NO 79
<211> LENGTH: 366
<212> TYPE: DNA
<213> ORGANISM: Artificial sequence
<220> FEATURE:
<223> OTHER INFORMATION: Synthetic sequence: Nucleotide sequence of
      heavy chain variable domain sequence for anti-PD-1 antibody
      codon-optimised clone C4

<400> SEQUENCE: 79

```
caggtgcagc tggtggaatc tgggggggg gtcgtgcagc ccggacggtc actgagactg    60
tcatgtgccg cttcagggtt tacttttagc tcctatggca tgcactgggt gaggcaggct    120
cccggcaagg ggctggagtg ggtggcagtc atctcttacg acggcagtaa caagtactat    180
gccgatagcg tcaagggcg gttcactatt tcaagagaca cagcaaaaa taccctgtac    240 ctccagatga acagcctgcg ggccgaagac acagctgtgt actattgcgc atctgatctg    300
ggagccggcc cttactatta cggcctggat gtctggggc agggaaccac agtcaccgtc    360
tcaagc                                                                366
```

<210> SEQ ID NO 80
<211> LENGTH: 366
<212> TYPE: DNA
<213> ORGANISM: Artificial sequence
<220> FEATURE:
<223> OTHER INFORMATION: Synthetic sequence: Nucleotide sequence of
      heavy chain variable domain sequence for anti-PD-1 antibody clone
      D4

<400> SEQUENCE: 80

```
caggtccagc tggtagagtc cggggggaggc gtggtccagc ctgggcggtc cctgagactc    60
tcctgtgcag cctctggatt caccttcagt agctatggca tgcactgggt ccgccaggct    120
ccaggcaagg ggctggagtg ggtggcagtt atatcatatg atggaagtaa taaatactac    180
gcagactccg tgaagggccg attcaccatc tccagagaca attccaagaa cacgctgtat    240
ctgcaaatga acagcctgag agccgaggac acggctgtgt attactgtgc gagtgatctt    300
ggtgctggtc cttattatta tggtatggat gtttggggcc aagggaccac ggtcaccgtc    360
tcaagc                                                                366
```

<210> SEQ ID NO 81
<211> LENGTH: 366
<212> TYPE: DNA
<213> ORGANISM: Artificial sequence
<220> FEATURE:
<223> OTHER INFORMATION: Synthetic sequence: Nucleotide sequence of
      heavy chain variable domain sequence for anti-PD-1 antibody clone
      E1

<400> SEQUENCE: 81

```
caggtccagc tggtagagtc cggggggaggc gtggtccagc ctgggcggtc cctgagactc    60
```

```
tcctgtgcag cctctggatt caccttcagt agctatggca tgcactgggt ccgccaggct    120
ccaggcaagg ggctggagtg ggtggcagtt atatcatatg atggaagtaa taaatactac    180
gcagactccg tgaagggccg attcaccatc tccagagaca attccaagaa cacgctgtat    240
ctgcaaatga acagcctgag agccgaggac acggctgtgt attactgtgc gagtgatctt    300
ggtgctggtc cttattatta tggtatggat gtttggggcc aagggaccac ggtcaccgtc    360
tcaagc                                                               366
```

<210> SEQ ID NO 82
<211> LENGTH: 366
<212> TYPE: DNA
<213> ORGANISM: Artificial sequence
<220> FEATURE:
<223> OTHER INFORMATION: Synthetic sequence: Nucleotide sequence of
      heavy chain variable domain sequence for anti-PD-1 antibody clone
      F2

<400> SEQUENCE: 82

```
caggtccagc tggtagagtc cggggggaggc gtggtccagc ctgggcggtc cctgagactc     60
tcctgtgcag cctctggatt caccttcagt agctatggca tgcactgggt ccgccaggct    120
ccaggcaagg ggctggagtg ggtggcagtt atatcatatg atggaagtaa taaatactac    180
gcagactccg tgaagggccg attcaccatc tccagagaca attccaagaa cacgctgtat    240
ctgcaaatga acagcctgag agccgaggac acggctgtgt attactgtgc gagtgatctt    300
ggtgctggtc cttattatta tggtatggat gtttggggcc aagggaccac ggtcaccgtc    360
tcaagc                                                               366
```

<210> SEQ ID NO 83
<211> LENGTH: 366
<212> TYPE: DNA
<213> ORGANISM: Artificial sequence
<220> FEATURE:
<223> OTHER INFORMATION: Synthetic sequence: Nucleotide sequence of
      heavy chain variable domain sequence for anti-PD-1 antibody clone
      G1

<400> SEQUENCE: 83

```
caggtccagc tggtagagtc cggggggaggc gtggtccagc ctgggcggtc cctgagactc     60
tcctgtgcag cctctggatt caccttcagt agctatggca tgcactgggt ccgccaggct    120
ccaggcaagg ggctggagtg ggtggcagtt atatcatatg atggaagtaa taaatactac    180
gcagactccg tgaagggccg attcaccatc tccagagaca attccaagaa cacgctgtat    240
ctgcaaatga acagcctgag agccgaggac acggctgtgt attactgtgc gagtgatctt    300
ggtgctggtc cttattatta tggtatggat gtttggggcc aagggaccac ggtcaccgtc    360
tcaagc                                                               366
```

<210> SEQ ID NO 84
<211> LENGTH: 366
<212> TYPE: DNA
<213> ORGANISM: Artificial sequence
<220> FEATURE:
<223> OTHER INFORMATION: Synthetic sequence: Nucleotide sequence of
      heavy chain variable domain sequence for anti-PD-1 antibody clone
      G2

<400> SEQUENCE: 84

```
caggtccagc tggtagagtc cggggggaggc gtggtccagc ctgggcggtc cctgagactc     60
tcctgtgcag cctctggatt caccttcagt agctatggca tgcactgggt ccgccaggct    120
```

```
ccaggcaagg ggctggagtg ggtggcagtt atatcatatg atggaagtaa taaatactac    180
gcagactccg tgaagggccg attcaccatc tccagagaca attccaagaa cacgctgtat    240
ctgcaaatga acagcctgag agccgaggac acggctgtgt attactgtgc gagtgatctt    300
ggtgctggtc cttattatta tggtatggat gtttggggcc aagggaccac ggtcaccgtc    360
tcaagc                                                                366
```

<210> SEQ ID NO 85
<211> LENGTH: 366
<212> TYPE: DNA
<213> ORGANISM: Artificial sequence
<220> FEATURE:
<223> OTHER INFORMATION: Synthetic sequence: Nucleotide sequence of
      heavy chain variable domain sequence for anti-PD-1 antibody clone
      G10

<400> SEQUENCE: 85

```
caggtccagc tggtagagtc cggggggaggc gtggtccagc ctgggcggtc cctgagactc     60
tcctgtgcag cctctggatt caccttcagt agctatggca tgcactgggt ccgccaggct    120
ccaggcaagg ggctggagtg ggtggcagtt atatcatatg atggaagtaa taaatactac    180
gcagactccg tgaagggccg attcaccatc tccagagaca attccaagaa cacgctgtat    240
ctgcaaatga acagcctgag agccgaggac acggctgtgt attactgtgc gagtgattat    300
ggtgctggtc cttattatta tggtatggat gtttggggcc aagggaccac ggtcaccgtc    360
tcaagc                                                                366
```

<210> SEQ ID NO 86
<211> LENGTH: 366
<212> TYPE: DNA
<213> ORGANISM: Artificial sequence
<220> FEATURE:
<223> OTHER INFORMATION: Synthetic sequence: Nucleotide sequence of
      heavy chain variable domain sequence for anti-PD-1 antibody clone
      H4

<400> SEQUENCE: 86

```
caggtccagc tggtagagtc cggggggaggc gtggtccagc ctgggcggtc cctgagactc     60
tcctgtgcag cctctggatt caccttcagt agctatggca tgcactgggt ccgccaggct    120
ccaggcaagg ggctggagtg ggtggcagtt atatcatatg atggaagtaa taaatactac    180
gcagactccg tgaagggccg attcaccatc tccagagaca attccaagaa cacgctgtat    240
ctgcaaatga acagcctgag agccgaggac acggctgtgt attactgtgc gagtgatctt    300
ggttctggtt attatcttta tggtatggac gtctggggcc aagggaccac ggtcaccgtc    360
tcaagc                                                                366
```

<210> SEQ ID NO 87
<211> LENGTH: 366
<212> TYPE: DNA
<213> ORGANISM: Artificial sequence
<220> FEATURE:
<223> OTHER INFORMATION: Synthetic sequence: Nucleotide sequence of
      heavy chain variable domain sequence for anti-PD-1 antibody
      codon-optimised clone H4

<400> SEQUENCE: 87

```
caggtgcagc tggtggagag cggggggggg gtggtgcagc ctggacggtc actgagactg     60
agttgcgccg catctggatt cacatttagc tcctacggca tgcactgggt gaggcaggca    120
```

```
cccggcaagg ggctggagtg ggtggccgtc atctcttatg acggcagtaa caagtactat    180
gctgatagcg tcaaagggcg gttcactatt tcaagagaca acagcaaaaa taccctgtac    240
ctccagatga atagcctgcg ggccgaagac acagctgtgt actattgcgc ctccgatctg    300
ggatctggct actatctgta tggcatggat gtctgggggc agggaaccac agtcaccgtc    360
tcaagc                                                                366

<210> SEQ ID NO 88
<211> LENGTH: 366
<212> TYPE: DNA
<213> ORGANISM: Artificial sequence
<220> FEATURE:
<223> OTHER INFORMATION: Synthetic sequence: Nucleotide sequence of
      heavy chain variable domain sequence for anti-PD-1 antibody clone
      H9

<400> SEQUENCE: 88
caggtccagc tggtagagtc cggggggaggc gtggtccagc ctgggcggtc cctgagactc    60
tcctgtgcag cctctggatt caccttcagt agctatggca tgcactgggt ccgccaggct    120
ccaggcaagg ggctggagtg ggtggcagtt atatcatatg atggaagtaa taaatactac    180
gcagactccg tgaagggccg attcaccatc tccagagaca attccaagaa cacgctgtat    240
ctgcaaatga acagcctgag agccgaggac acggctgtgt attactgtgc gagtgatctt    300
ggtgctggtc cttattatta tggtatggat gtttggggcc aagggaccac ggtcaccgtc    360
tcaagc                                                                366

<210> SEQ ID NO 89
<211> LENGTH: 5
<212> TYPE: PRT
<213> ORGANISM: Artificial sequence
<220> FEATURE:
<223> OTHER INFORMATION: Synthetic sequence: HC-CDR1

<400> SEQUENCE: 89

Ser Tyr Gly Met His
1               5
```